(12) United States Patent
Gandola et al.

(10) Patent No.: US 10,645,905 B2
(45) Date of Patent: May 12, 2020

(54) MICROELECTRONIC ANIMAL IDENTIFICATION

(71) Applicant: Somark Innovations, Inc., San Diego, CA (US)

(72) Inventors: Kent Raphael Gandola, San Diego, CA (US); Adrian Knight, Hunter Hill (AU); Eric Arlund, Germantown, NY (US); Gina Ma, San Diego, CA (US); George Albert Mansfield, San Diego, CA (US)

(73) Assignee: Somark Innovations, Inc., San Diego, CA (US)

( * ) Notice: Subject to any disclaimer, the term of this patent is extended or adjusted under 35 U.S.C. 154(b) by 898 days.

(21) Appl. No.: 14/778,489

(22) PCT Filed: Mar. 13, 2014

(86) PCT No.: PCT/US2014/026563
§ 371 (c)(1),
(2) Date: Sep. 18, 2015

(87) PCT Pub. No.: WO2014/151852
PCT Pub. Date: Sep. 25, 2014

(65) Prior Publication Data
US 2016/0037749 A1 Feb. 11, 2016

Related U.S. Application Data

(60) Provisional application No. 61/798,316, filed on Mar. 15, 2013.

(51) Int. Cl.
*A01K 11/00* (2006.01)
*A01K 29/00* (2006.01)
(Continued)

(52) U.S. Cl.
CPC .......... *A01K 11/006* (2013.01); *A01K 11/003* (2013.01); *A01K 11/005* (2013.01);
(Continued)

(58) Field of Classification Search
CPC .. A01K 11/005; A01K 11/006; A01K 29/005; A61B 90/90; A61B 17/3468; G01B 11/026; A61M 37/0069
(Continued)

(56) References Cited

U.S. PATENT DOCUMENTS

| | | | |
|---|---|---|---|
| 4,392,493 A | 7/1983 | Niemeijer | |
| 4,440,078 A | 4/1984 | McCrery, Jr. et al. | |

(Continued)

FOREIGN PATENT DOCUMENTS

| | | |
|---|---|---|
| CN | 1547430 A | 11/2004 |
| CN | 101057561 A | 10/2007 |

(Continued)

OTHER PUBLICATIONS

CN Application No. 201080049308.5 Office Action dated Apr. 1, 2014.
(Continued)

*Primary Examiner* — Diane D Yabut
*Assistant Examiner* — Majid Jamialahmadi
(74) *Attorney, Agent, or Firm* — Patterson Thuente Pedersen, P.A.

(57) ABSTRACT

Devices, systems and methods for microelectronic animal identification are disclosed. The microelectronic animal identification device includes an inserter configured to releasably holding the microelectronic chip at a distal end of the inserter, and an actuator configured to release the microelectronic chip from the inserter when the distal end of the inserter is inserted into a substrate of an animal body part. The microelectronic animal identification system includes a (Continued)

microelectronic chip and delivery system, a pigment marking device, a media transfer assembly for producing a pigment mark, a tissue sample device, and a data management system providing traceability of the animal and the materials used.

15 Claims, 56 Drawing Sheets

(51) Int. Cl.
| | |
|---|---|
| A61B 90/98 | (2016.01) |
| A61D 3/00 | (2006.01) |
| A61B 17/34 | (2006.01) |
| A61B 10/00 | (2006.01) |
| A61B 10/02 | (2006.01) |
| A61B 5/0488 | (2006.01) |
| A61B 5/0402 | (2006.01) |
| A61B 5/0205 | (2006.01) |
| A61B 5/0476 | (2006.01) |
| A61B 17/00 | (2006.01) |

(52) U.S. Cl.
CPC ........ *A01K 29/005* (2013.01); *A61B 5/02055* (2013.01); *A61B 5/0402* (2013.01); *A61B 5/0476* (2013.01); *A61B 5/0488* (2013.01); *A61B 10/0096* (2013.01); *A61B 10/02* (2013.01); *A61B 17/3468* (2013.01); *A61B 90/98* (2016.02); *A61D 3/00* (2013.01); *A61B 2017/00951* (2013.01)

(58) Field of Classification Search
USPC .......................................... 606/117, 129, 130
See application file for complete search history.

(56) References Cited

U.S. PATENT DOCUMENTS

| | | | | |
|---|---|---|---|---|
| 5,074,318 | A | * | 12/1991 | Campbell ............ A01K 11/006 128/899 |
| 5,551,319 | A | * | 9/1996 | Spaulding ............ A01K 11/005 30/362 |
| 6,013,122 | A | | 1/2000 | Klitzman et al. |
| 6,263,762 | B1 | | 7/2001 | Zeitler |
| 6,901,885 | B1 | | 6/2005 | Kleinsasser |
| 7,098,394 | B2 † | | 8/2006 | Armer |
| 8,353,917 | B2 † | | 1/2013 | Mandecki |
| 9,418,321 | B1 † | | 8/2016 | Gruda |
| 2003/0062988 | A1 | | 4/2003 | Mandecki et al. |
| 2004/0131234 | A1 | | 7/2004 | Long et al. |
| 2004/0144333 | A1 | | 7/2004 | Finlayson |
| 2004/0220527 | A1 | | 11/2004 | Buckley et al. |
| 2004/0244341 | A1 | | 12/2004 | Kurt |
| 2005/0051109 | A1 | | 3/2005 | Fantin et al. |
| 2006/0177649 | A1 | | 8/2006 | Clark et al. |
| 2007/0103314 | A1 | | 5/2007 | Geissler |
| 2008/0036846 | A1 | | 2/2008 | Hopkins et al. |
| 2008/0247637 | A1 | | 10/2008 | Gildenberg |
| 2009/0311295 | A1 | | 12/2009 | Mathiowitz et al. |
| 2010/0023021 | A1 | * | 1/2010 | Flaherty ............... A61B 5/0084 606/130 |
| 2010/0295682 | A1 | | 11/2010 | August et al. |
| 2011/0077659 | A1 | | 3/2011 | Mandecki et al. |
| 2012/0226288 | A1 | | 9/2012 | Mays et al. |
| 2013/0267962 | A1 | * | 10/2013 | Michelson ............ A61B 17/00 606/116 |
| 2014/0128880 | A1 | | 5/2014 | Gandola et al. |
| 2014/0204400 | A1 | * | 7/2014 | Budleski ................ G01B 11/02 356/625 |

FOREIGN PATENT DOCUMENTS

| | | |
|---|---|---|
| EP | 0300110 A2 | 1/1989 |
| EP | 1911347 A1 | 4/2008 |
| EP | 2967000 | 9/2014 |
| EP | 2840890 A1 | 3/2015 |
| WO | WO 98/41084 A1 | 9/1998 |
| WO | WO-02082892 A2 | 10/2002 |
| WO | WO-2011028926 A2 | 3/2011 |
| WO | WO-2013163339 A1 | 10/2013 |
| WO | WO-2014151852 A1 | 9/2014 |

OTHER PUBLICATIONS

CN Application No. 201080049308.5 Office Action dated May 2, 2013.
CN Application No. 201080049308.5 Office Action dated Oct. 30, 2013.
PCT Patent Application No. PCT/US2014/026563 International Preliminary Report on Patentability dated Sep. 15, 2015.
PCT Patent Application No. PCT/US2014/026563 International Search Report completed Jul. 18, 2014.
PCT Patent Application No. PCT/US2014/026563 Written Opinion completed Jul. 18, 2014.
PCT Patent Application No. PCT/US2010/047712 International Preliminary Report on Patentability and Written Opinion dated Mar. 6, 2012.
PCT Patent Application No. PCT/US2010/047712 International Search Report dated May 30, 2011.
PCT Patent Application No. PCT/US2013/038055 International Search Report dated Aug. 23, 2013.
PCT Patent Application No. PCT/US2013/038055 International Preliminary Report on Patentability dated Oct. 28, 2014.
U.S. Appl. No. 61/239,430, filed Sep. 2, 2009.
U.S. Appl. No. 61/637,767, filed Apr. 24, 2012.
U.S. Appl. No. 13/393,912 Restriction Requirement dated Oct. 31, 2014.

\* cited by examiner
† cited by third party

MICROELECTRONIC ANIMAL IDENTIFICATION

CROSS-REFERENCES TO RELATED APPLICATIONS

This application is a U.S. National State Entry of PCT/US2014/02656, filed Mar. 13, 2014; which claims the benefit of priority from U.S. Provisional Patent Application No. 61/798,316, filed Mar. 15, 2013, of which are incorporated by reference in their entirety.

FIELD OF THE INVENTION

The present disclosure relates to systems and methods for providing microelectronic animal identification

BACKGROUND

Animals are marked for identification in a variety of applications by a variety of methods. The ability to accurately identify and track individual animals is necessary in research environments where animals are exposed to different experimental conditions, in the management of colonies of genetically modified animals for which multiple genotypes are present, and in breeding stocks where it is useful to track which animals possess certain desirable and undesirable traits.

SUMMARY OF DISCLOSURE

The present disclosure is directed to microelectronic animal identification. According to one aspect of the present disclosure, a microelectronic animal identification device comprises an inserter configured to releasably hold a microelectronic chip at a distal end of the inserter, and an actuator configured to release the microelectronic chip from the inserter when the distal end of the inserter is inserted into a substrate of an animal body part. Optionally, the animal is a mouse, a rat, or a rodent; optionally, the body part is a tail; and optionally, the substrate is dermis.

In some embodiments, the identification device further comprises a controller configured to control position of the inserter and to actuate the actuator to implant the microelectronic chip into the substrate of the animal body part.

In some embodiments, the actuator is manually operated.

In some embodiments, the inserter terminates into a sharp tip capable of piercing into the substrate of the animal body parts.

In some embodiments, the inserter is configured to retain the microelectronic chip in proximity of the sharp tip.

In some embodiments, the inserter comprises a tubular body defining a lumen configures to securely retain the microelectronic chip at a distal end of the lumen.

In some embodiments, the lumen is dimensioned to limit the movement of microelectronic chip at the distal end of the lumen.

In some embodiments, the lumen has a diameter that is slightly larger than a cross-sectional profile of the microelectronic chip.

In some embodiments, the distal end of the lumen is dimension to approximate the cross-sectional profile of the microelectronic chip In some embodiments, the microelectronic chip is secured to the lumen by an adhesive.

In some embodiments, the tubular body terminates into a sharp tip extending distally beyond the microelectronic chip.

In some embodiments, the microelectronic chip includes a sharp end extending beyond a distal end of the tubular body.

In some embodiments, the actuator comprises a plunger slidably inserted into the lumen.

In some embodiments, the plunger is configured to engage and push the microelectronic chip out of the lumen when the distal end of the lumen is inserted into the substrate of the animal body part.

In some embodiments, the plunger is configured to disengage the microelectronic chip by a proximal movement of the plunger to limit rotation of the microelectronic chip in the substrate of the animal body part.

In some embodiments, the plunger is actuated by a controller.

In some embodiments, the plunger is manually actuated.

In some embodiments, the microelectronic chip comprises a photocell that provides power to the microelectronic chip.

In some embodiments, the microelectronic chip comprises an RF antenna capable of generating an RF signal that represents an identification number.

In some embodiments, the RF antenna comprises an antenna loop.

In some embodiments, the microelectronic chip further comprises an onboard logic circuitry capable of modulating current in the antenna loop to generate a different RF signal that represents a different identification number.

In some embodiments, the onboard logic circuitry is controlled by an electronic memory.

In some embodiments, the electronic memory is a ROM.

In some embodiments, the microelectronic chip further comprises an animal location detector.

In some embodiments, the microelectronic chip further comprises a laminated thin-film movement detector.

In some embodiments, the microelectronic chip further comprises a laminated thin-film vital sign detector.

In some embodiments, the vital sign detector is selected from the group consisting of heart rate detector, ECG detector, EEG detector, EMG detector, temperature detector, blood pressure detector, and combinations thereof.

In some embodiments, the microelectronic chip implant device is configured to implant the microelectronic chip into the epidermis of the animal body part at a depth that allows the RF signal to be detected.

In some embodiments, the microelectronic chip implant device is configured to implant the microelectronic chip into the epidermis of the animal body part at a depth that allows the photocell to be activated, optionally by a laser that emits 5-60 mW of optical power at 660 nm.

In some embodiments, the identification device further comprises a chip reading device for photo-activating the microelectronic chip and for receiving the RF signal generated by the RF antenna.

In some embodiments, the chip reading device comprises a laser diode driver for photo-activating the microelectronic chip.

In some embodiments, the chip reading device comprises an optical focusing module.

In some embodiments, the chip reading device comprises an air coil pickup connected to an RF receiver for receiving the RF signal generated by the microelectronic chip.

In some embodiments, the chip reading device comprises a field-programmable gate array (FGPA).

In some embodiments, the chip ready device comprises a USB microcontroller and power regulators.

According to another aspect of the present disclosure, animal marking systems that incorporate the microelectronic animal identification device are disclosed.

In some embodiments, the marking system further comprises at least one restraining device operatively associated with the identification device, wherein the restraining device is sized and configured for restraining an animal or animal body part thereof and oriented such that the identification device can deposit a microelectronic chip into the substrate of the animal body part;

In some embodiments, the inserter is coupled to an inserter cartridge.

In some embodiments, the inserter cartridge comprises a reference feature configured to position the inserter cartridge on the identification device with precision.

In some embodiments, the reference feature comprises a locating cylinder extending between two end plates.

In some embodiments, the identification device comprises a docking member coupled to a scotch yoke, the docking member defining a receiving slot extending from a top surface to a bottom surface of the docking member.

In some embodiments, the locating cylinder of the reference feature is configured to be inserted into the receiving slot of the docking member.

In some embodiments, the two end plates of the reference feature respectively engage the top and bottom surfaces of the docking member when the locating cylinder of the reference feature is inserted into the receiving slot of the docking member.

In some embodiments, the locating cylinder comprises a center bore through which the inserter extends.

In some embodiments, the inserter cartridge comprises a locking feature configured to lock the inserter cartridge onto the identification device.

In some embodiments, the locking feature comprises a U-shaped flexible locking clip extending between two ends; each end of the locking clip comprises at least one outwardly extending locking tooth.

In some embodiments, the locking clip further comprises a plurality of gripping ribs on an exterior surface of the locking clip.

In some embodiments, the locking teeth are configured to abut an end wall of a scotch yoke of the microelectronic chip implant device when the inserter cartridge is in a mounted position.

In some embodiments, the inserter is coupled to the inserter cartridge by means of an adhesive.

In some embodiments, the inserter is coupled to the inserter cartridge by molding the inserter to the inserter cartridge.

In some embodiments, the inserter is molded from a polymer material.

In some embodiments, the inserter cartridge is permanently affixed to the identification device.

In some embodiments, the inserter cartridge is removable to allow replacement of worn or damaged inserters.

In some embodiments, the microelectronic chip implant device comprises multiple inserter cartridges dimensioned to account for differences in animal substrate size or geometry.

In some embodiments, the multiple inserter cartridges are pre-mounted onto the microelectronic chip implant device.

In some embodiments, the marking system is configured to automatically mount and dismount the inserter.

In some embodiments, the restraining device comprises a spring-loaded tapered v-groove configured to compensate for differences in size of the marking substrate.

In some embodiments, the spring-loaded tapered v-groove is modulated to compensate for differences in size of the substrate body part.

In some embodiments, the spring-loaded tapered v-groove is assembled in a support mount, and is optionally enclosed within a protective compliant boot.

In some embodiments, the modulated spring-loaded tapered v-groove comprises a plurality of independent groove sections, each groove section being articulating and self-aligning.

In some embodiments, the marking system is configured to select the inserter and the configuration of the restraining device based on the size of the marking substrate.

In some embodiments, the marking system further comprises a measuring gauge configured to measure the size of the substrate of the animal body part, the measuring gauge comprising a plurality of measuring slots with incrementally increasing widths.

In some embodiments, the marking system further comprises a measuring device configured to measure the size of the substrate of the animal body part by using a laser-generating device emitting a light curtain beam and a receiver that is incorporated into the measuring device.

In some embodiments, the marking system further comprises a forked tool adapted to engage and compress the locking clip to facilitate removal of the inserter cartridge from the microelectronic chip implant device.

In some embodiments, the forked tool is integrated with a measuring gauge comprising a plurality of measuring slots with incrementally increasing widths.

In some embodiments, the marking system further comprises a marking device for depositing a pigment composition into the substrate of the animal body parts.

In some embodiments, the marking device comprises a marking needle of fixed length comprising one or a plurality of needle tips.

In some embodiments, the needle tips are configured to penetrate the epidermis of the marking substrate and transfer a pigment into the dermis of the marking substrate.

In some embodiments, the marking system further comprises a media transfer assembly containing the pigment, wherein the marking device is configured to make a mark by contacting the pigment prior to the marking substrate.

In some embodiments, the identification device is operated by a controller to deposit the microelectronic chip in a proximal to distal direction parallel to the animal tail.

In some embodiments, the microelectronic chip implant device is operated by the controller to implant the microelectronic chip in a distal to proximal direction parallel to the animal tail.

In some embodiments, the microelectronic chip implant device is operated by the controller to implant the microelectronic chip vertical to the animal tail.

According to another aspect of the present disclosure, a microelectronic chip for identification of an animal is disclosed. The microelectronic chip comprises a photocell that provides power to the microelectronic chip, an RF antenna capable of generating an RF signal that represents an identification number, and a laminated thin-film detector.

In some embodiments, the laminated thin-film detector is a location detector.

In some embodiments, the laminated thin-film detector is a movement detector.

In some embodiments, the laminated thin-film detector is a vital sign detector.

In some embodiments, the vital sign detector is selected from the group consisting of heart rate detector, ECG detector, EEG detector, EMG detector, temperature detector, blood pressure detector, and combinations thereof.

According to another aspect of the present disclosure, an animal identification system is disclosed. The animal identification system comprises a microelectronic chip implanted in a substrate of an animal, the microelectronic chip is photo-activated to generate an RF signal that represent a first identification number; and a pigment mark imprinted in the substrate of an animal, the pigment mark representing a second identification number.

According to another aspect of the present disclosure, an animal identification system is disclosed. The animal identification system comprises a microelectronic chip implanted in a substrate of an animal, the microelectronic chip is passively activated by an RF energy source to generate an RF signal that represent a first identification number; and a pigment mark imprinted in the substrate of an animal, the pigment mark representing a second identification number.

In some embodiments, the identification system further comprises a tissue storage container for containing a sample tissue of the animal, taken from the animal at the time of the chip implantation and/or at the time of marking, and placed into the storage container, wherein the tissue storage container comprises a second microelectronic chip configured to an RF signal that represent the first identification number.

In yet another embodiment, the identification system further comprises a media transfer assembly containing the marking pigment, wherein the media transfer assembly comprises a bar-code that associatively represents the first identification number.

In some embodiments, the identification system further comprises a media transfer assembly, wherein a third microelectronic chip is affixed and is configured to an RF signal that corresponds to the first identification number, and optionally also includes a secondary bar-coding reference, for traceability to the manufacturer and manufacturing lot number of, for example, the assembly and/or the pigment.

In some embodiments, the identification system further comprises a data management system for storing and cross-referencing the first, second and third identification numbers.

These and other aspects and features of the disclosure will be better understood upon reading the following detailed description in conjunction with the accompanying drawings.

Figure 1:
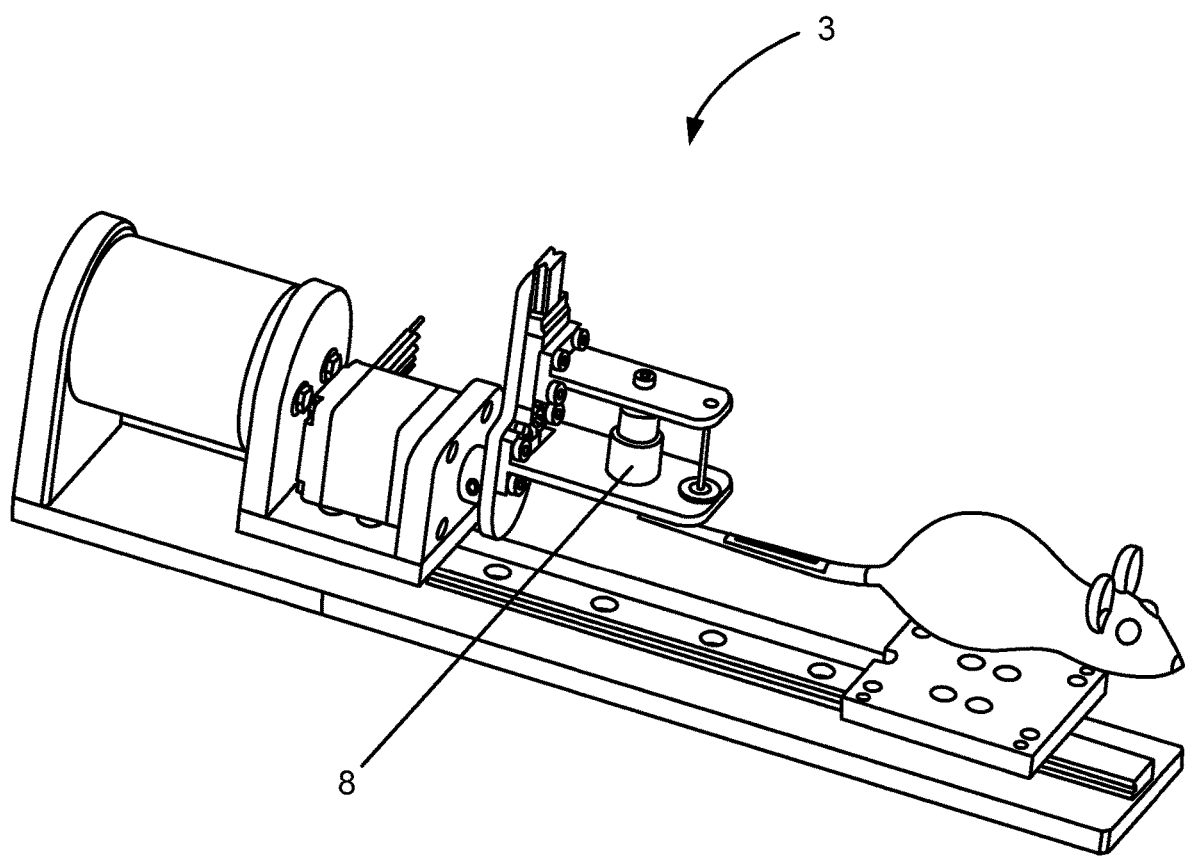
FIG. 1 depicts a microelectronic animal identification device (stand-alone) of the present disclosure.
Figure 2:
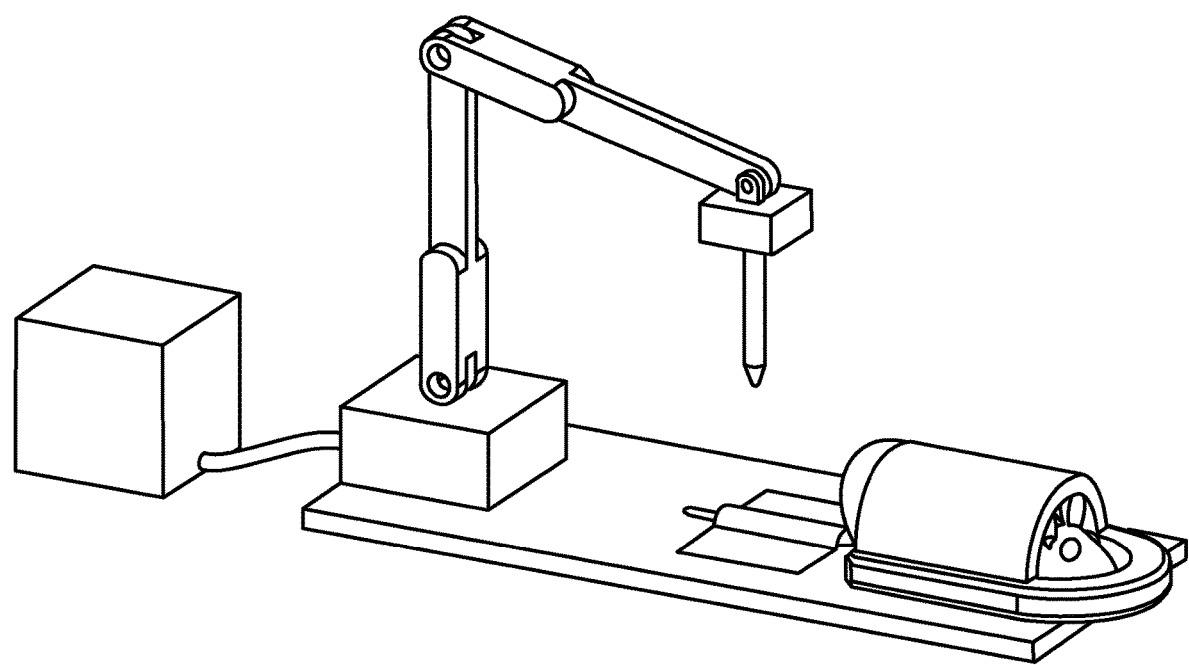
FIG. 2 depicts a microelectronic animal identification device (with restraining device) of the present disclosure.
Figure 3:
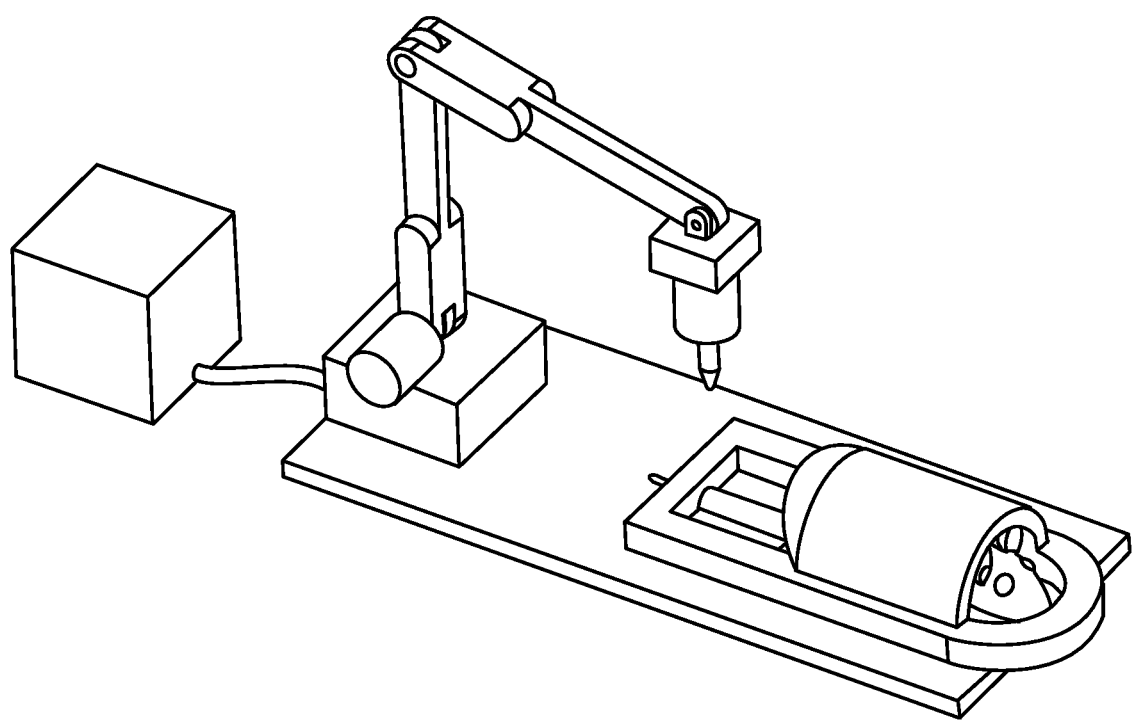
FIG. 3 depicts a microelectronic animal identification device (with restraining device) of the present disclosure.

It should be understood that the drawings are not necessarily to scale and that the disclosed embodiments are sometimes illustrated diagrammatically and in partial views. In certain instances, details which are not necessary for an understanding of the disclosed apparatus or method which render other details difficult to perceive may in some embodiments have been omitted. It should be understood, of course, that this disclosure is not limited to the particular embodiments illustrated herein.

DETAILED DESCRIPTION OF EMBODIMENTS

As used here, the following definitions and abbreviations apply.

As described herein, the term "exemplary" (or "e.g." or "by example") means a non-limiting example. The term "exemplary" is not specifically intended to indicate a preferred example.

As described herein, the term "bio-safe" means is substantially non-toxic to an animal when used in the disclosed manner. Determinants of toxicity are known in the art. Optionally, toxicity is determined with respect to one of: mortality, effect on overall health, disease state, perturbation of an animal's normal activities (upon acute and/or chronic exposure), and the like.

As described herein, the term "body part restraint" means a restraining a device which immobilizes a body part of an animal. Optionally, a body part restraint immobilizes a substrate portion of an animal. For example, a body part restraint can immobilize a substrate portion of an animal by contacting the substrate portion itself, or contacting a different portion of the animal such that the substrate portion is immobilized.

As described herein, the term "bio-permanent" means remains in or on an animal for a substantial duration of the animal's life.

As described herein, the term "skin" means the external covering or integument of an animal body. In one embodiment, it includes subdermal cartilage and/or matrix.

As described herein, the term "proximal" and "distal" refer to the direction in which the marking device marks the marking substrate (e.g. tails) of an animal. Specifically, the term "proximal" refers to the direction towards the animal's body and the term "distal" refers to the direction towards the animal's extremity.

As described herein, the term "tip length deviation" refers to length uniformity of a group of co-planar inserter tips, in which "tip length deviation" is the maximum distance between the common plane and any out-of-plane inserter tip(s).

As described herein, the term "tip concentration deviation" refers to the X-Y positioning uniformity of a compact group of inserter tips, in which "tip concentration deviation" is the maximum distance between the geometric center of the grouped inserter tips and the X-Y reference feature of the inserter cartridge (e.g. the center axis of the locating cylinder).

When describing the media transfer assembly of the marking system, the term "lower" refers to a position relatively closer to the marking substrate, and the term "upper" refers to a relatively further away from the marking substrate.

The present disclosure generally provides a microelectronic animal identification device and an animal marking system that are configured to mark an animal with one or more features. For example, the mark may in some embodiments be durable, easily applied, relatively non-invasive, may in some embodiments have a safety profile, low level of cross-read (e.g. less interference produced by other animals in proximity to each other), and may in some embodiments be read with a high level of accuracy (e.g. greater than about 80% or greater than about 90% or greater than about 95% accuracy). In some embodiment, the animals are marked with at least two features: a microelectronic chip that is photo-activated and configured to generate an RF signal in response that represents a first identification number, and a pigment imprint that represents a second identification number. The first and second identification numbers can be the same or different numbers, and can be stored in a data management system for cross-referencing.

In some embodiments, the animals are marked with at least two features: a microelectronic chip that is passively-activated by means of an RF source and configured to generate an RF signal in response that represents a first identification number, and a pigment imprint that represents a second identification number. The first and second identification numbers can be the same or different numbers, and can be stored in a data management system for cross-referencing.

In addition, the pigment contained within the media transfer assembly may be further identified with a tertiary identification such as a microelectronic chip or an imprinted bar-code, providing traceability to the pigment manufacturer, manufacturing lot, raw materials, etc.

In still other embodiments the animal may additionally be identified by means of a tissue sample, taken at the time of chip implantation and/or imprint marking, provided with a $3^{rd}$ microelectronic chip, given a third identification number which can be the same or different from the first and second identification numbers, and can be stored in a data management system for cross-referencing.

In terms of non-limiting examples, the tissue sample can include; a tail snip, a skin sample, an ear snip, a blood sample, or other comparable extremity tissue sample.

Figure 42A:
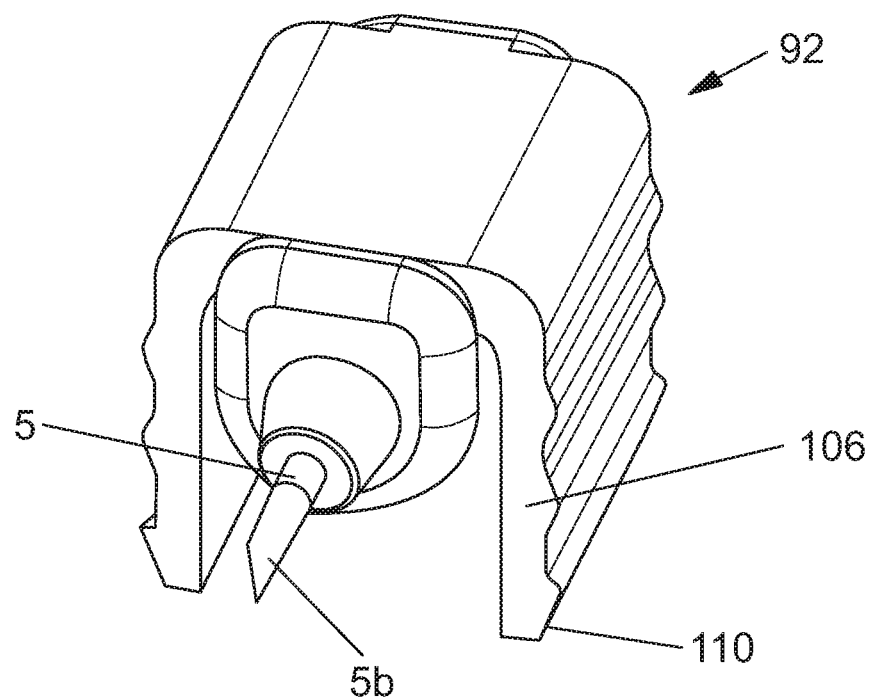
FIG. 42A depicts an exemplary inserter coupled to an exemplary inserter cartridge according to the present disclosure.
Figure 42B:
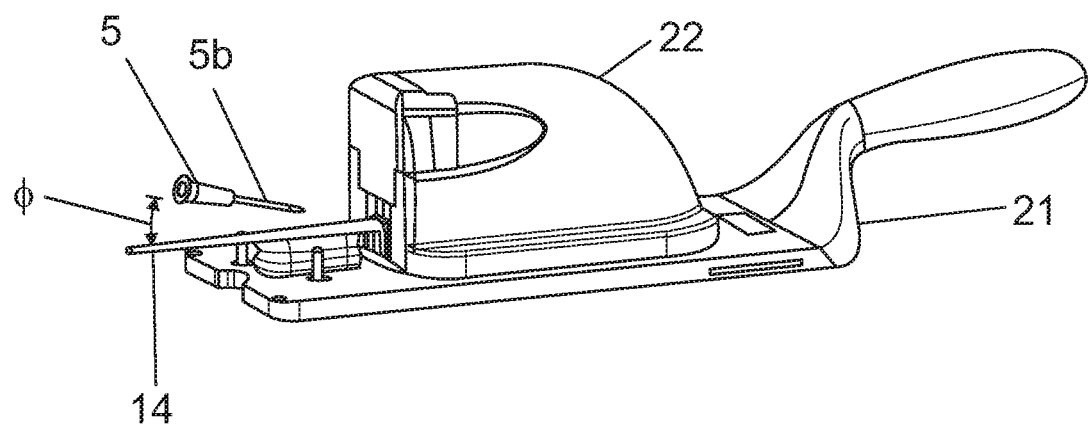
FIG. 42B depicts an exemplary orientation Φ of the inserter needle tip 5*b* used with restraining device of FIG. 21A when coupled to the exemplary inserter 5 coupled to an exemplary inserter cartridge according to the present disclosure.
Figure 43:
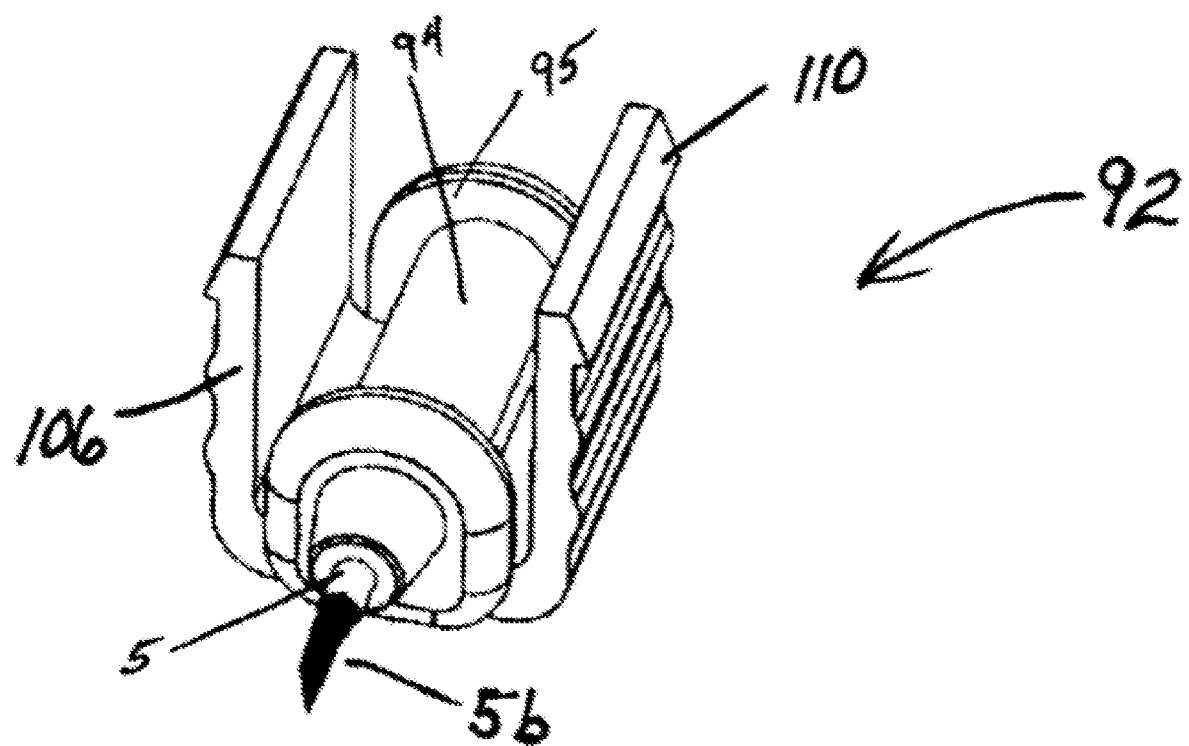
FIG. 43 depicts an exemplary inserter coupled to an exemplary inserter cartridge according to the present disclosure.
Figure 44:
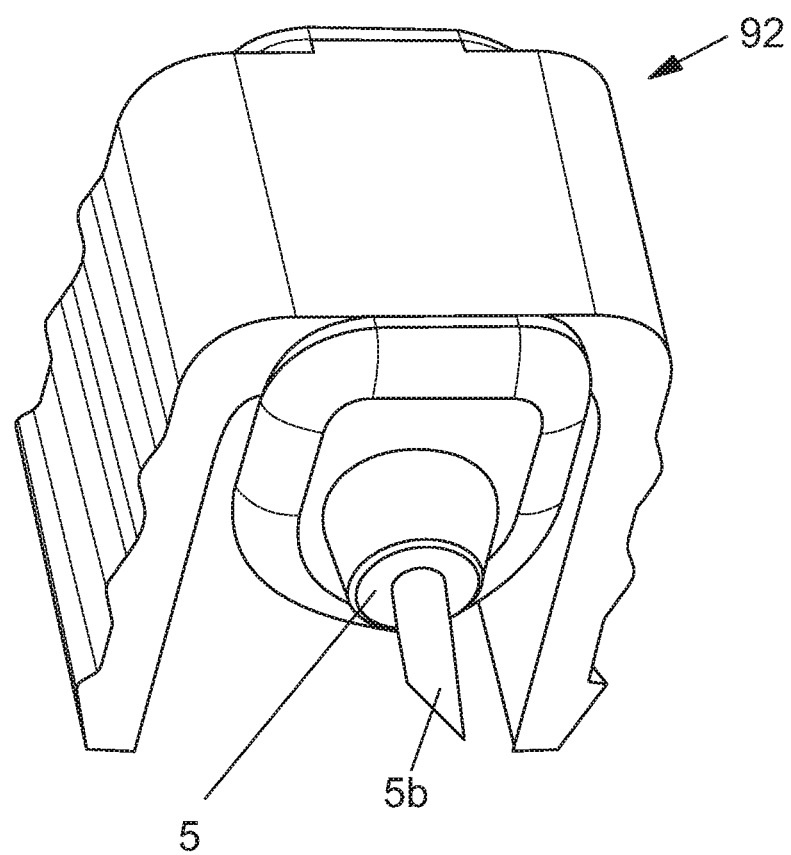
FIG. 44 depicts an exemplary inserter coupled to an exemplary inserter cartridge according to the present disclosure.

As illustrated in FIG. 42B, the microelectronic animal identification device according to the present disclosure includes an inserter needle 5b configured to releasably hold the microelectronic chip at a distal end of the inserter needle, and an actuator 8 configured to push a plunger 230 to release the microelectronic chip 300 from the inserter needle 5b when the distal end of the inserter needle 220 is inserted into a substrate of an animal body part. The microelectronic chip 300 is a stand-alone device in some embodiments. In some embodiments the microelectronic chip is integrated into a marking system.

Figure 4:
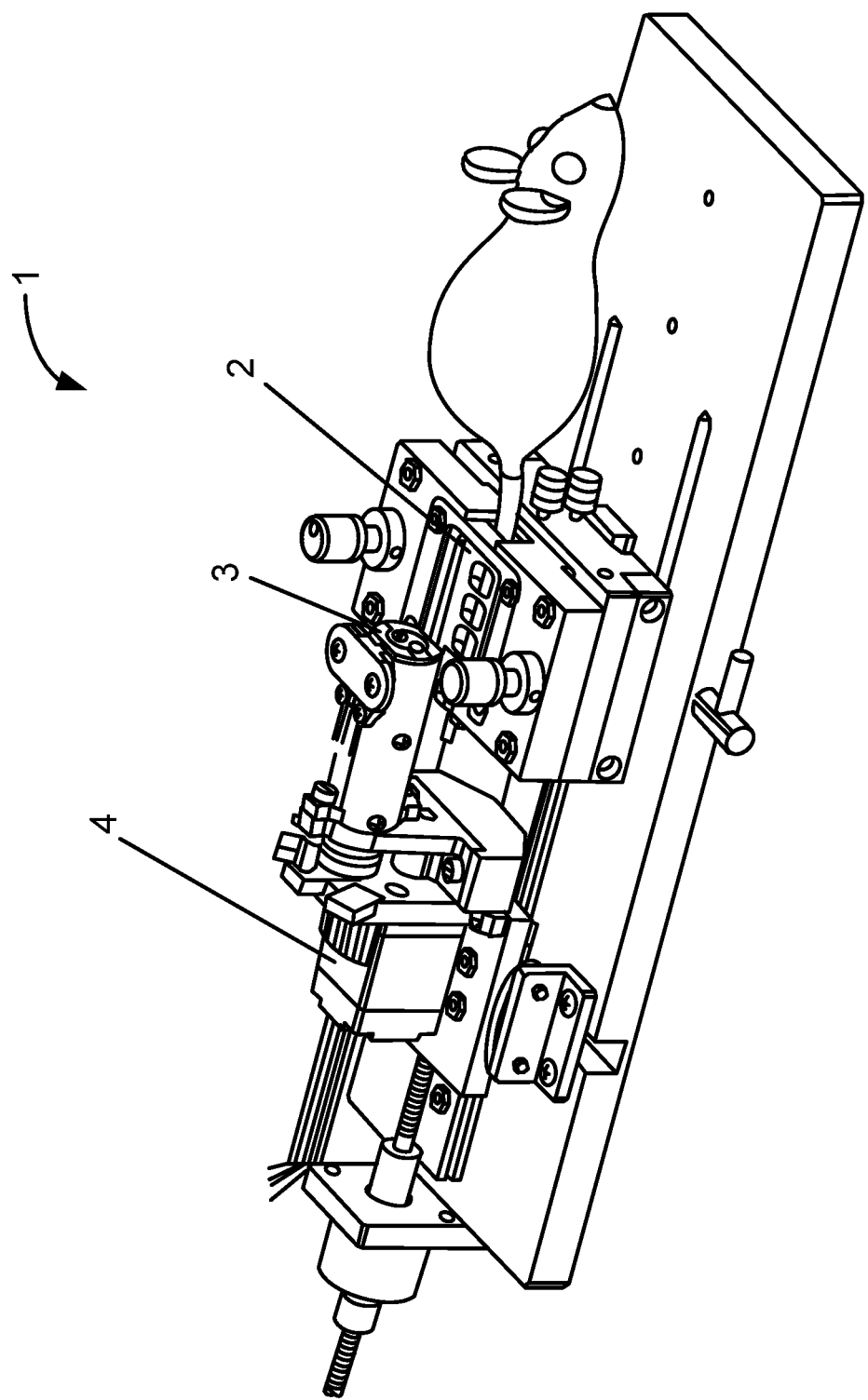
FIG. 4 depicts a microelectronic animal identification device (integrated with marking system) of the present disclosure.

Turning to FIG. 4, the visual identification (pigment tattooing) device 3 is integrated into a marking system 1, which further includes a restraining device 2 and a controller 4. In operation, the restraining device 2 immobilizes a marking substrate of an animal body part, while the controller 4 operates the identification device 3 to make a readable mark on the marking substrate, such as by depositing a pigment under the skin of the marking substrate, as described in greater detail below.

Microelectronic Identification Device

Figure 53:
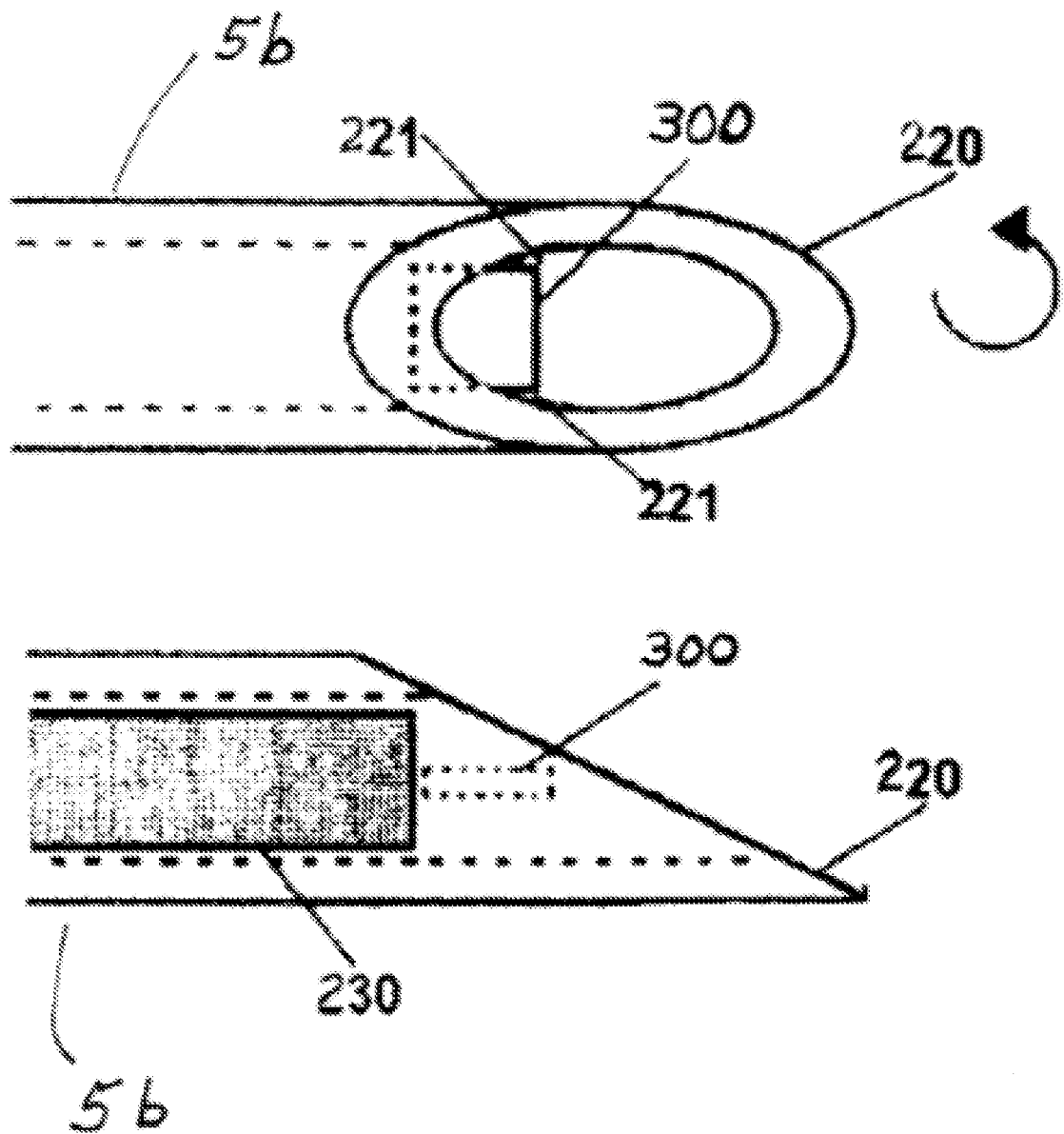
FIG. 53 depicts an exemplary inserter (in partially view) according to the present disclosure.
Figure 54:
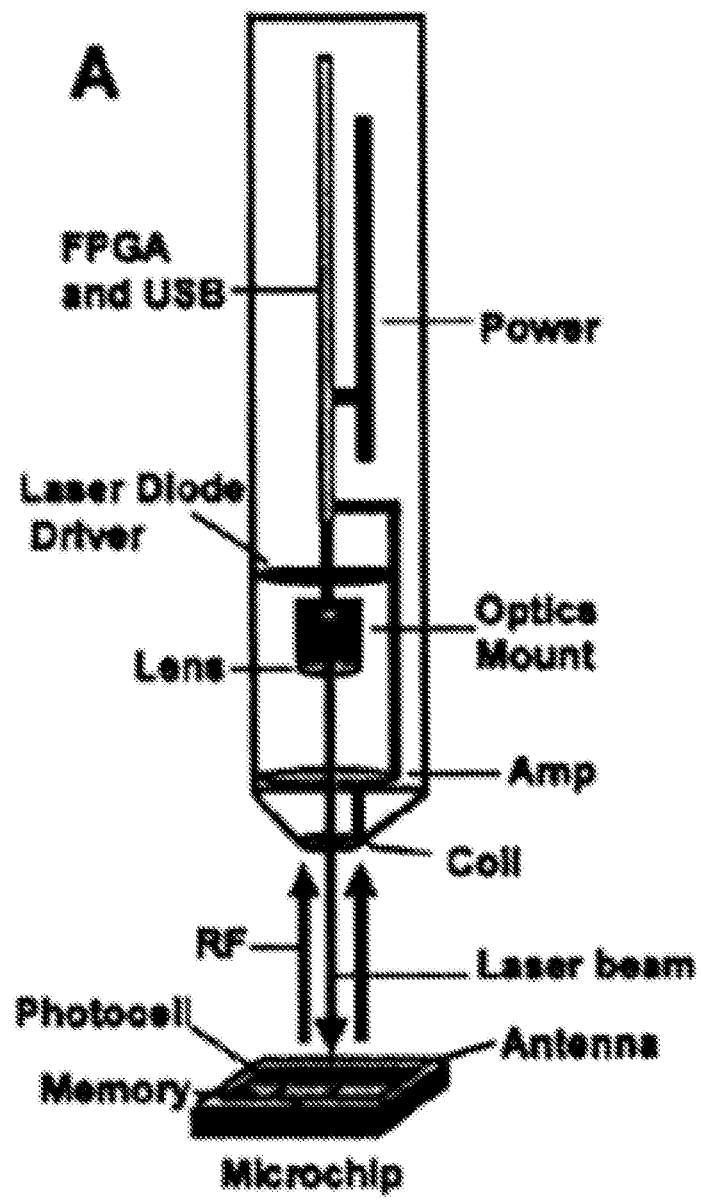
FIG. 54 depicts an exemplary chip reading device according to the present disclosure.

As discussed above, the visual identification device 3, illustrated in FIG. 4 of the present disclosure, in some embodiments deposits a microelectronic chip 300, as illustrated in FIG. 53 into a substrate (e.g. dermis) of an animal's body part, such as a mouse tail. To that end, the visual identification device 3 includes an inserter (needle) 5b as illustrated in FIG. 42B, configured to releasably hold the microelectronic chip 300 at a distal end of the inserter needle 5b (illustrated in FIG. 53), and an actuator 8 is configured to push a plunger 230 to release the microelectronic chip 300 from the inserter needle lumen 221 when the distal end 220 of the inserter needle 5b is inserted into a substrate of an animal body part.

Figure 50:
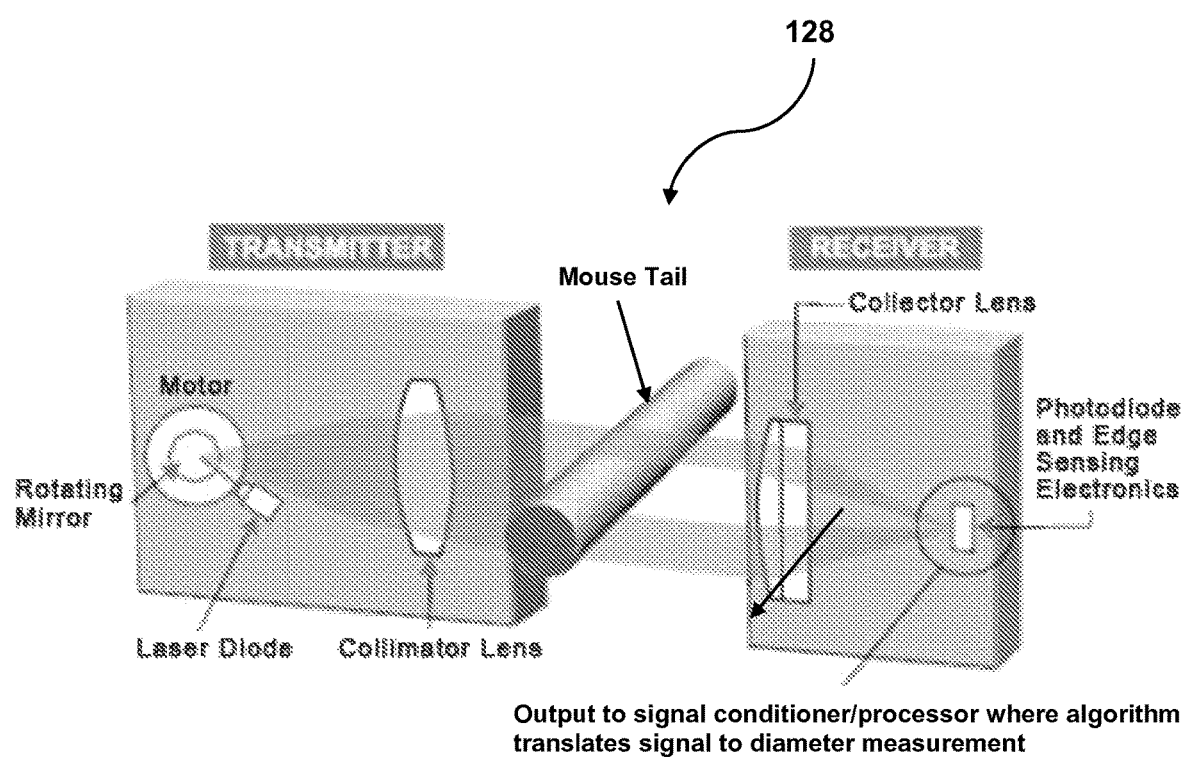
FIG. 50 schematically depicts an exemplary tail size measuring gauge based on laser beam according to the present disclosure.
Figure 51:
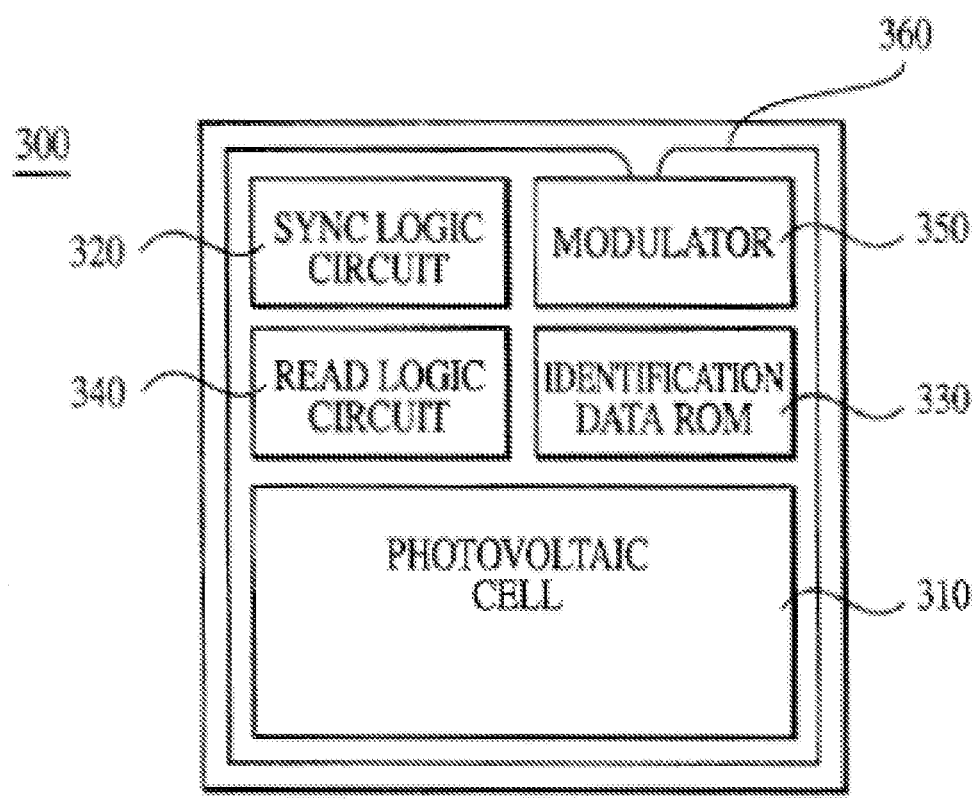
FIG. 51 depicts an exemplary microelectronic chip according to the present disclosure.
Figure 52:
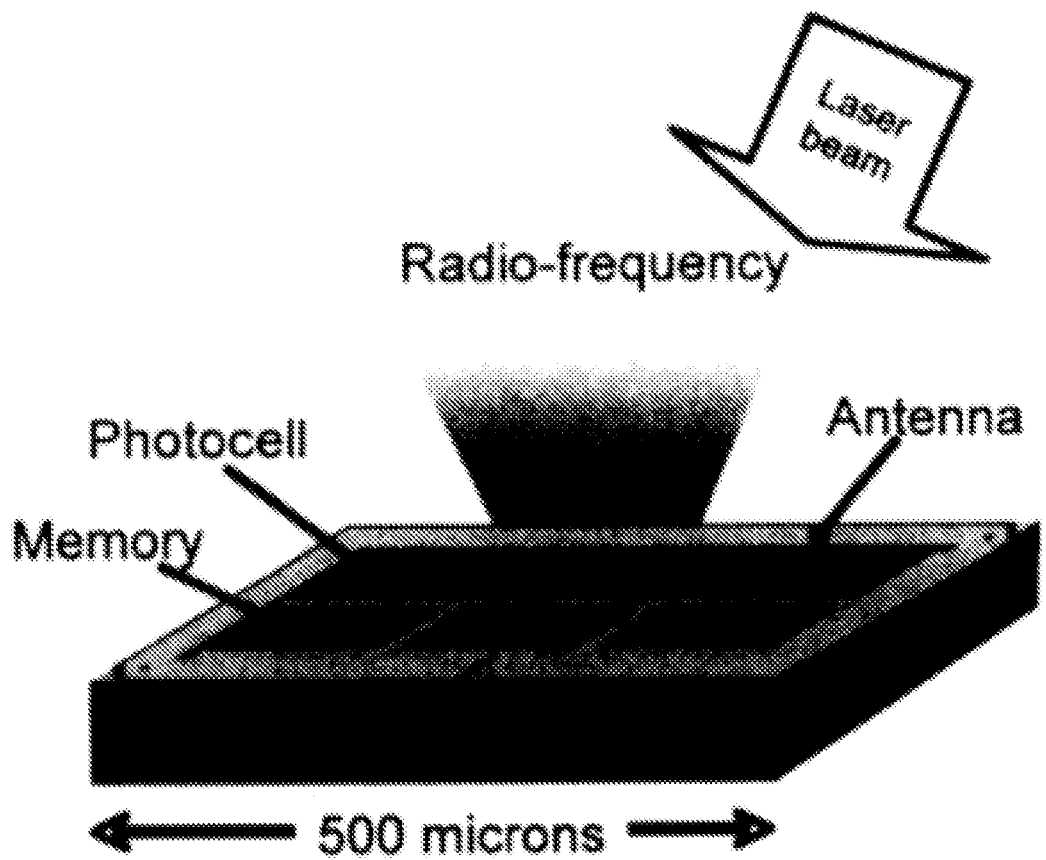
FIG. 52 depicts an exemplary microelectronic chip according to the present disclosure.

In some embodiment, the inserter is described in U.S. Patent Application Publication No. 2011/0077659, incorporated herein in its entirety. In some embodiment, the microelectronic chip 300 and a chip reading device 128 as illustrated in FIG. 50 is disclosed in U.S. Pat. No. 7,098,394, incorporated herein in its entirety; and in U.S. Patent Application Publication No. 2003/0062988, incorporated herein in its entirety.

The identification device 3 in some embodiments includes a robot assembly 42 that is driven by a controller, and an inserter 5 operatively associated with the robot assembly 42.

In one embodiment, the robotic assembly 42 described herein is meant to embrace any robotic configuration that allows positioning of the inserter 5, whereby actuation of the inserter 5 marks the substrate. In another embodiment, a robotic assembly positions the inserter 5 along a y-axis and an R axis. In a further embodiment, the robotic assembly 42 operates or controls operation of the inserter 5, for example, by actuating the inserter 5 to mark the marking substrate. In another embodiment, the robotic assembly 42 positions the inserter 5 along a Y-axis, a theta axis, and along an R axis.

The robotic assembly 42 (in combination with one or more actuators) may in some embodiments be configured to position a inserter 5 along any axis. For example, in one embodiment, the robotic assembly 42 can position the inserter 5 along a linear axes (e.g. Y and/or R), rotational axes (e.g. theta), or a combination thereof.

With the teachings provided herein, the skilled artisan can readily produce robot assemblies 42 that enable a inserter 5 to move about a desired axis. For example, in one embodiment, the inserter 5 moves about a linear axis by providing a linear track or can move about any other axis (e.g. rotational axis) by providing a track that follows the desired axis. As another example, in one embodiment, the inserter 5 moves about a rotational axis by providing a radial arm (e.g. an arm that extends from a pivot point). As another example, in one embodiment, the inserter 5 moves about a linear axis by providing a piston coupled to a crank pin. As another example, in one embodiment, the inserter 5 moves about a linear axis by providing a rack and pinion mechanism (where the marking device is attached to a linear rack portion). As another example, in one embodiment, the inserter 5 moves about a non-circular curved axis by providing a rack and pinion mechanism (where the marking device is attached to. the rack portion and the rack/pinion combination is configured therefore). As another example, in one embodiment, the inserter 5 moves about a rotational axis by providing a rack and pinion mechanism (where the marking device is attached to a circular pinion portion or where the marking device is attached to the rack portion and the rack portion is a circular shape). As another example, in one embodiment, the inserter 5 moves about a curved axis by providing a crank-slider mechanism (where the slider is a pivoting slider).

The robotic assembly 42 comprises at least a first actuator (also referred to herein as a 'marking actuator') that causes the identification device to deposit the microelectronic chip on the substrate, i.e. that 'actuates for making a mark', as used herein. The robotic assembly 42 in one embodiment, further comprises one or more additional actuators for positioning the robotic arm (and marking device) on or about the substrate prior to making a mark on the substrate and/or homing or otherwise disengaging the identification device thereafter.

In one embodiment, the actuator(s) are any type of actuator, for example, a motor, voice coil, screw, piezoelectric device, solenoid, or pneumatic pump. Useful motors include, for example, stepper motors and servo motors. In one embodiment, the actuator is a linear actuator (e.g. Y axis actuator), a rotational actuator (e.g. theta axis actuator), or an actuator that converts from rotational to linear motion or vice-versa (e.g. of the piston type). The actuator (e.g. marking actuator) can cause a robotic arm or identification device thereof to move in a constant motion or a reciprocating motion.

The actuator (e.g. motor) may in some embodiments be optionally controlled by a feedback mechanism, for example, a feedback mechanism that provides positional information of the robotic arm or identification device thereof. Optionally, a feedback mechanism is external to the actuator and comprises a flag fixed to a robotic arm or identification device and a sensor fixed in position with respect to a restraining device (or vice-versa). For example, one or more flags can be provided for each axis of movement such that the marking device can be properly positioned. Optionally, the robot assembly 42 comprises a "substrate" flag (or multiple substrate window flags) on a robotic arm (e.g. an arm actuated by a second actuator), wherein the substrate flag is positioned such that the flag detected by a sensor when the robotic arm has positioned identification device about the substrate (in position for marking) A marking actuator (first actuator) can then be actuated to make a mark (e.g. controlled by a servo motor coupled to an identification device by a reciprocating piston).

Optionally, a feedback mechanism is internal to the actuator. For example, in one embodiment a servo motor is used to provide an actuator (e.g. a first actuator). Generally, a servo motor includes a motor, a feedback device, and a drive. The motor operates on direct current, and is typically hotter and smaller than other motors producing a comparable amount of torque. The feedback device is often an encoder or resolver (e.g. 32 count encoder) mounted on the back of the motor, and the feedback device reports performance information such as motor position and motor speed back to the drive. The servo motor's drive provides current to the motor, and the drive can include a programmable control device (e.g., a controller) which dictates the current in response to the feedback from the feedback device. A servo motor can be controlled by an algorithm such as the proportional-integral-derivative (PID) algorithm. In one embodiment, a servo motor provides properties when used in an actuator (e.g. coupled to an identification device through a reciprocating piston such as a scotch yolk assembly).

Among other various properties taught herein, a servo motor can optionally be provided as a marking actuator to impart a marking system with the ability to stop the identification device's motion at a position that reduces the amount of motion needed by the robotic arm to change positions. For example, a identification device can be fixed to a piston which is coupled to servo motor for reciprocating up/down "marking" motion of the identification device, and the servo motor can be operated with such precision that the inserter can stop cyclical movement at top dead center (e.g. upon completion of a mark or a character thereof). This feature eliminates the possibility of dragging the identification device (e.g. inserter) on the marking surface without the use of global upward (or Z-axis) movement of the robotic arm itself (e.g. by a second actuator).

Figure 6:
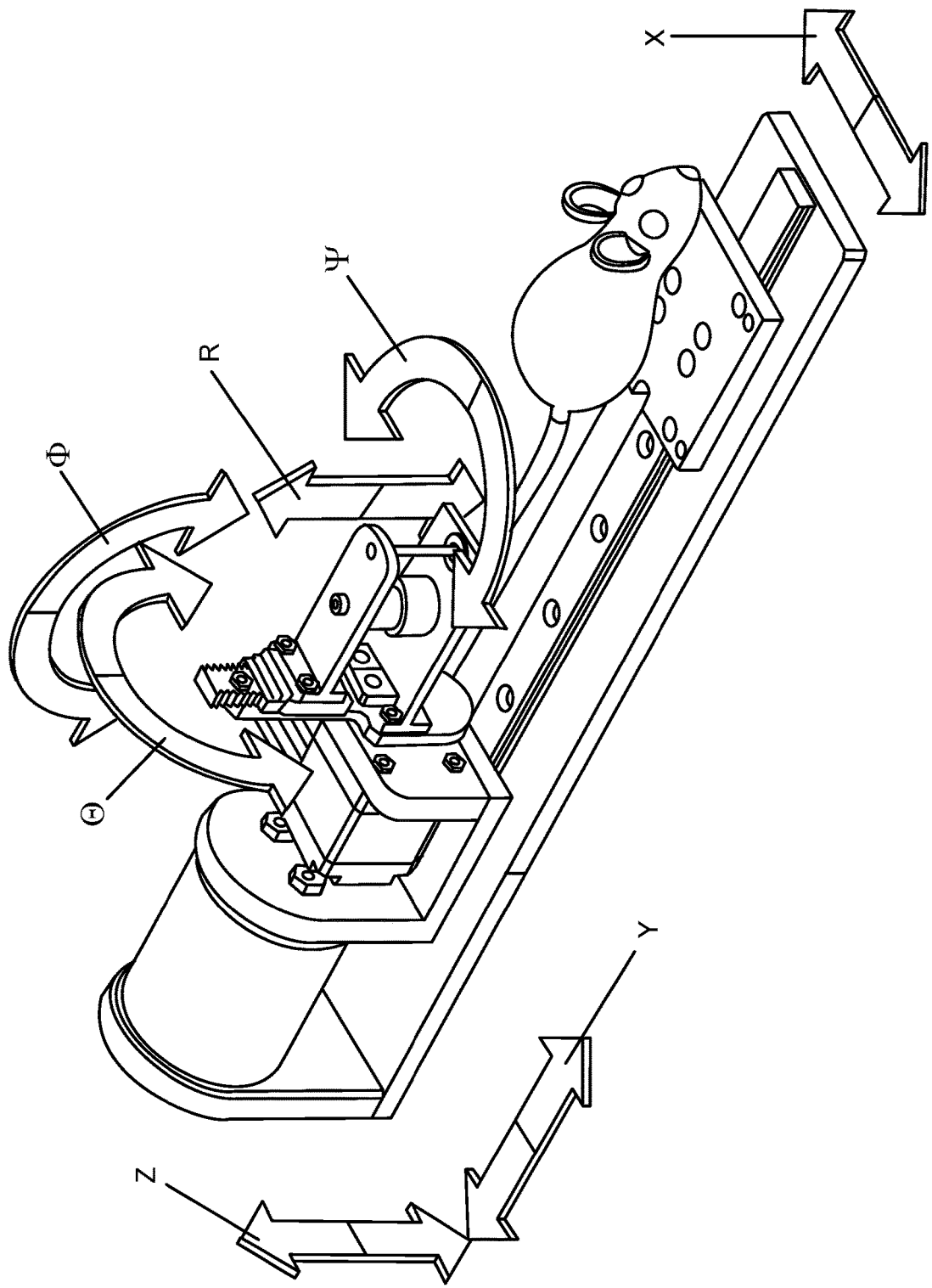
FIG. 6 depicts examples of optional axes about which the marking device and/or robotic arm can be configured to move.
Figure 7A:
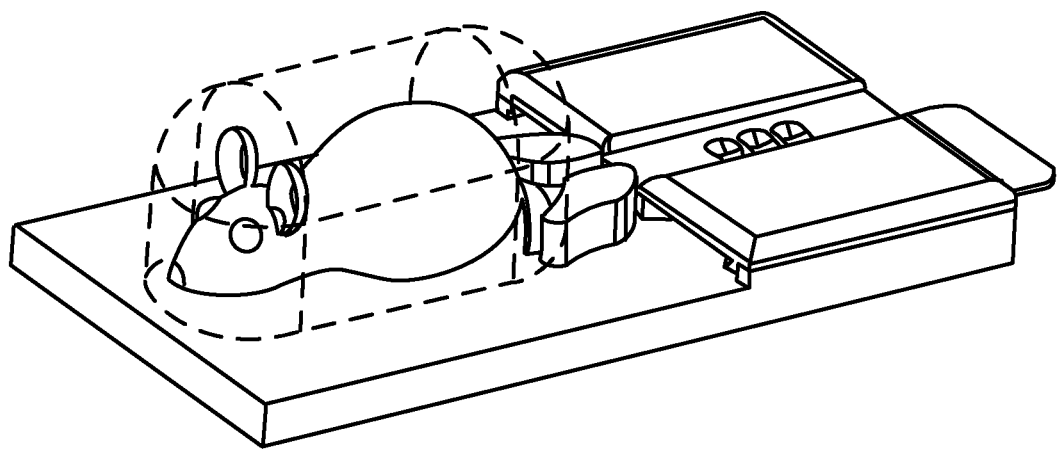
FIG. 7A depicts an exemplary restraining device according to the present disclosure, particularly showing the restraining device having a first part (broken line) that secures the main body of the animal and a second part (solid line) that secures the animal body part to be marked.
Figure 7B:
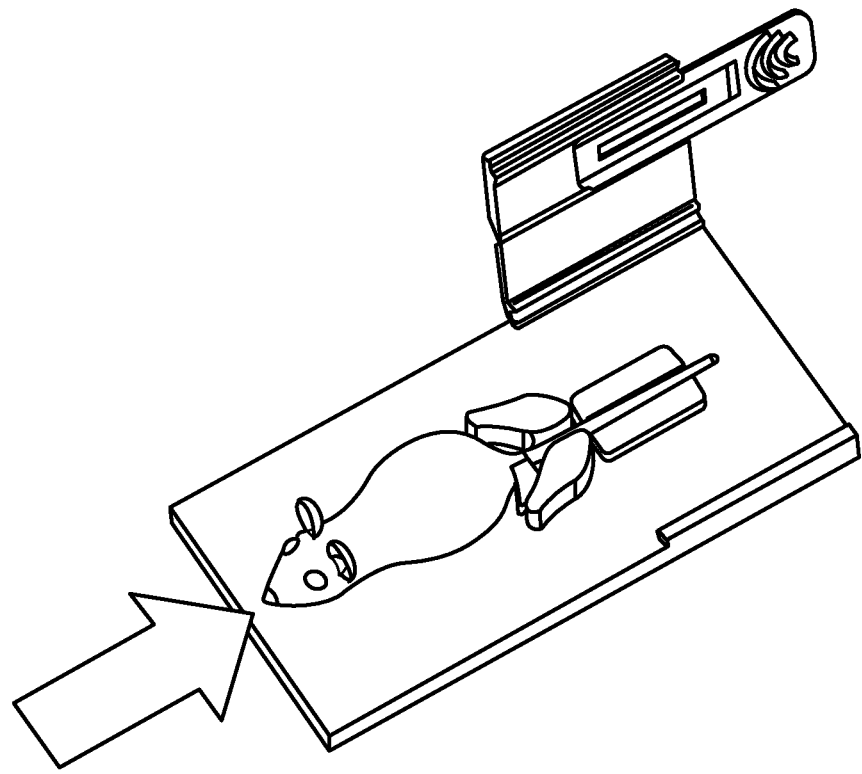
FIG. 7B depicts an exemplary restraining device according to the present disclosure, particularly showing the positioning of the animal by pushing the main body of the animal in the direction of arrow.
Figure 7C:
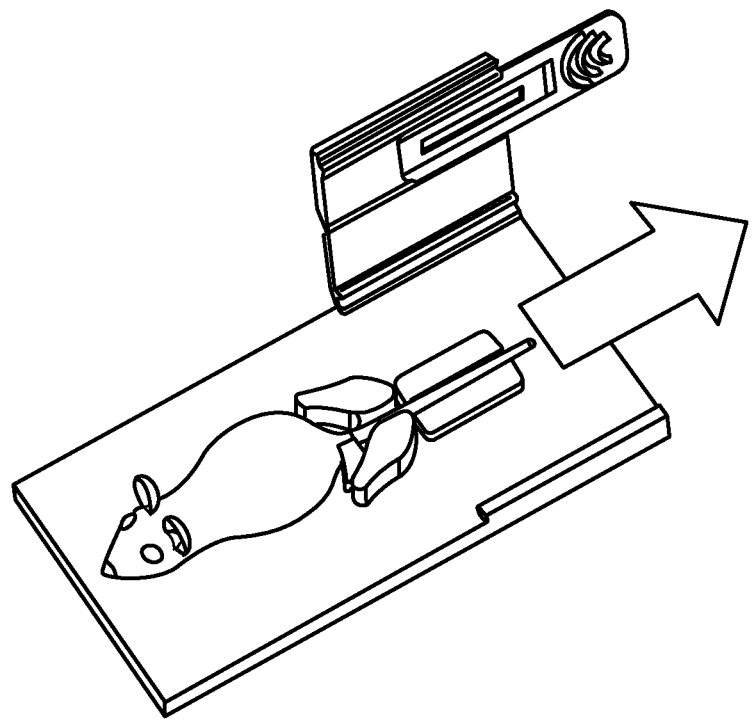
FIG. 7C depicts an exemplary restraining device according to the present disclosure, particularly showing the positioning of the animal by pulling the animal body part to be marked in the direction of arrow.
Figure 7D:
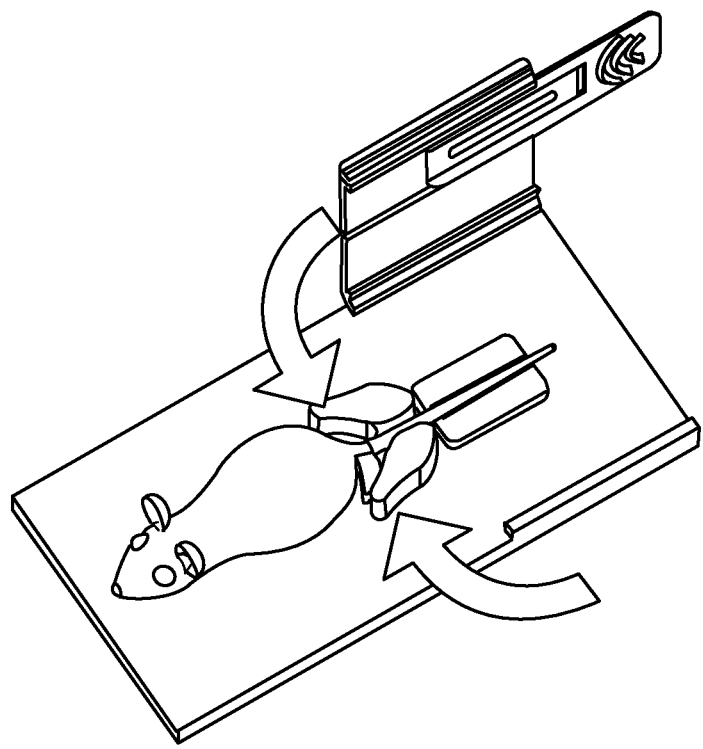
FIG. 7D depicts an exemplary restraining device according to the present disclosure, particularly showing the securing of the animal body part by the restraining device.

In one embodiment the actuator for marking a substrate actuates the identification device 3, and optionally, the robotic assembly 42 along one or more axes or around or about one or more points in space. Optional axes include linear axes and rotational axes, as depicted in FIG. 6 (note that the R axis is defined relative to Theta and Phi and is parallel with the Z axis when Theta and Phi are both equal to zero). Although not depicted in the figure, other optional axes include those that are defined relative to (e.g. normal to) theta and psi or psi and phi.

The skilled artisan will recognize that certain exemplary axes are defined relative to each other in robotic assemblies 42 of marking systems taught herein. For example, although certain descriptions and figures set forth the Z axis as the vertical axis, the skilled artisan will appreciate that this is done to illustrate the invention.

In one embodiment, an actuator actuates movement along a single axis. In another embodiment, an actuator actuates movement along a plurality of axes. Optionally, the identification device and/or robotic arm is capable of moving on plurality of axes, wherein movement along each of a plurality of axes is controlled be a different actuator.

Although the invention contemplates a marking system in which the identification device 3 and/or robotic assembly 42 is capable of moving on one, all, or less than all of the axes defined by FIG. 6 (e.g. independent of other axes). In such embodiments, the identification device 3 can be actuated for making a mark by an actuator that does not move the robotic assembly 42, i.e. does not move the robotic assembly 42 other than the identification device 3 (e.g. by placing the actuator between the arm and the identification device), for example, for providing precision movement of the identification device and/or reduced wear on the actuator compared to an actuator that moves both the identification device 3 and robotic assembly 42 simultaneously.

Useful robot assemblies 42 of the present invention can an actuator that causes a inserter 5 (of the identification device 3) to contact the substrate. Optionally, the actuator causes a marking member to pierce the substrate (e.g. to inject a tattoo). For example, the inserter can enter the skin and exit the skin along the same path, for example, by retracting from the skin, minimizing spread of the mark and tissue damage.

Figure 25:
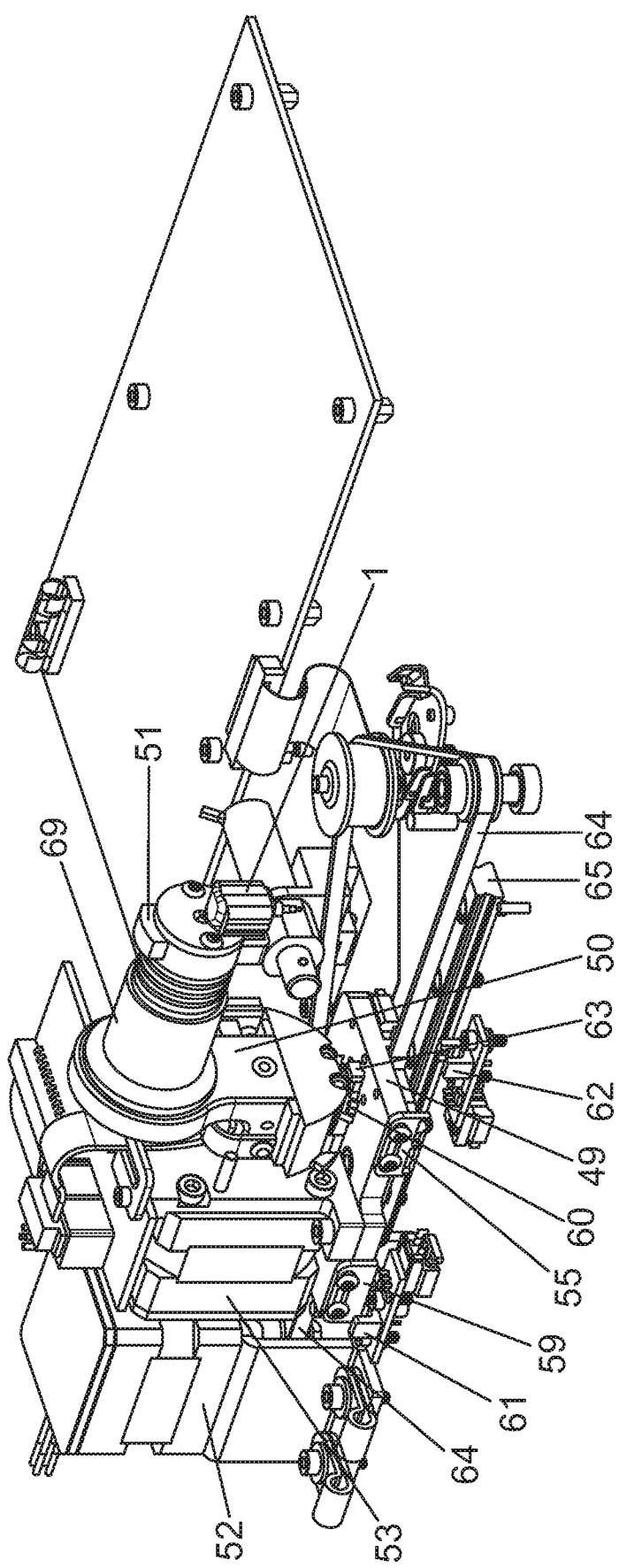
FIG. 25 depicts an exemplary robot assembly according to the present disclosure.
Figure 26:
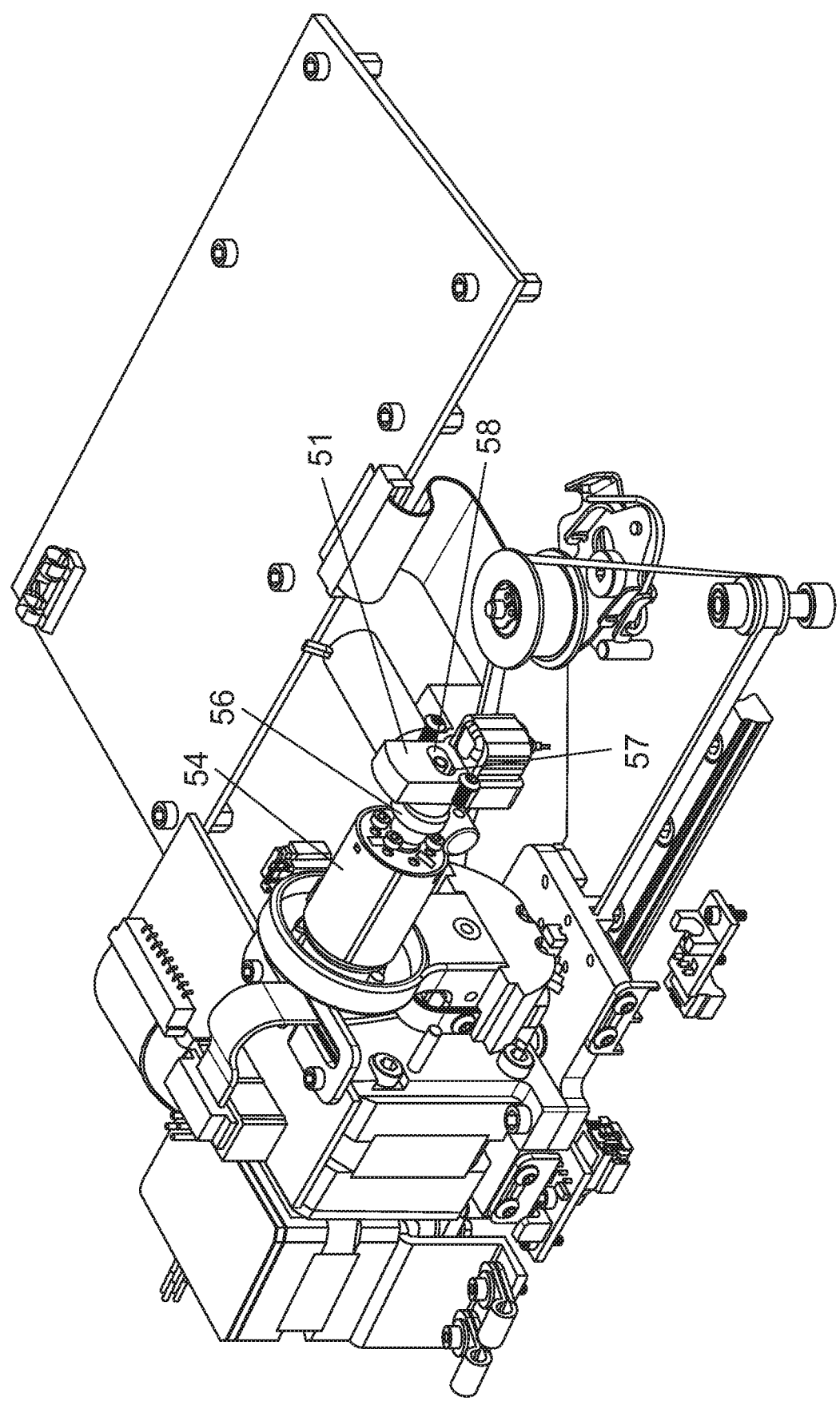
FIG. 26 depicts an exemplary robot assembly according to the present disclosure.
Figure 27:
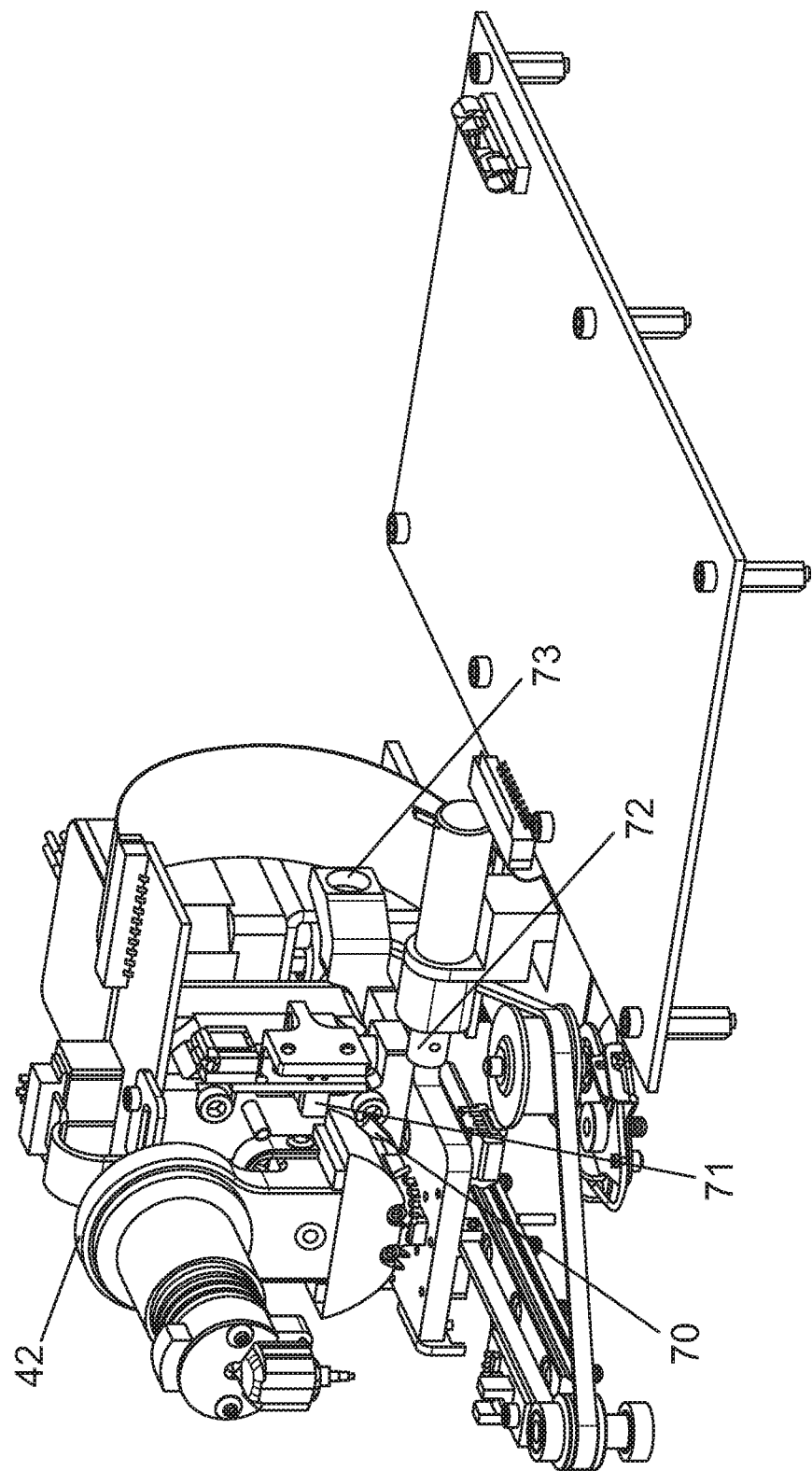
FIG. 27 depicts an exemplary robot assembly according to the present disclosure.
Figure 28:
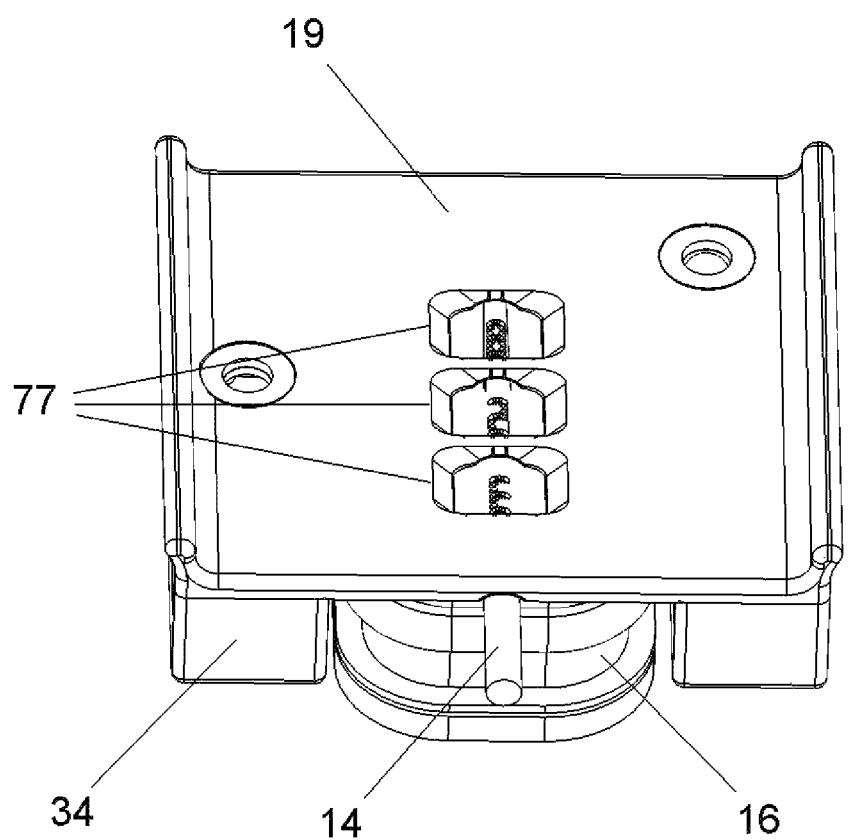
FIG. 28 depicts an exemplary body part plate assembly and spring-loaded tail plate assembly according to the present disclosure.
Figure 29:
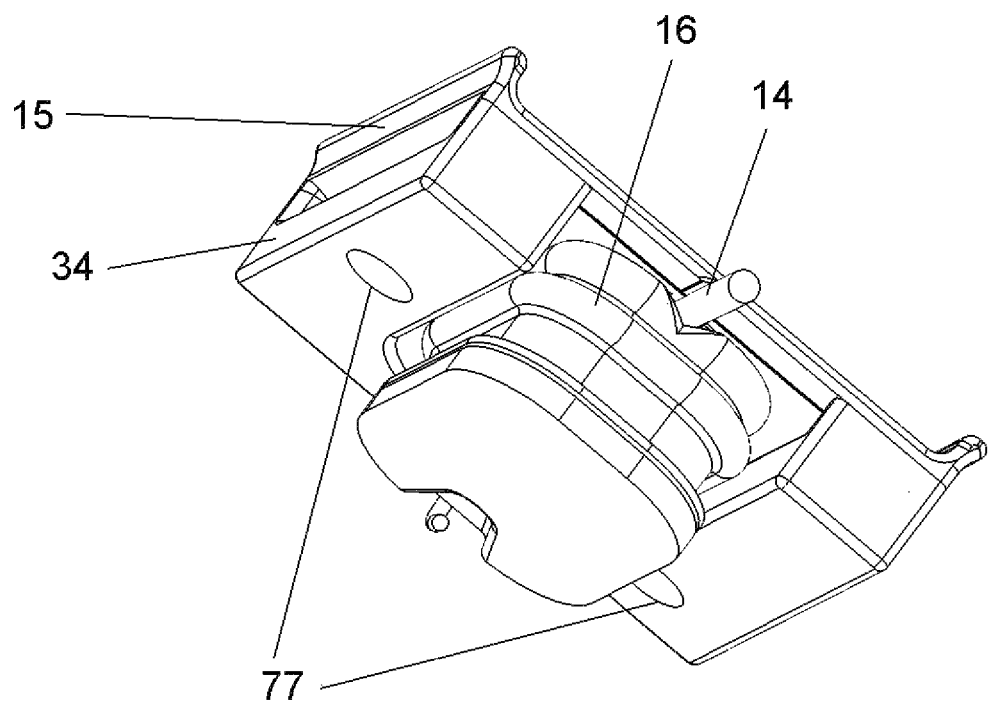
FIG. 29 depicts an exemplary a body part plate assembly and spring-loaded tails plate assembly according to the present disclosure.
Figure 30:
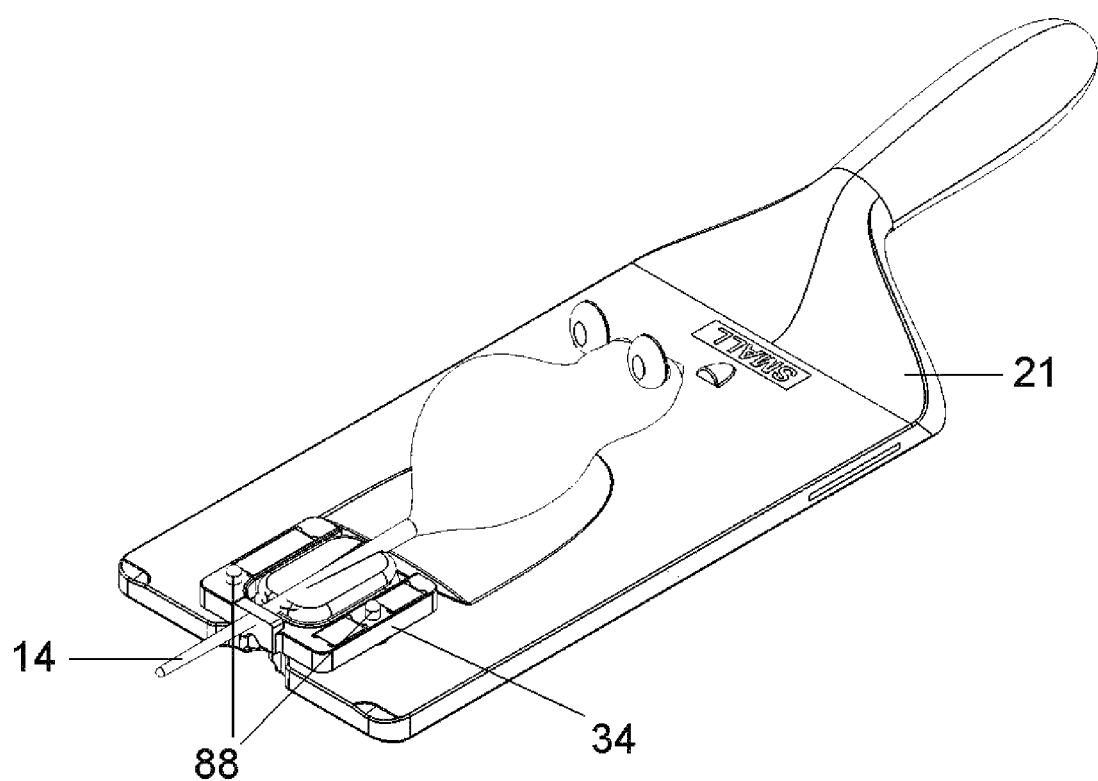
FIG. 30 depicts an exemplary restraining device according to the present disclosure.
Figure 31:
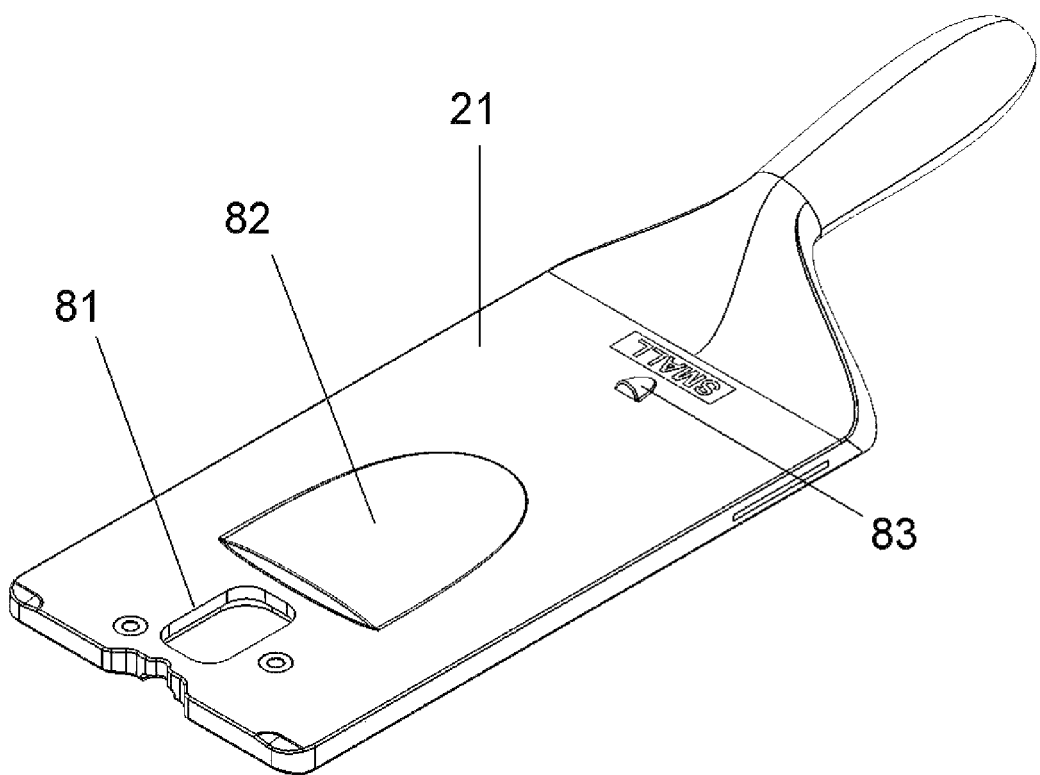
FIG. 31 depicts an exemplary baseplate according to the present disclosure.

In one embodiment, the robotic assembly 42 comprises at least a first actuator that actuates the marking device for marking a mark (e.g. R or Z axis), and further comprises at least a second actuator (e.g. X, Y, Z, Phi, or theta axis) for positioning the robotic arm (and marking device). Optionally, the first actuator(s) is/are connected between the robotic arm and the marking device. This configuration allows more rapid placement of the identification device (i.e. position and angle Φ with respect to the body part to be marked) as illustrated in FIG. 42B, more accurate and discrete marking, and/or less wear on the marking actuator (e.g. as depicted in FIG. 1 and FIG. 25). Such a robot assembly is optionally combined in a marking system with a body part restraint, such as a body part plate assembly. For example, such a robot assembly 42 is useful in combination with body part (e.g. tail) plate assembly 20 with conformative biasing means 46 and/or one or more operation windows 19.

In one embodiment, the robot assembly 42 comprises first and second actuators and the first actuator(s) actuates the marking device along the R or Z axis and the second actuator(s) actuates the marking device (and robotic arm) along the X, Y, Z, Phi, or theta axis. For example, the first actuator can actuate the marking device for making a mark along the R axis and the second device can actuator the marking device along the theta axis. Optionally, the first actuator comprises a servo motor (e.g. PID controlled) coupled to a piston (e.g. scotch yolk).

In one embodiment, the robot assembly 42 comprises first and second actuators and the first actuator(s) actuates the marking device along the X, Y, Z, or theta axis and the second actuator actuate(s) the marking device along the X, Y, Z, or theta axis.

In one embodiment, the robot assembly 42 comprises first, second, and third actuators and the first actuator(s) actuates the marking device along the R or Z axis, the second actuator(s) actuates the marking device (and robotic arm) along the X or theta axis, and the third actuator(s) actuates the marking device (and robotic arm) along the Y or Phi axis. Optionally, the first actuator comprises a servo motor (e.g. PID controlled) coupled to a piston (e.g. scotch yolk).

In some embodiments, as illustrated in FIGS. 42A-44 and 53, the actuator(s) of the robot assembly 42 are configured to deposit the microelectronic chip 300 into a cylindrical lumen, conical substrate or needle, 5b. To deposit the microelectronic chip, the inserter 5 is actuated to penetrate epidermis, and continues into the dermis of the marking substrate where the microelectronic chip 300 is deposited before the inserter returns.

To transfer the microelectronic chip 300 into the dermis with less load force on the inserters and less discomfort to the animal may require the use of sharp inserter tips 220. Depending on the number of tattoos produced or chips inserted, inserters may need to be replaced periodically. Inserters may also require replacement in those cases where cross-contamination between animal populations must be prevented and inserter sharing is not permissible. In other instances, if inserters become damaged (e.g. the tips become bent), they need to be replaced. Regardless of the reason behind the need to change inserters, it is preferred that the design be such that the replacement is easily done by the user of the pigment tattooing system. Most noteworthy however is that it is desirable that in making a inserter change, minimum compromise be made in the repeatability of the inserter tip length deviation and inserter tip concentration deviation with respect to the marking device, particularly if no closed-loop feedback relative to the inserter tip penetration and lateral positioning into the dermal layer is provided.

In order to repeatably position the inserter 5 during inserter replacement, the identification device 3 may include a inserter cartridge 92 to which the inserter 5 may in some embodiments be accurately coupled. Turning now to FIGS. 35-38, a non-limiting exemplary embodiment of the inserter cartridge 92 is illustrated, including a reference feature 93 configured to precisely mount the inserter cartridge 92 onto the marking device.

Figure 39:
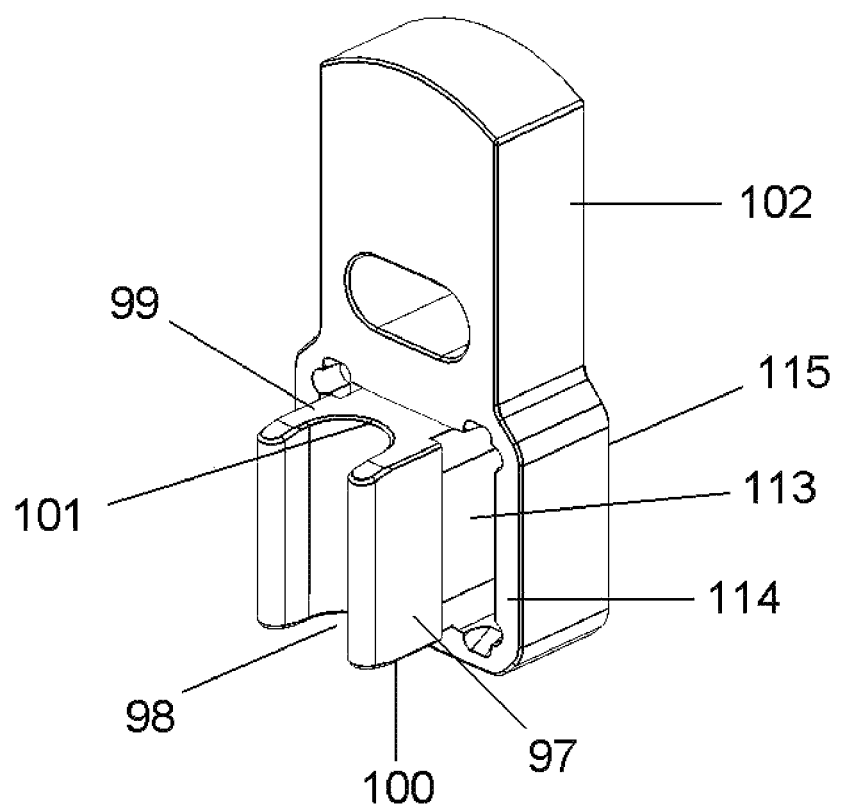
FIG. 39 depicts an exemplary mounting mechanism for the inserter cartridge according to the present disclosure.
Figure 40:
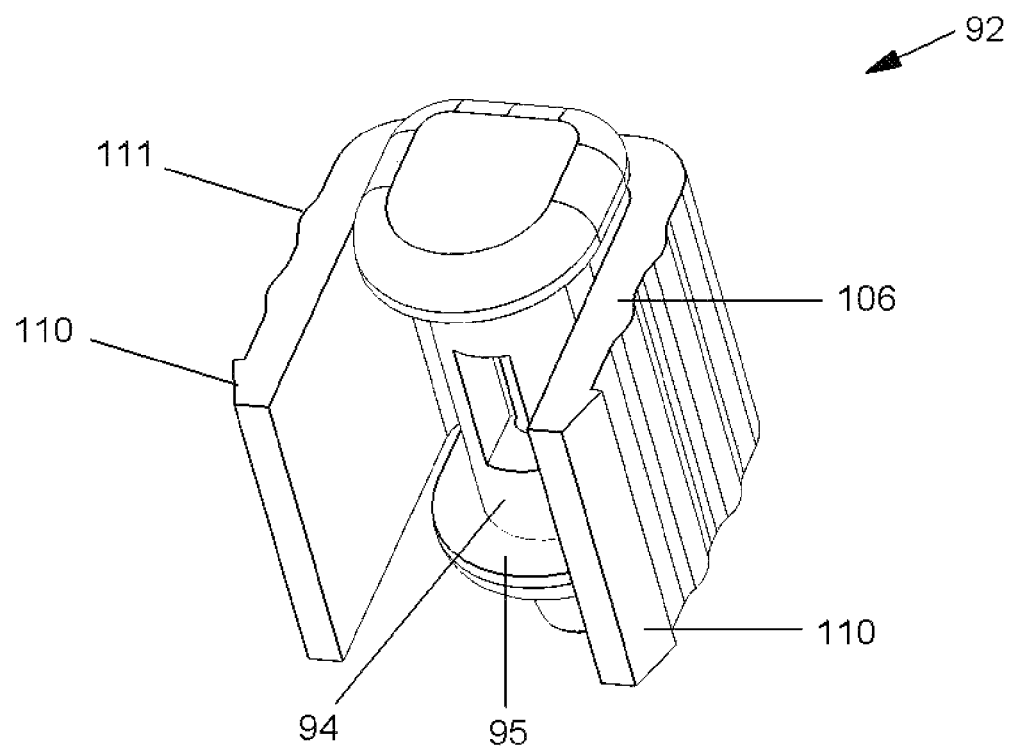
FIG. 40 depicts an exemplary inserter cartridge in rear perspective according to the present disclosure, particularly illustrating the locking feature.

As illustrated in FIGS. 35-38, the reference feature 93 of the inserter cartridge 92 includes a locating cylinder 94 having a cylindrical surface that is at least partially exposed. The locating cylinder 94 extends between two end plates (95, 96). As illustrated in FIG. 39, the inserter cartridge 92 may be mounted to the identification device 3 through a docking member 97 that is coupled to a scotch yoke 102 of the identification device 3. The docking member 97 defines a receiving slot 98 extending between a top surface 99 and a bottom surface 100.

To mount the inserter cartridge 92, the locating cylinder 94 is inserted into the receiving slot 98 of the docking member 97 until its cylindrical surface conformingly engages a terminal end 101 of the receiving slot 98. With the locating cylinder 94 in place, the two end plates (95, 96) also conformingly engage the top and bottom surfaces (99, 100) of the docking member 97, thereby completely fixing the position of the inserter cartridge on the docking member. As a result, if the inserter cartridge 92 needs to be replaced during a marking process, the replacement inserter cartridge can be precisely mounted in the same position for continued marking without significantly affecting the consistency and overall quality of the marks produced.

In a refinement, the locating cylinder 94 may also provided housing to the inserter 5. For example, the locating cylinder 94 may include a center bore in which the inserter 5 may be positioned using fixturing and fixed into place using an adhesive such as an epoxy.

Alternatively, the inserters 5 may in some embodiments be positioned and fixed in place by molding the locating cylinder 94 about the inserter 5. This can be achieved according to known processes in the injection molding industry where threads, pins, and even inserters are inserted into a mold cavity and a surrounding housing is injection molded into place.

In addition to the reference feature 93 described above, the inserter cartridge 92 may further include a locking feature 105 configured to lock the inserter cartridge 92 onto the identification device 3. Still referring to FIGS. 35-38, the locking features 105 of the inserter cartridge 92 may include a locking clip 106 having a flexible U-shaped sidewall 107 extending between two ends (108, 109). Each of the two ends (108, 109) includes at least one outwardly protruding locking teeth 110. The locking clip 106 further includes a plurality of optional gripping ribs 111 disposed on an exterior surface 112 of the U-shaped sidewall 107.

To lock the inserter cartridge 92, the scotch yoke 102 of the identification device 3 includes a receiving opening 113 extending between front and back surfaces (114, 115), as illustrated in FIG. 39. When the reference feature 93 of the inserter cartridge 92 is received in the docking member 97, the locking tooth 110 is pressed toward each other as they are inserted through the receiving opening 113 of the scotch yoke 102. The inserter cartridge 92 is dimensioned so that the locking teeth 110 of the locking clip 106 clears the back surface 115 of the receiving opening 113 when the locating cylinder 94 is conformingly received in the receiving slot 98 of the docking member 97. Due to the outward biasing force of the locking clip 106, the locking tooth 110 remains firmly engaged to the back surface 115 of the receiving opening 113, thereby locking the inserter cartridge 92 onto the identification device 3.

One feature of the disclosed marking system is deposition of pigment with improved depth precision, such as by using the restraining device 2 and/or identification device 3 disclosed herein. For purposes of tattooing a mouse tail, the identification device 3 may need to drive the inserter 5 to the desired dermal layer depth, for example, 150-250 microns for young mice, and 200-300 microns for adult mice.

In one embodiment, the marking system comprises inserters that are capable of penetrating the marking substrate epidermis and transfer the pigment from the inserter into the dermal layer.

In one embodiment, the marking system is configured to deposit a pigment into the marking substrate at a depth of;
a. 150-250 microns for young mice.
b. 200-300 microns for adult mice.
c. 200-250 microns regardless of the age of the mice.

To meet this depth requirement and to produce a mark of sufficient font size to be legible to the unaided eye, the mark character must partially wrap the circumference of the tail and be at the target depth. This latter circumferential depth requirement may in some embodiments be achieved by pivoting the inserter 5 during the tattooing process about an arc whose center is coincident with the center of the mouse tail diameter, thus keeping the identification device normal to the surface of tail at all times. Maintaining the tattoo depth therefore is attained by programming the system processor to control the position of the robotic assembly 42 (whereon is attached the inserter 5), and providing a mounted inserter having a length controlled to ±25 microns and lateral centering within ±125 microns with respect to its pivoting axis.

It is conceivable that an inserter cartridge 92 can in some embodiments be alternatively designed to mount directly to the identification device 3 and forego the reference and/or locating features (93, 105). This configuration can be suitable and sufficient for low-volume tattooing requirements.

In the case of high-volume throughput requirements, it may be desirable to design a system wherein multiple inserter housings are mounted into, for example, a turret, which the marking system can in some embodiments access in order to replace inserters upon command, or on a pre-programmed basis.

Restraining Device

The restraining device, useful according to the present disclosure, is any device that can restrain the body part of an animal to be marked. For example, in one embodiment the restraining device has a first part useful for restraining the main body of the animal, and a second part useful for restraining and presenting the body part to be marked to the identification device. Useful restraining devices include those that do not kill, harm, or cause undue duress or stress to the animal. Further useful features of the restraining device include said device's ability to compensate for variations in taper, girth, and/or other abnormalities of the tail.

In one embodiment, the marking system comprises one restraining device having a spring-loaded tapered v-groove to support the underside of the tail during marking and that is used to compensate for differences in size of the substrate body part while still enabling the marking system to maintain the target pigment depth of the marking.

In one embodiment, the marking system comprises a plurality of restraining devices each having a spring-loaded tapered v-groove of varying size to support the underside of the tail during marking and that are used to compensate for the range of differences in size of the substrate body part while still enabling the marking system to maintain the target pigment depth of the marking.

In one embodiment, the restraining device is comprised of a one-piece spring-loaded plate having a tapered v-groove supporting the substrate body part.

Optionally, the one-piece spring-loaded tapered v-groove plate is additionally enclosed within a protective compliant boot.

In one embodiment, the restraining device is comprised of a modulated spring-loaded plate that includes multiple independently articulating self-aligning spring-loaded, tapered v-groove sections, the combination of which comprise the tapered v-groove plate supporting the substrate body part.

Optionally, the multiple spring-loaded tapered v-groove sections are additionally enclosed within a protective compliant boot.

Figure 8:
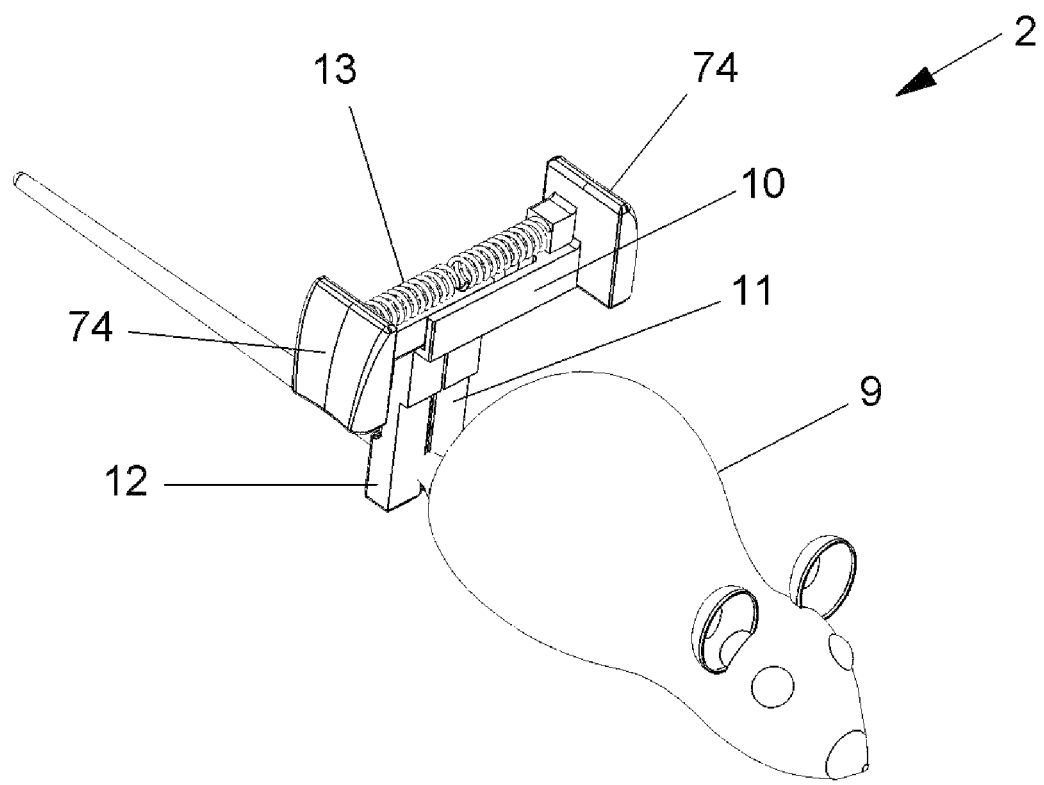
FIG. 8 depicts an exemplary restraining device according to the present disclosure.

Turning now to non-limiting examples of the restraining device 2, and with particular reference to FIG. 8, which illustrates a restraining device 2 that utilizes a body part cleat 10 that may in some embodiments provide rapid and secure immobilization of an animal or body part thereof. The body part (e.g. tail) cleat 10 includes opposing members 11 and 12. The body part cleat 10 further includes a biasing member 13, such as a spring, that biases the opposing members 11, 12 against each other, thereby restraining the body part (e.g. tail) from longitudinal or Y axis movement, when the body part is inserted and secured between the opposing members 11, 12. As illustrated, the body part cleat 10 in one embodiment is positioned proximal to the trunk of a mouse.

As illustrated in FIG. 8, the body part cleat 10 may in some embodiments include finger tabs 74 such that the user loads and releases the body part with a single hand and in a single motion. Although the body part cleat 10 is depicted has having opposing members 11, 12 which slide about each other (a sliding cleat), the body part cleat can alternatively be provided in other configurations (e.g. as described herein).

Figure 9:
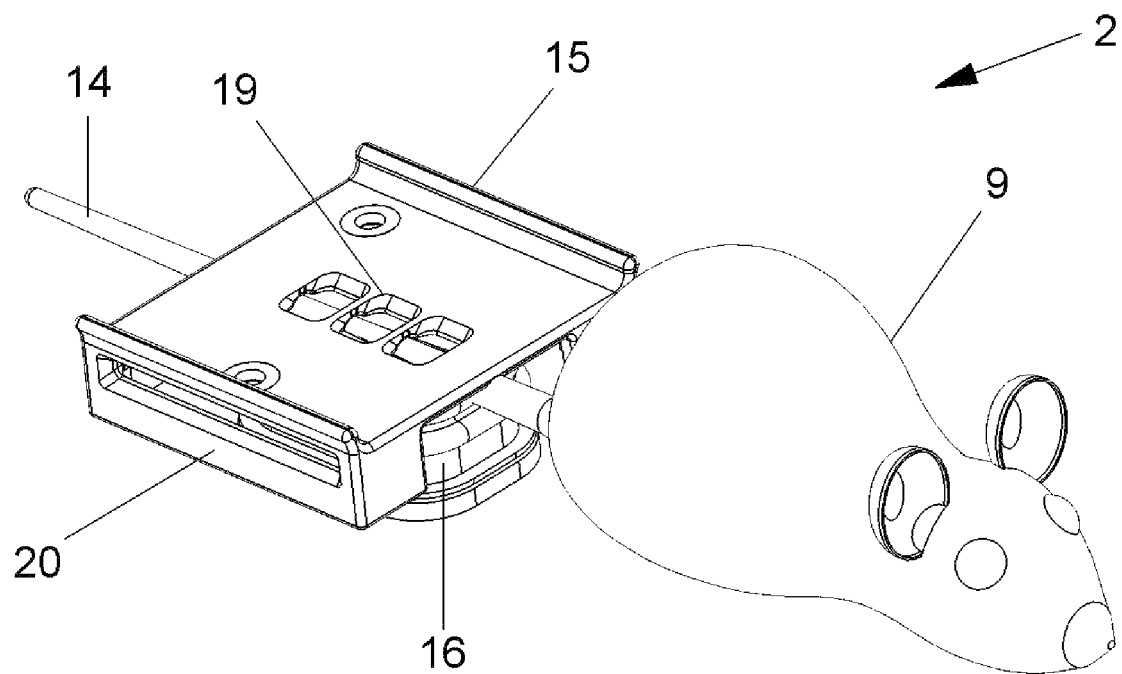
FIG. 9 depicts an exemplary body part plate assembly according to the present disclosure.
Figure 10:
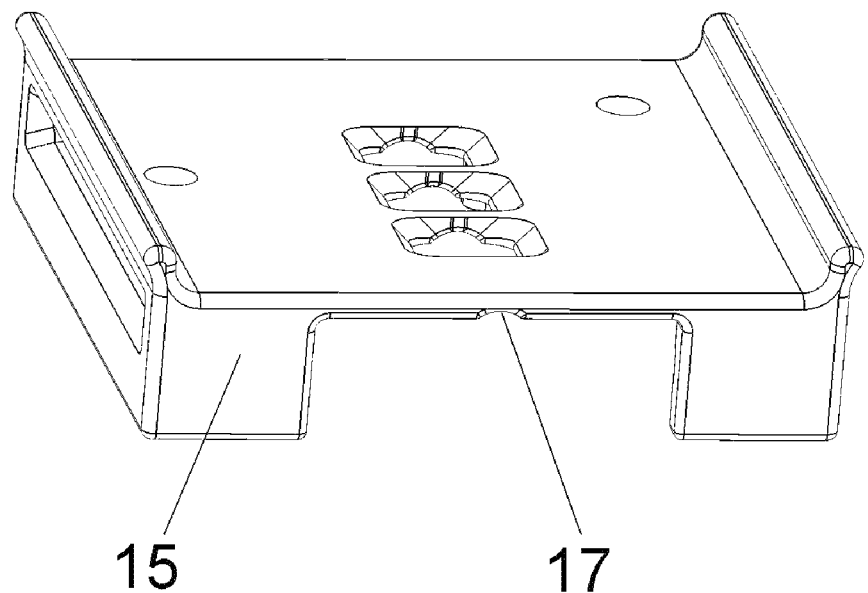
FIG. 10 depicts an exemplary body part plate according to the present disclosure.
Figure 11:
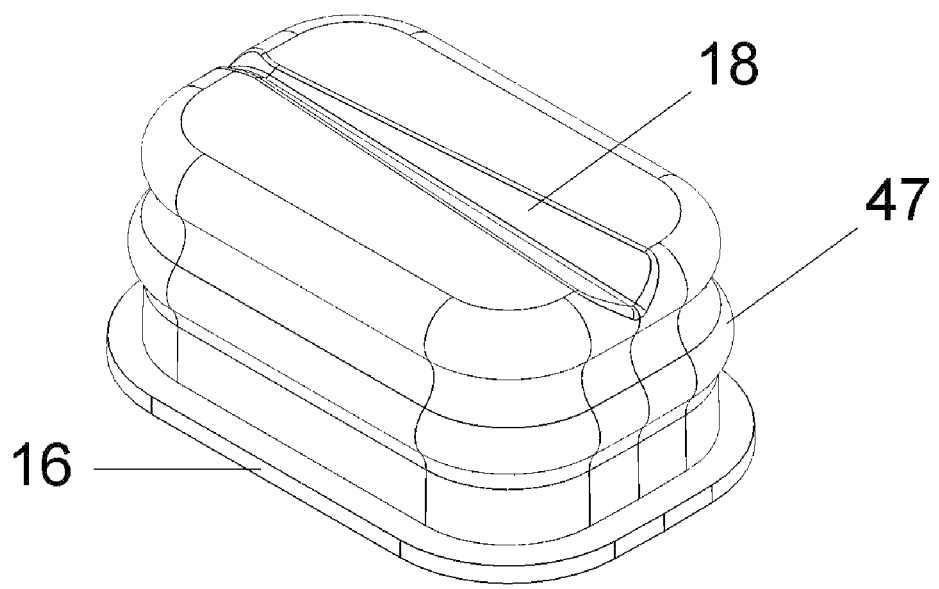
FIG. 11 depicts an exemplary protective compliant boot according to the present disclosure.

Referring now to FIGS. 9-11, the restraining device 2 may in some embodiments include a body part plate assembly 20 that may in some embodiments provide rapid and secure immobilization of an animal or body part thereof. As illustrated, the plate assembly 20 includes a top plate 15 and an adjustable (e.g. spring-loaded) bottom plate assembly 16, which cooperate with each other to precisely orient the top surface of the marking substrate (e.g. tail or other body part) relative to the identification device 3. For example, the top surface of the marking substrate may be secured between the top plate 15 and the adjustable bottom plate assembly 16 in a horizontal position (or at a desired angle or along a desired axis or other orientation).

In a refinement, the top plate 15 may also be adjustable. For example, adjustment of the final angle or orientation of the top surface of the marking substrate may in some embodiments be achieved by adjusting the angle of top plate 15.

Figure 24:
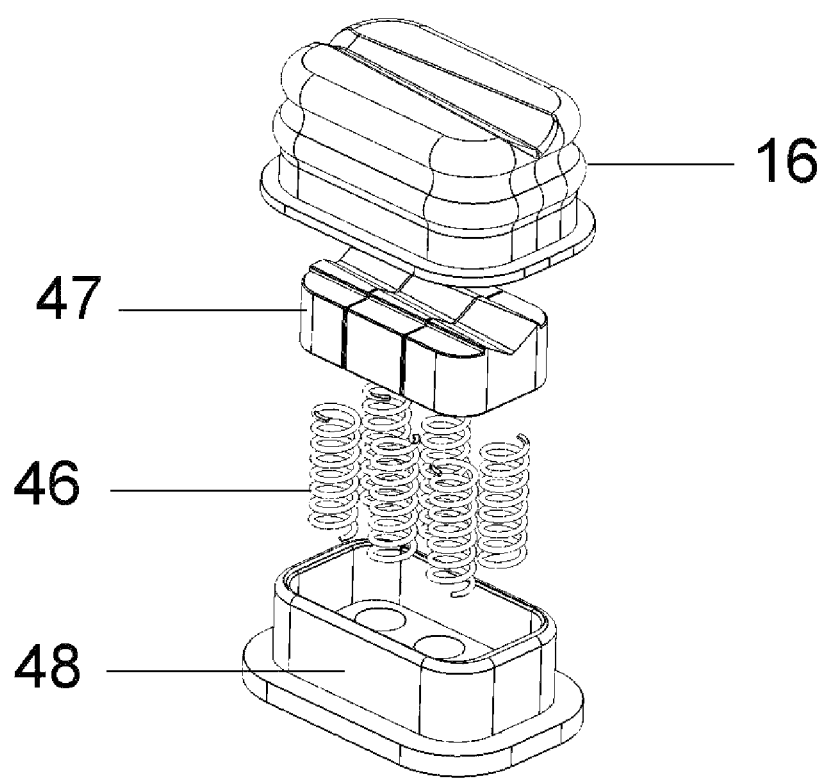
FIG. 24 depicts an exploded view of an exemplary spring loaded tail plate according to the present disclosure.
Figure 33:
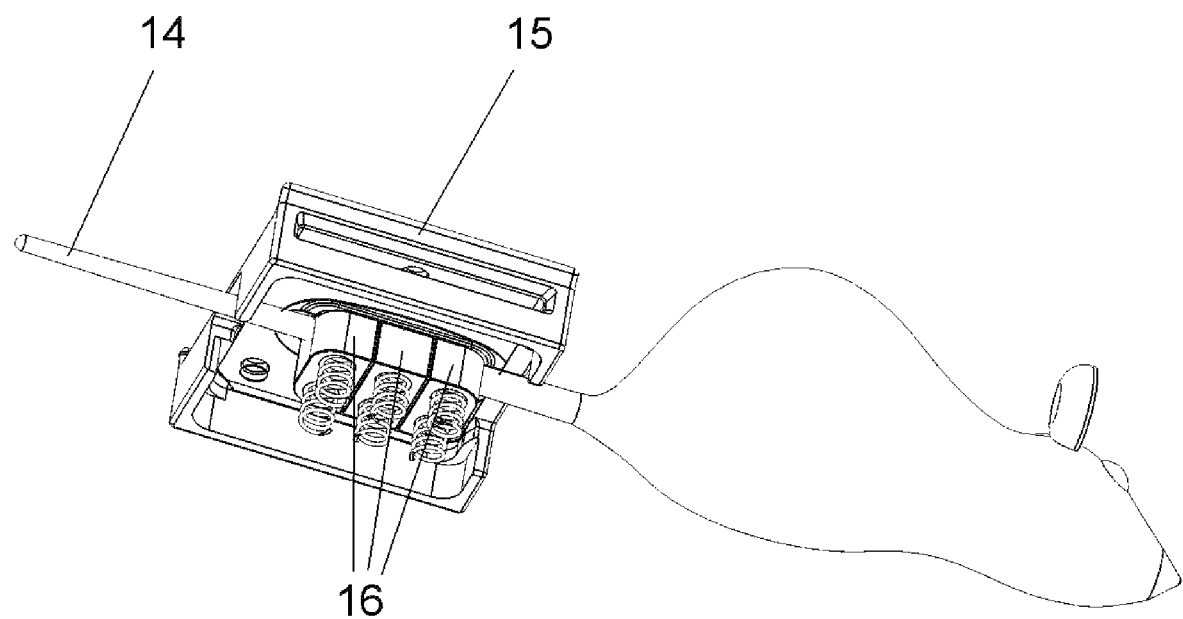
FIG. 33 depicts an exemplary body part plate assembly according to the present disclosure.

Turning now to the exploded view of FIG. 24, the adjustable bottom plate assembly 16 includes a bottom plate 47 and biasing means 46, such as springs or other conformative biasing means or other elastic-biasing means, for example, to press the bottom plate 47 (with marking substrate supported therein) against the top plate 15, as depicted in FIG. 9 and FIG. 33. When using conformative biasing means such as springs 46 (e.g. under all four corners of plate 47), the spring loaded bottom plate 47 conforms to the angle of the bottom surface of the marking substrate as it opposes the top plate 15, as depicted in FIG. 33. As depicted in FIG. 24, the adjustable bottom plate assembly 16 in some embodiments optionally includes a mount 48 for support and/or include a boot 49 (e.g. made of rubber or other non-rigid material) to translate the motion of the bottom plate 47 without exposing the underlying mechanism (e.g. the bottom plate 47 and the biasing means 46) to dirt and debris, allowing easier cleaning and reducing contamination.

Turning now to FIGS. 10-11, the top plate 15 may include operation window(s) 19 to allow the operator and/or the identification device 3 to access the marking substrate or other restrained body part while holding its position. As illustrate in FIG. 11, in the case of a conical (or other tapered) marking substrate such as a tail, the spring loaded bottom plate 47 can be provided with a tapering v-groove 18, e.g., at an angle of 90 degrees or greater, to center various cone diameters. In a further embodiment illustrated in FIG. 10, the top plate may also include a radial groove 17 large enough to accommodate the largest conical body part that will be restrained. It is contemplated that these opposing features (v-groove 18 of spring-loaded tail plate 16 and radial groove 17 of top plate 15) may cooperatively center the marking substrate along the longitudinal axis of the v-groove 18 and radial groove 17 while secure the marking substrate evenly between the top plate 15 and bottom plate 47. In one embodiment, marks made on a marking substrate restrained by such a body part plate assembly 20 have improved precision, for example, because the plate assembly 20 restrains the substrate portion of the body part such as tail 14 from movement along the X, Z, and/or R axes.

Figure 45:
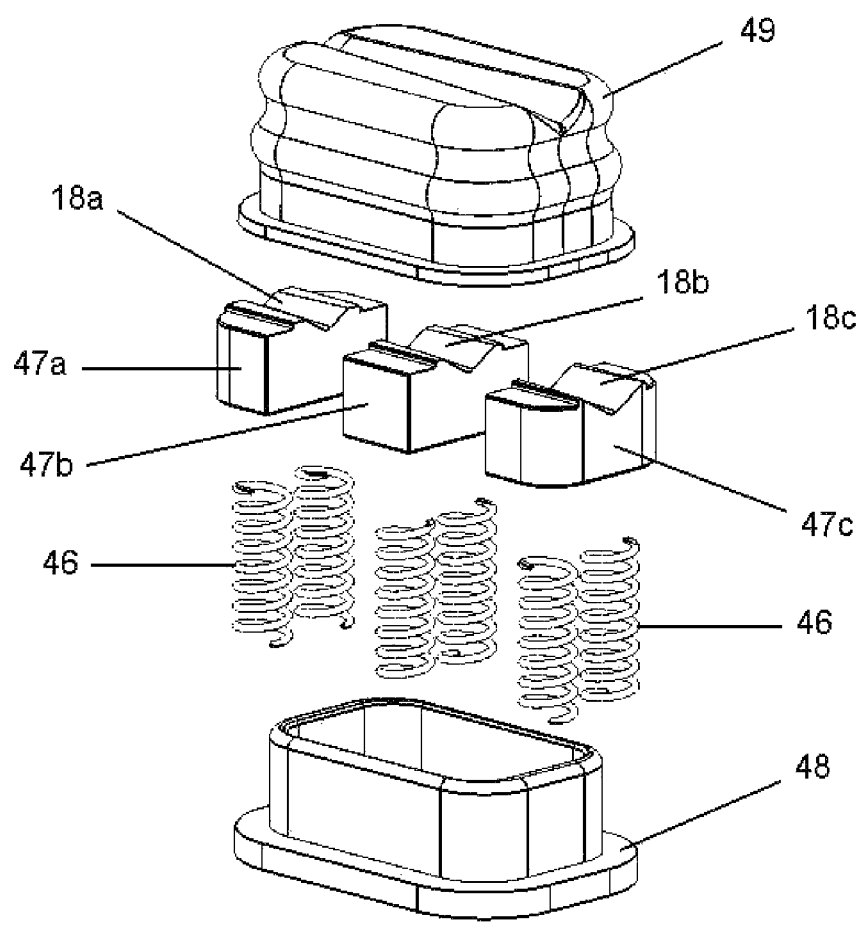
FIG. 45 depicts an exploded view of an exemplary spring-loaded tail bed particular to the restraining device comprising modulated tail plate to accommodating the size of the marking substrate according to the present disclosure.

In another embodiment, the bottom plate 47 and the tapered v-groove 18 formed thereon may be modulated to further enhance the security and precision provided by the body part plate assembly 20. Referring now to FIGS. 45-48, the modulated bottom plate 47 includes a plurality of bottom plate sections each including a section of the tapering v-groove 18. As illustrated in FIG. 45, the modulated bottom plate 47 includes three bottom plate sections (47a, 47b, 47c). Each of those sections includes a section of the tapering v-groove 18 (18a, 18b, 18c, respectively). It is to be understood that the number of bottom plate sections may be dependent on the nature of the marking substrate, the dimension of the of the body part plate assembly 20, and should not be limited to the non-limiting examples illustrated in FIGS. 45-48. For example, the bottom plate 47 may include two or more than three bottom plate sections in other embodiments of the present disclosure.

Figure 46:
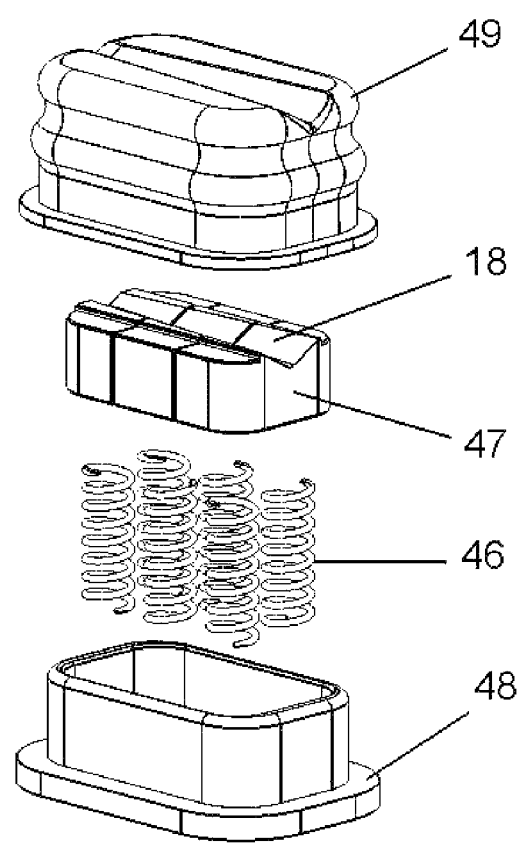
FIG. 46 depicts an exploded view of an exemplary spring-loaded tail bed particular to the restraining device comprising modulated tail plate to accommodating the size of the marking substrate according to the present disclosure, particularly illustrating the modulated tail plate assembled together.
Figure 47:
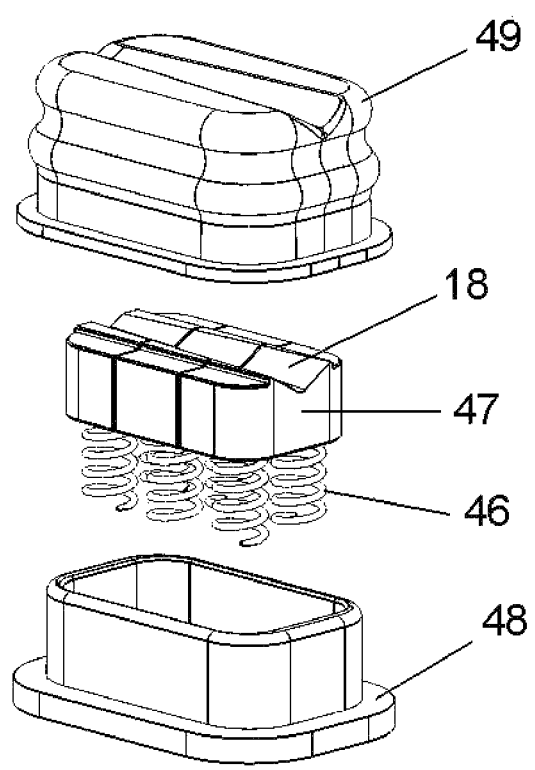
FIG. 47 depicts an exploded view of an exemplary spring-loaded tail bed particular to the restraining device comprising modulated tail plate to accommodating the size of the marking substrate according to the present disclosure, particularly illustrating the modulated tail plate assembled together with springs.
Figure 48:
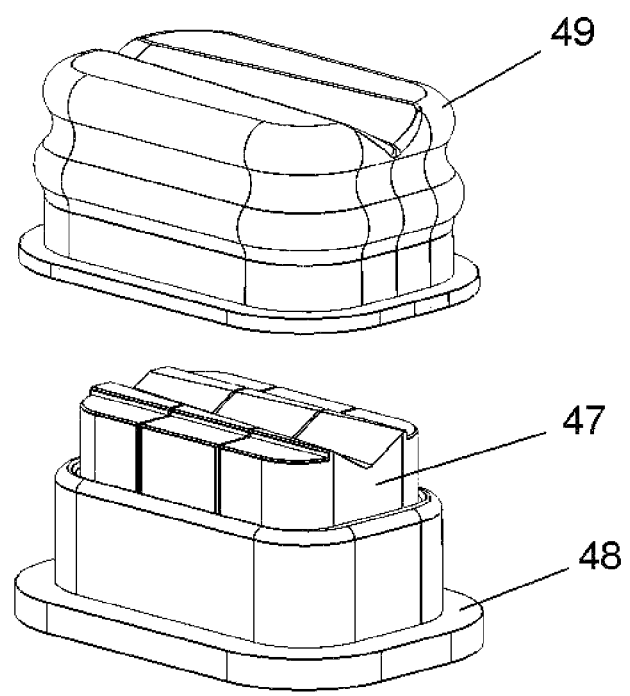
FIG. 48 depicts a perspective view of an exemplary spring-loaded tail bed particular to the restraining device comprising modulated tail plate to accommodating the size of the marking substrate according to the present disclosure, particularly illustrating the modulated tail plate assembled in the tail plate base.

Still referring to FIG. 45, each of the bottom plate sections (47a, 47b, 47c) may be provided with biasing means (46a, 46b, 46c), such as springs or other conformative biasing means or other elastic-biasing means. Such a modulated configuration allows each of the tapering v-groove sections (18a, 18b, 18c) to be independently articulating and self-aligning, thereby further enhancing the security and precision provided by the body part plate assembly 20. As illustrated in FIGS. 46-48, the modulated bottom plate 47 in some embodiments may be assembled in a mount 48 for support. Moreover, the modulated bottom plate 47 in some embodiments may include a boot 49 (e.g. made of rubber or other non-rigid material) to translate the motion of the bottom plate sections (47a, 47b, 47c) without exposing the underlying mechanism (e.g. the modulated bottom plate 47 and the biasing means 46) to dirt and debris, allowing easier cleaning and reducing contamination.

Figure 21A:
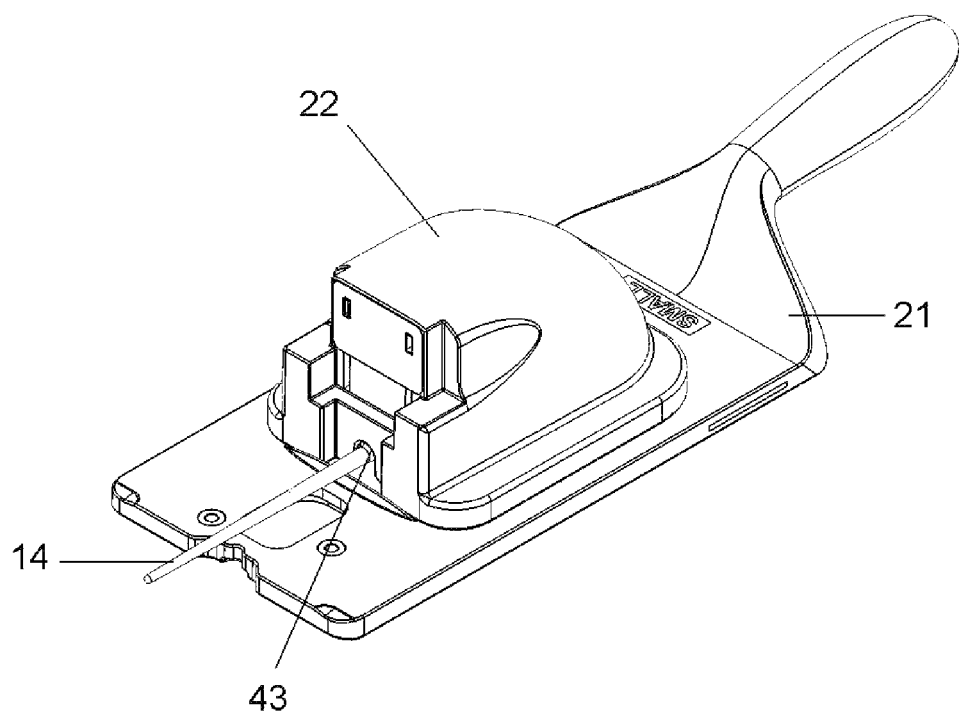
FIG. 21A depicts an exemplary restraining device according to the present disclosure.
Figure 21B:
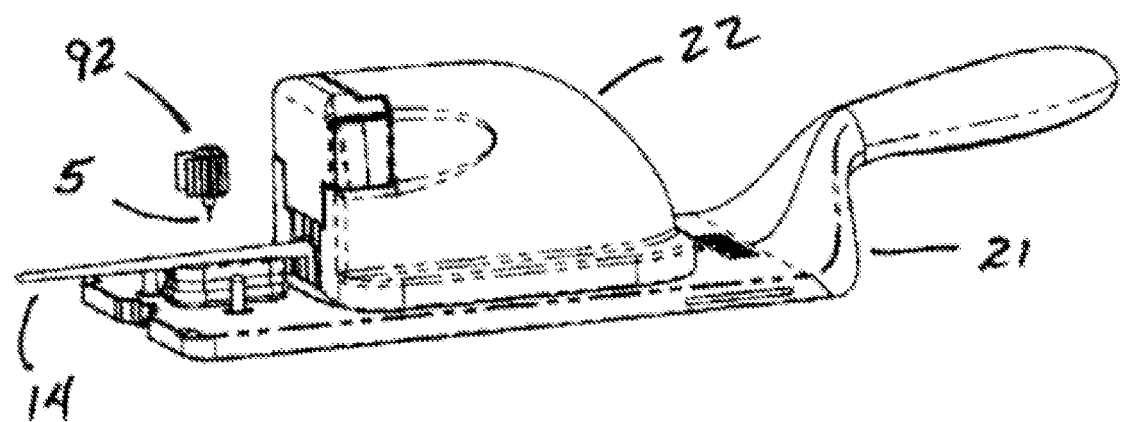
FIG. 21B depicts an exemplary orientation of the pigment marking needle tips used with the restraining device of FIG. 21A according to the present disclosure.
Figure 22:
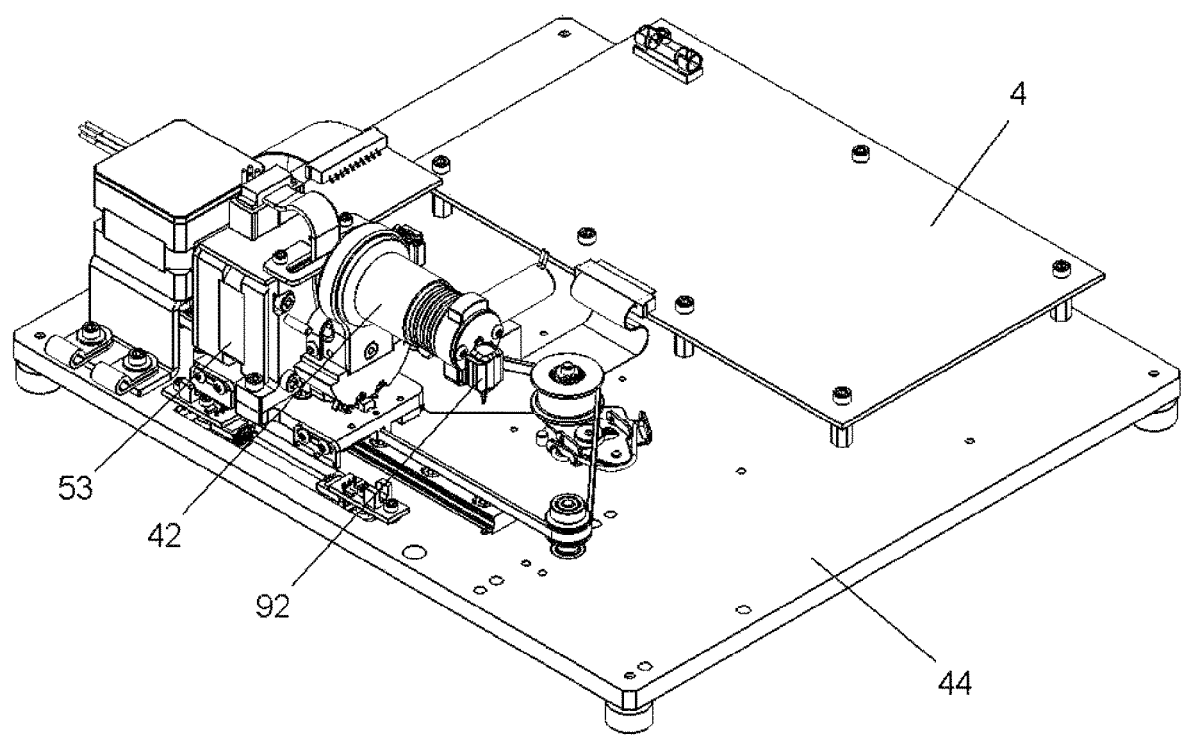
FIG. 22 depicts an exemplary robot assembly and controller according to the present disclosure.

Referring now to FIGS. 21A & 21B the restraining device may in some embodiments also utilize a body restraint 22 to further secure the animal. The body restraint 22 may in some embodiments be provided on a support, such as a baseplate 21. The body restraint 22 is sized to house an animal (or abdominal portion thereof) and comprises a body part port 43 sized to allow a body part comprising the substrate (e.g. tail) to be withdrawn from the body restraint 22 while the trunk of the animal remains in the body restraint 22.

The body restraint 22 in some embodiments is configured in any shape or size that restrains the trunk of the animal, prevents the animal from swiveling its head to harm (e.g. bite) itself, and/or prevents the animal from contorting or pivoting about its body part (e.g. tail). The restraint in some embodiments further comprise reversible fixing means such as magnets for securing the restraint to a baseplate or other surface such as a lab bench (e.g. stainless steel table top).

It will also be noted that the body restraint and the body part port position the animal tail in the proper orientation for the pigment marking needle.

Figure 34:
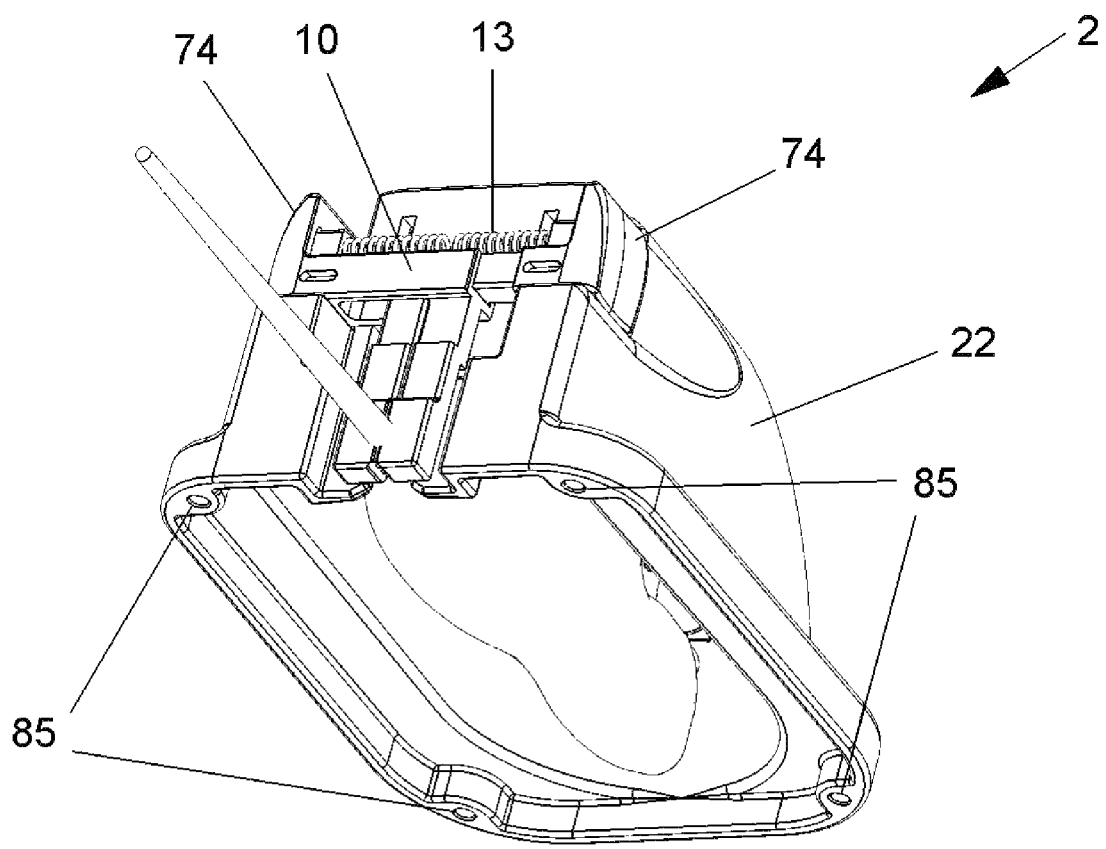
FIG. 34 depicts an exemplary restraining device comprising a body restraint and a body part restraint according to the present disclosure.
Figure 35:
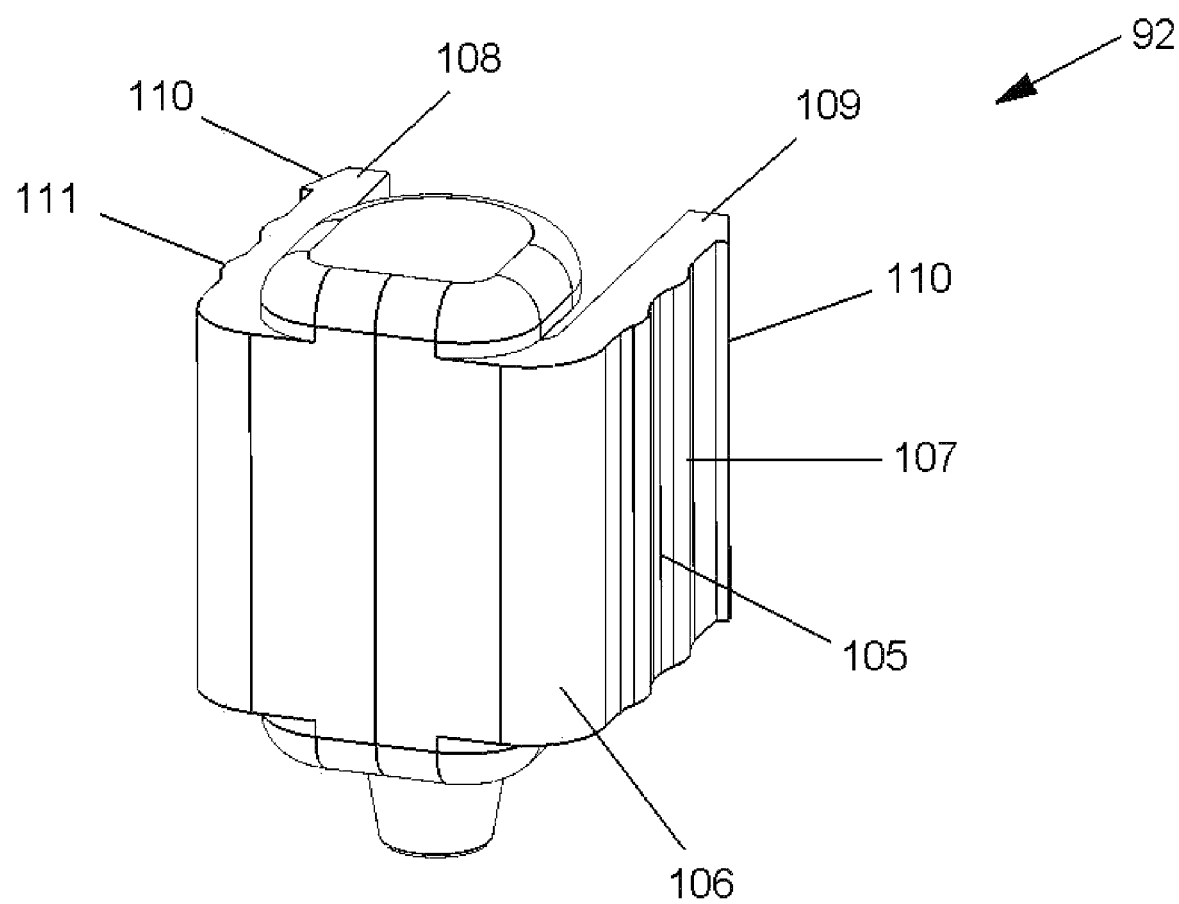
FIG. 35 depicts an exemplary inserter cartridge in front perspective view according to the present disclosure.
Figure 36:
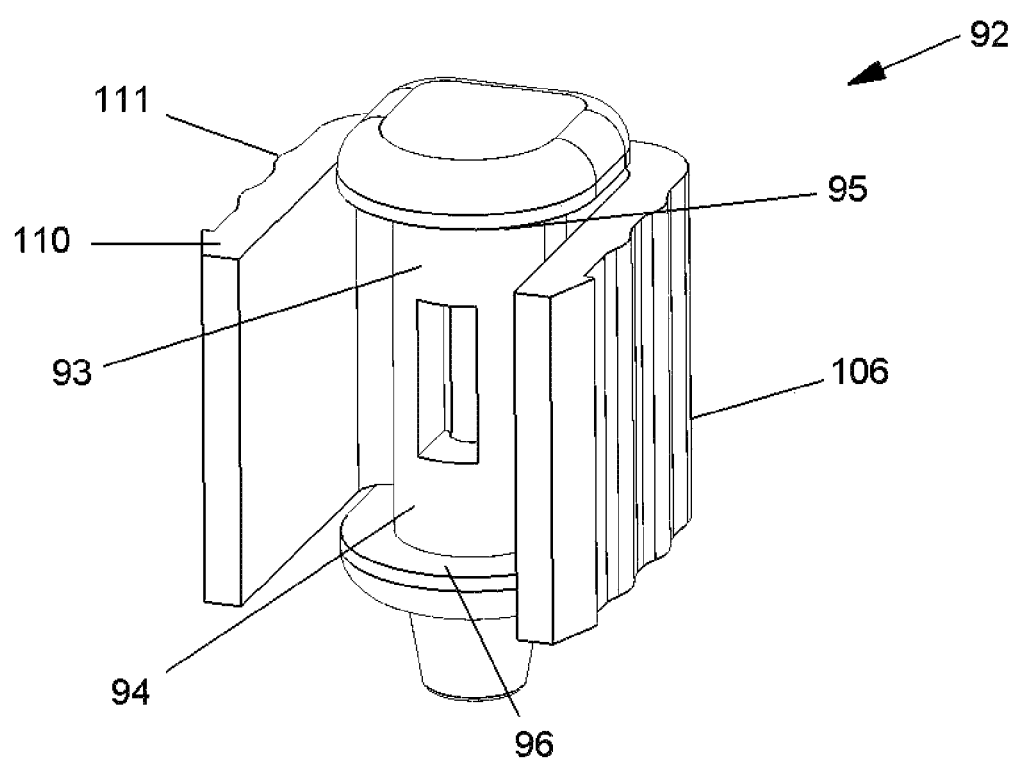
FIG. 36 depicts an exemplary inserter cartridge in back perspective view according to the present disclosure.
Figure 37:
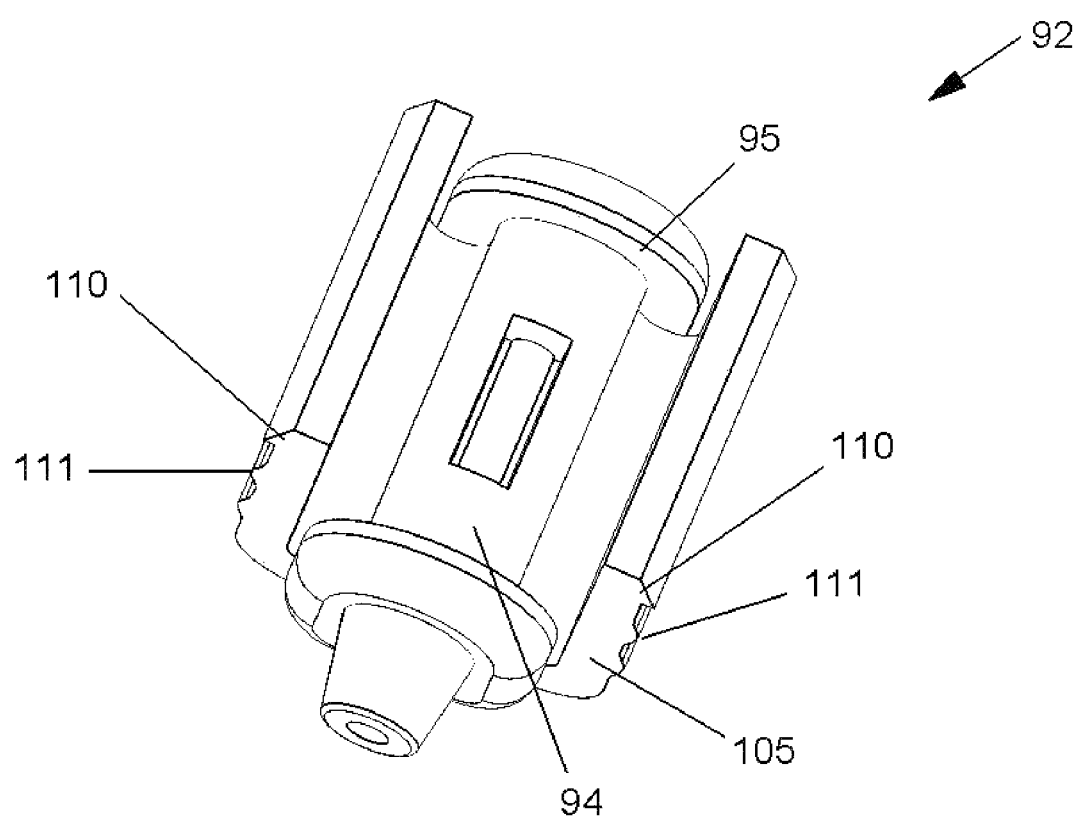
FIG. 37 depicts an exemplary inserter cartridge in rear perspective according to the present disclosure, particularly illustrating the upper reference feature.
Figure 38:
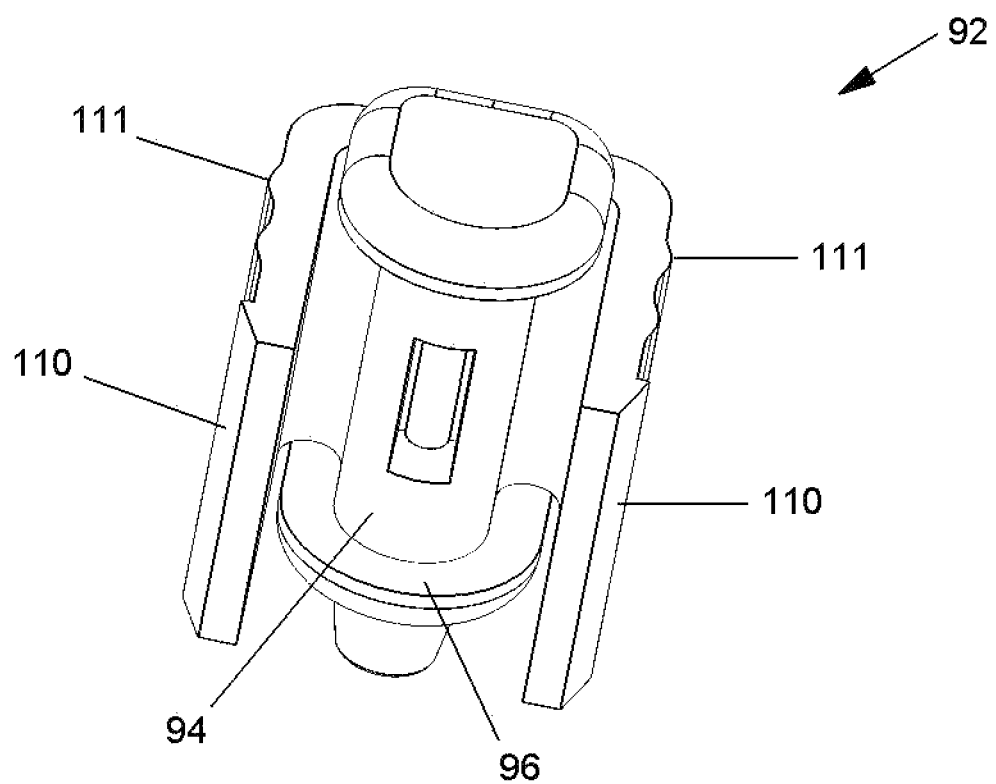
FIG. 38 depicts an exemplary inserter cartridge in rear perspective according to the present disclosure, particularly illustrating the lower reference feature.

Turning now to FIG. 34, the restraining device 2 may in some embodiments include a body restraint 22 and a body part cleat 10.

Figure 32:
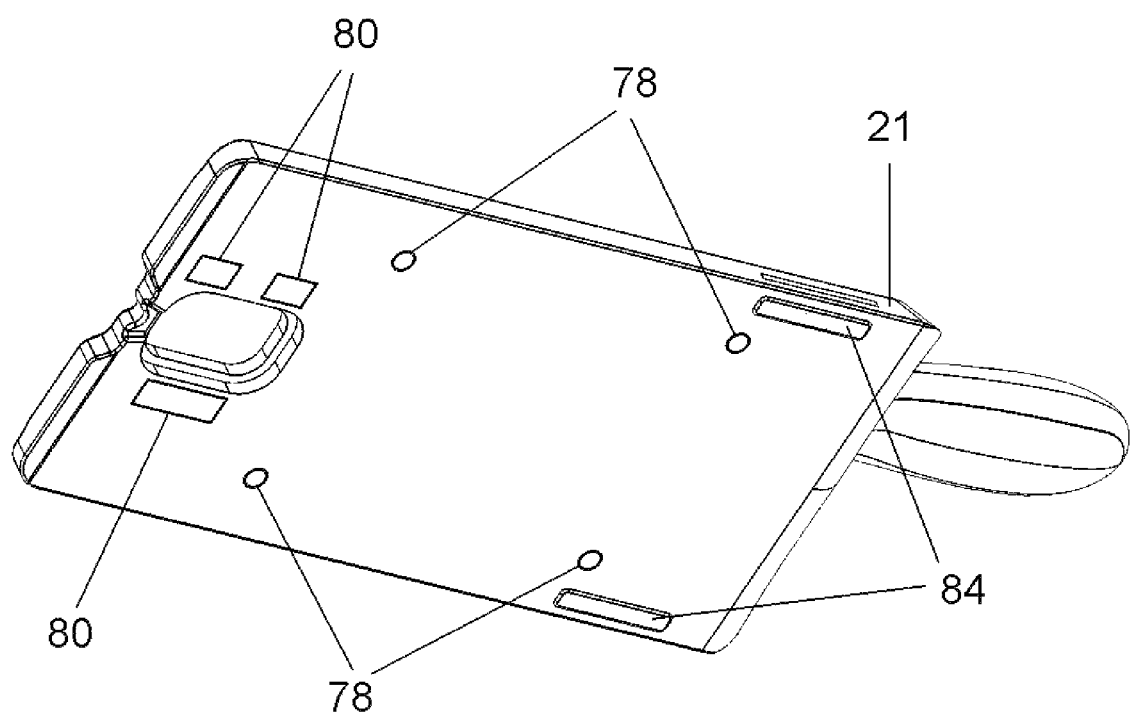
FIG. 32 depicts an exemplary baseplate according to the present disclosure.

FIG. 34 depicts a useful restraining device 2 of the present invention. In one embodiment, the body restraint 22 comprises reversible fixing means such as magnets 85. For example, magnets 85 can be secured to a metal table top, or can be specifically patterned to correspond to a pattern of magnets 78 on a baseplate 21, as depicted in FIG. 32.

The body part cleat 10 may in some embodiments be fixed to the body restraint 22 such that the user can hold the entire restraining device in one hand with fingers (e.g. a thumb and an index finger) depressing tabs 74 of the body part cleat 10 to separate opposing members 11, 12 from each other. The user can then simultaneously restrain both trunk and the body part (e.g. tail) of the animal (e.g. mouse) simply by placing the restraining device over the animal such that the body part is positioned between opposing members 11, 12, and then releasing his fingers from tabs 74.

In one embodiment, such a restraining device 2 optionally provides rapid but secure immobilization of an animal. In one embodiment, such a configuration allows a user to operate a second restraining device with a second hand, to simultaneously restrain two animals.

Figure 12:
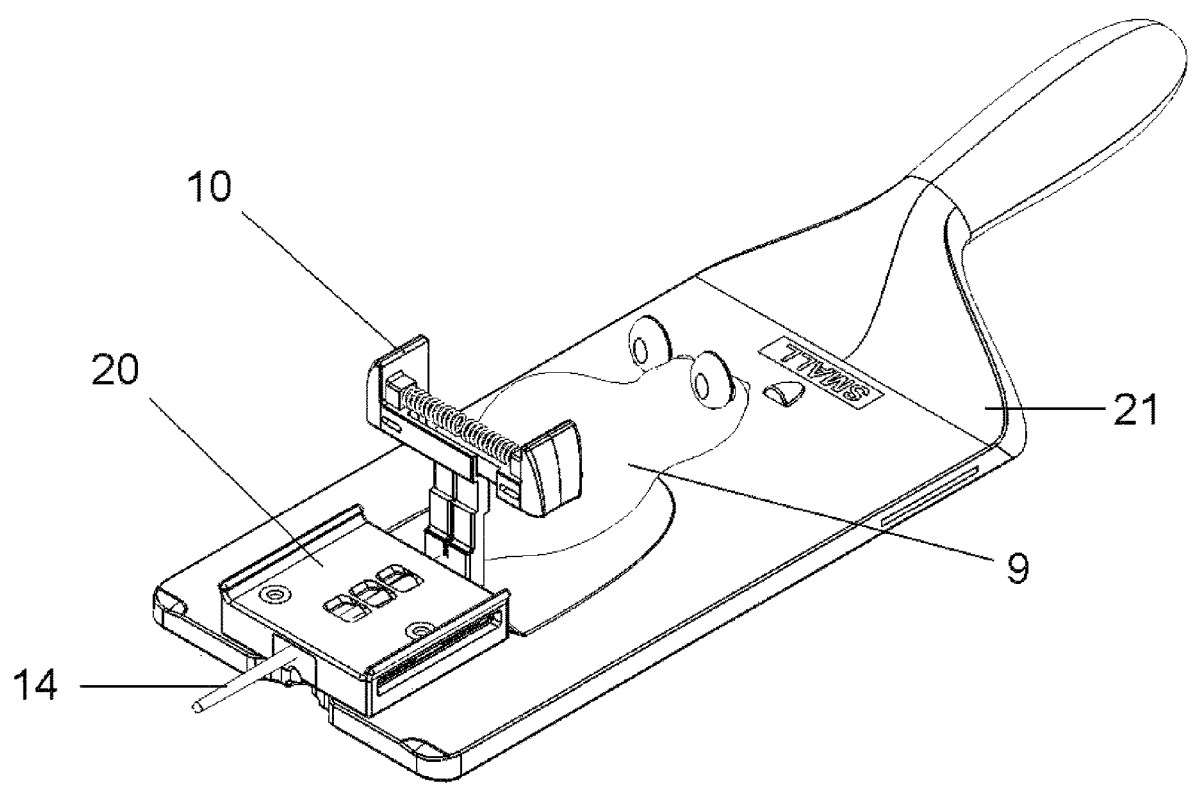
FIG. 12 depicts an exemplary restraining device according to the present disclosure.
Figure 13:
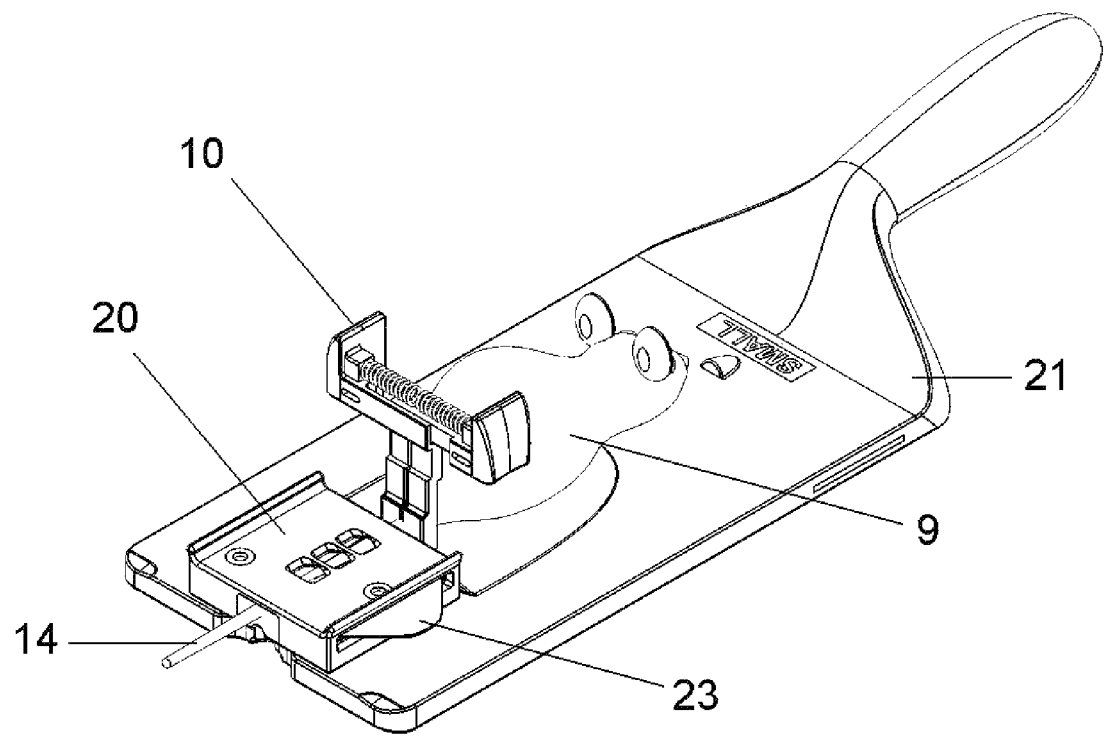
FIG. 13 depicts an exemplary restraining device and an exemplary media transfer assembly according to the present disclosure.
Figure 14:
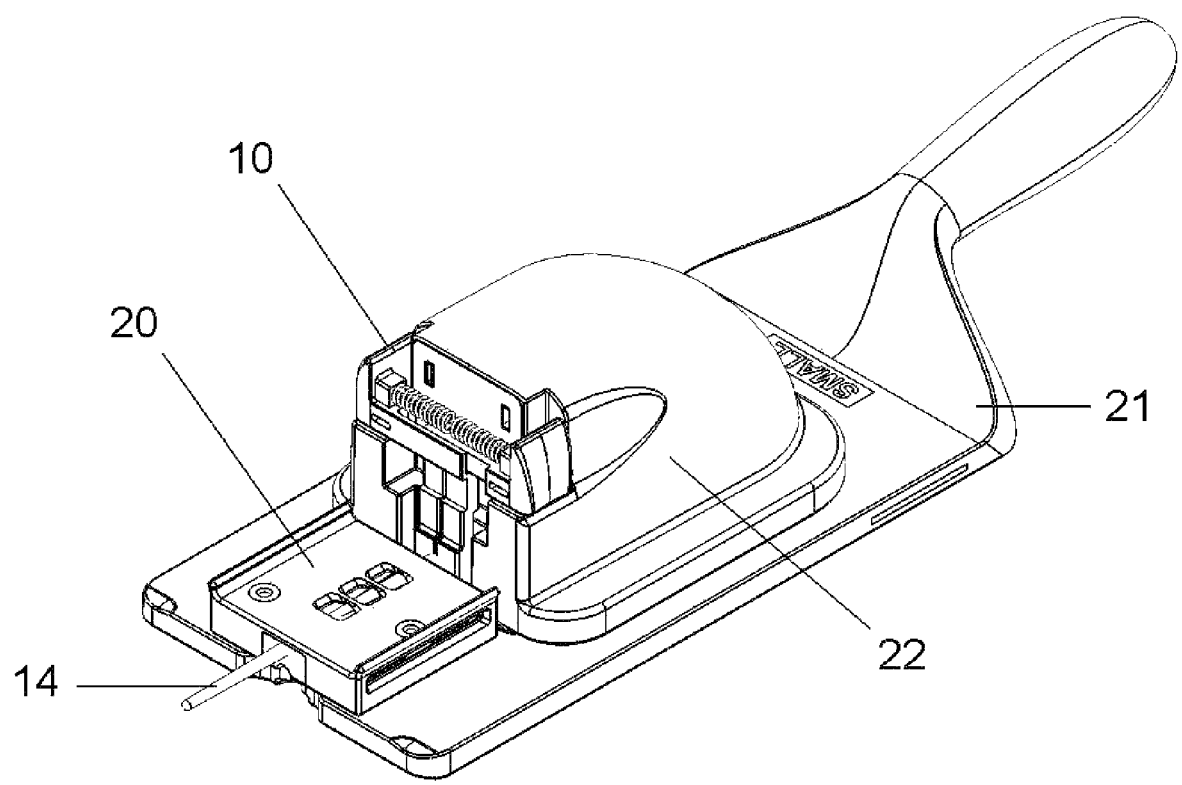
FIG. 14 depicts an exemplary restraining device with domed animal enclosure according to the present disclosure.
Figure 15:
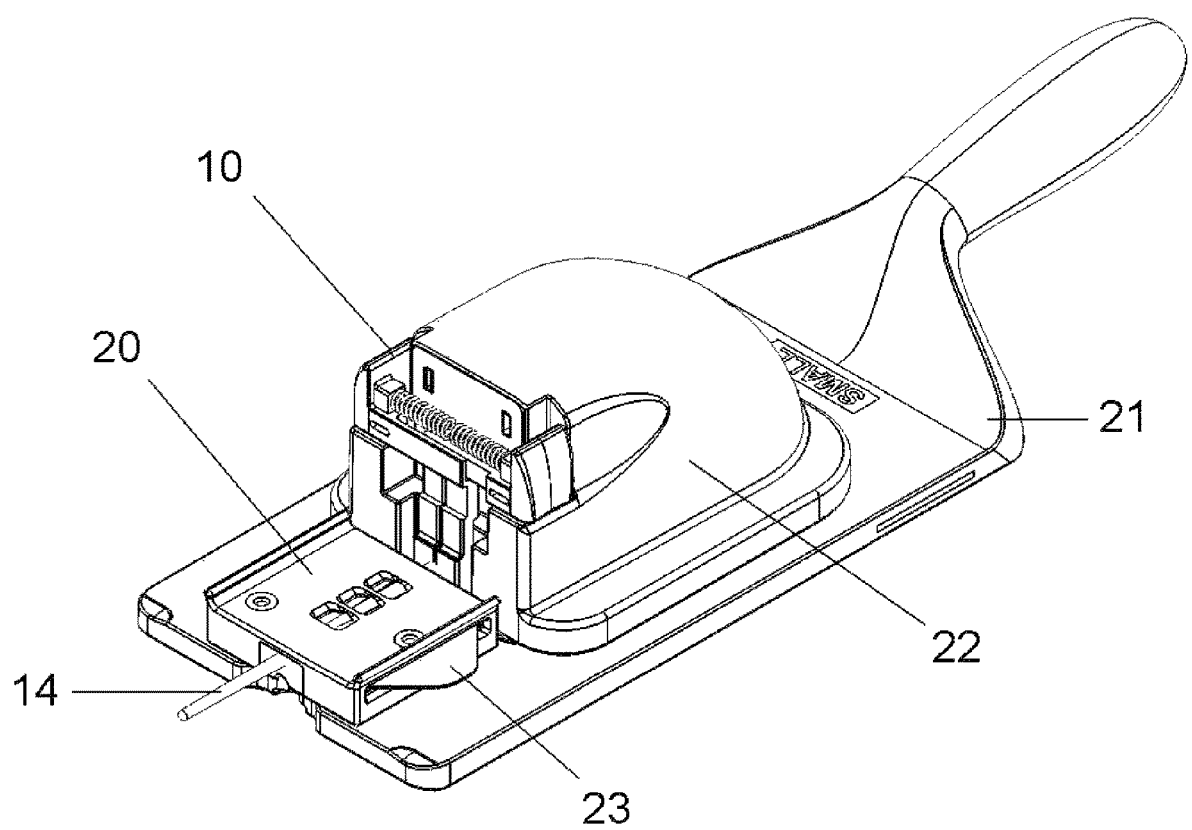
FIG. 15 depicts an exemplary restraining device and an exemplary media transfer assembly according to the present disclosure.

Referring now to FIG. 12, the restraining device 2 may in some embodiments include a body part plate assembly 20 and a body part cleat 10. In particular, the restraining device 2 may in some embodiments include a tail cleat 10, as illustrate in FIG. 8, and further comprises a tail plate assembly 20, as illustrated in FIGS. 9-11. The tail cleat 10 restrains the tail (or substrate portion thereof) from moving longitudinally (e.g. along the Y axis) while the tail plate assembly 20 restrains the tail (or substrate portion thereof) from moving laterally and/or vertically (e.g. from movement along the X, Z, and/or R axes). In one embodiment, marks made on a substrate restrained by such a restraining device 2 are characterized with enhanced precision.

Figure 19:
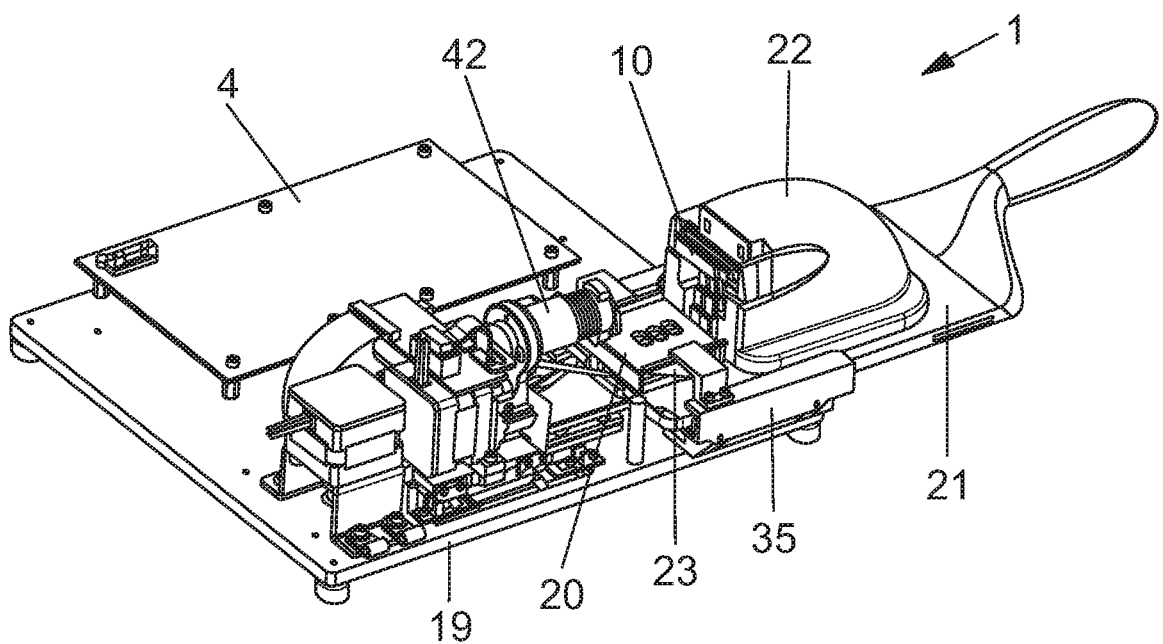
FIG. 19 depicts an exemplary marking system according to the present disclosure.
Figure 20:
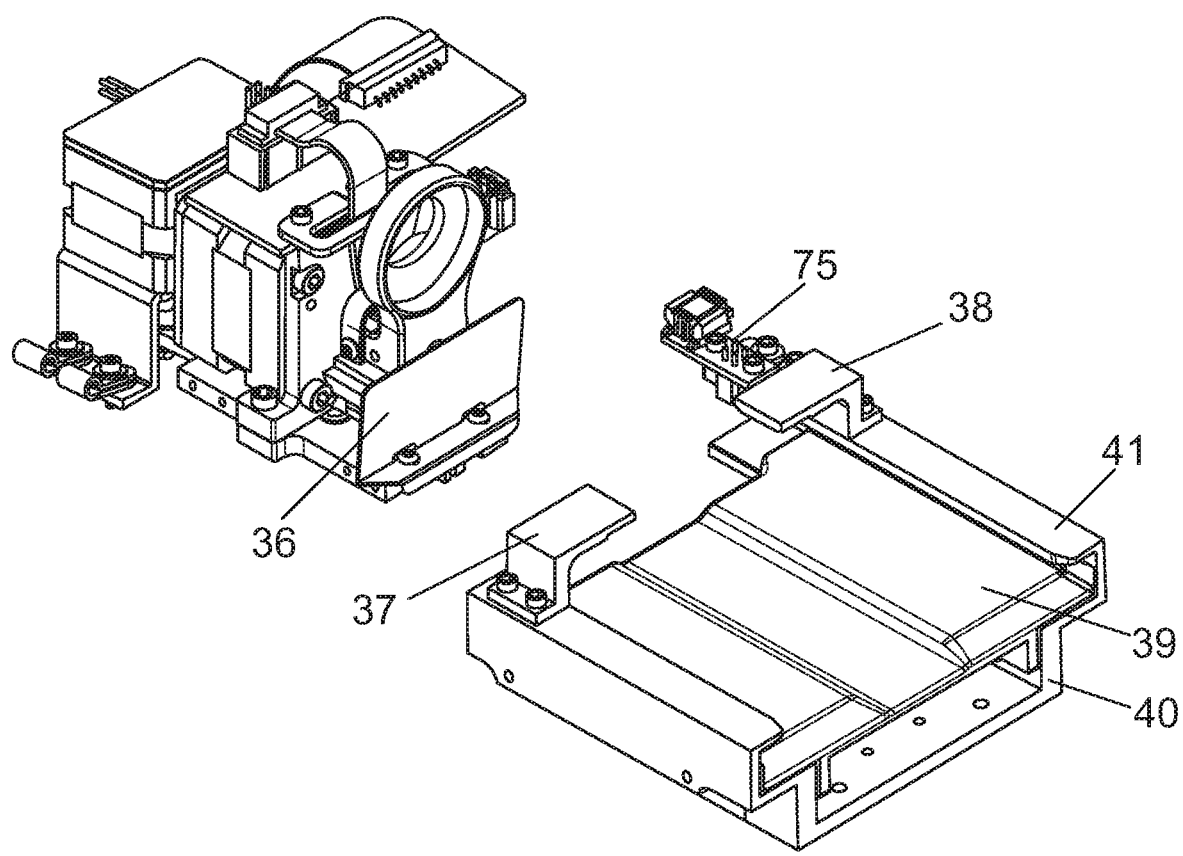
FIG. 20 depicts an exemplary receiving device for the restraint device according to the present disclosure.

Although the components of the restraining device 2 are in other embodiments directly supported by a primary baseplate 19 of the marking system 1 (FIG. 19), the components of the restraining device 2 can be supported by a baseplate 21 that is detachable from (reversibly fixed with respect to) the marking system 2. Such a configuration allows for rapid and consistent (error-free) loading and unloading of an animal into the restraining device 2. In addition, such a configuration allows the marking system 1 to independently accommodate multiple restraining devices 2 so that the marking system 1 can mark a first animal in a first restraining device while the user loads a second animal in a second restraining device, thereby reducing the time required for marking a batch of animals.

Tail Gauge

The marking system of the present disclosure may in some embodiments further include an optional measuring device 125 to measure the size of the marking substrate. For example, the measuring device 125 may in some embodiments be a mechanical gauge 126, such as a tail gauge, that can be used to measure the girth of a mouse tail for purposes of determining the appropriate restraining device and inserter necessary to achieve the appropriate depth of dermal layer placement of the marking pigment. An actual girth measurement is a more accurate and repeatable means of determining the appropriate restraining device and inserter combination than say age or weight of the animal. The girth of the tail at a particular age or weight will vary greatly depending on a number of factors, for example strain of mouse, gender, diet, litter size, etc.

In one embodiment, the girth of the mouse tail nearest the body is used to determine the optimal combination of inserter length and supporting v-groove in the restraining device to satisfy the marking target depth.

Figure 41:
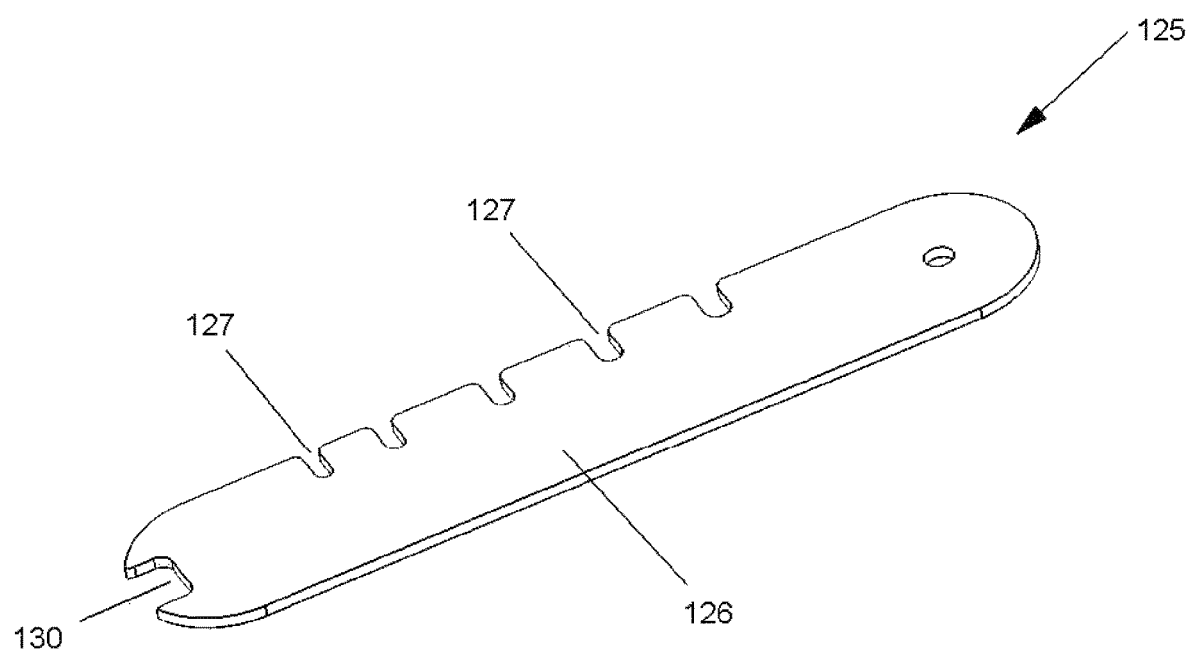
FIG. 41 depicts an exemplary inserter cartridge extraction tool according to the present disclosure.

In one non-limiting embodiment illustrated in FIG. 41, the girth of the substrate body part is measured using a tail gauge 126 having a plurality of grooves 127 with incrementally increasing widths that correspond to the optimal combination of inserter length and restraining device.

Optionally, the grooves 127 of the tail gauge are or are about 0.094", 0.105", 0.115", 0.128", and 0.140" in width, each approximately corresponding to the age and weight ranges of mice shown in the table below.

| Groove Width | | Mouse | |
| --- | --- | --- | --- |
| (in.) | (mm) | Weight (grams) | Age (weeks) |
| 0.094 | 2.39 | <8 | <2 |
| 0.105 | 2.67 | 8-10 | 2-3 |
| 0.115 | 2.92 | 11-15 | 3-4 |
| 0.128 | 3.25 | 16-22 | 4-5 |
| 0.140 | 3.56 | 23-30 | 5-6 |

Optionally, the measurement is made manually by the user lowering the grooved gauge over the tail nearest the body of the mouse, and finding the smallest groove 127 that fits (i.e. drops) comfortably over the girth of the tail.

The girth measurement may in some embodiments alternatively be made in non-contact fashion by the marking system. In one embodiment, the marking system includes a laser-based measuring device 128 that measures the girth of the body part by using a laser light curtain and a receiver that is incorporated into the system, as schematically illustrated in FIG. 50.

In a refinement of this embodiment, the measurement is made manually, by the user introducing the body part into the path of the light curtain.

In another refinement of this embodiment, the measurement is made automatically by breaking the path of the light curtain when the user introduces the restraining device into the marking system.

Cartridge Removal Tool

A cartridge removal tool 130, useful according to the present disclosure, may be optionally provided to remove the inserter cartridge 92 from the identification device 3. For example, when the inserter cartridge includes locking clips (e.g. pinch arms) that enable easily pushing-on and locking the inserter cartridge into place, the marking system may include an appropriately sized forked tool 130 for removal of the cartridge housing from the identification device, as illustrated in FIG. 49.

Figure 49:
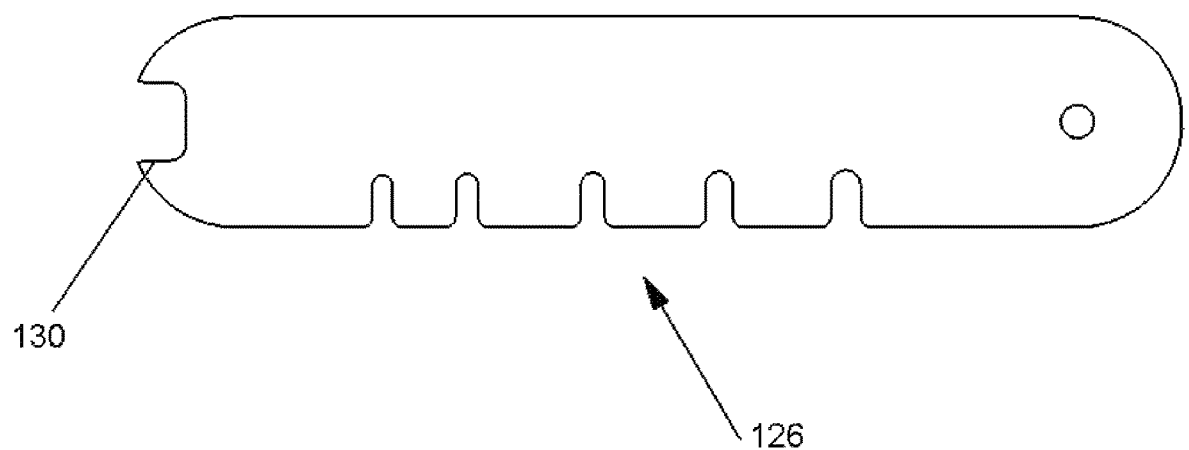
FIG. 49 depicts an exemplary measuring gauge according to the present disclosure, particularly illustrating the optional integration of the measuring gauge and the inserter cartridge extraction tool.

Optionally, the forked tool 130 may be integrated with measuring tail gauge 126 used to determine the girth of the substrate body part, as illustrated in FIGS. 41 and 49.

System Controller

In one embodiment, the controller 4 described herein is any controller that is able to control the position/movement of the robotic arm relative to the robot assembly and/or for actuating the identification device, for example a computer or microprocessor, or computer-interfacing device.

The present invention contemplates a computer program (e.g. recorded on a computer readable medium) comprising instructions for manipulating a robotic assembly to perform a function or method taught herein.

The controller manipulates the robotic assembly 42 to position the identification device 3 about the substrate and mark the substrate. The controller 4 can determine the position of substrate by existing instructions that informs the controller of the substrate's position.

In one embodiment, the controller 4 contains a program that is responsive to one or more feedback mechanisms (e.g. sensors).

In another embodiment, the controller 4 contains an algorithm such as PID to control one or more servo-based actuators (e.g. marking actuators).

The system controller 4 provides positioning and character mapping instructions to the inserter for producing the desired substrate marking. The direction of inserter travel relative to the substrate to be deposited can influence the results in some embodiments. In some embodiments, the identification device is operated by a controller to deposit the microelectronic chip in a proximal to distal direction parallel to the animal tail. In some embodiments, the microelectronic chip implant device is operated by the controller to implant the microelectronic chip in a distal to proximal direction parallel to the animal tail. In some embodiments, the microelectronic chip implant device is operated by the controller to implant the microelectronic chip vertical to the animal tail.

Marking Device

The marking system further includes a marking device to deliver a pigment to the marking substrate in some embodiments. The marking device and media transfer assembly are described in U.S. Provisional Application Nos. 61/637,767 and 61/239,430, both incorporated herein in entirety.

Animal Identification System

Figure 55:
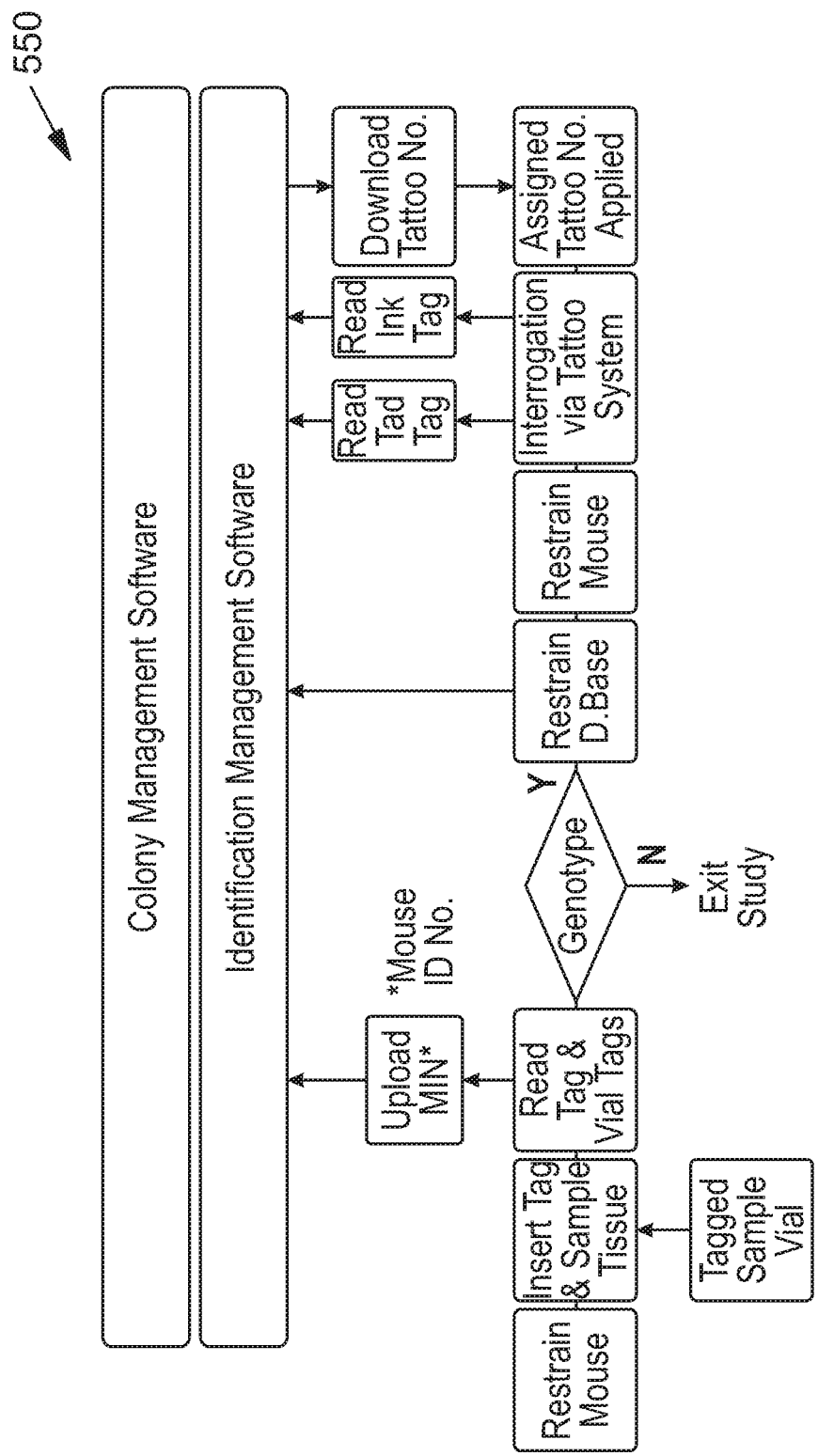
FIG. 55 depicts an animal identification system (in partially view) according to the present disclosure.

In practice, one embodiment of the process flow for independently combining the independent visual and electronic identification methods is diagrammatically illustrated in FIG. 55. In the flow diagram, a mouse may be selected for microelectronic chip implantation (i.e. tagging) as early as 5 days of age. The implantation would be achieved by means of either a manual or automated chip inserter instrument. Once tagged, the chip remains with the animal for the duration of its life.

In the case where the animal needs to be genotyped, a tissue sample may also be taken concurrently with the animal being tagged. The genotyping analysis is typically done at an independent laboratory, thus traceability of the sample needs to be tied to the tag implanted in the animal. The tissue sample may be collected in, for example a vial or a 96-well microtiter plate. The sample collection container may be tagged with a similar microelectronic chip, and both the animal and the container may be scanned to upload and associatively link the two identification numbers within the colony management software.

After genotyping, those animals that meet the test criteria are identified and reconciled or registered in the colony management software. These may proceed to be additionally identified with a permanent visual identification mark. Those not meeting the genotyping test criteria may or may not require a permanent visual identification mark.

For those animals requiring a permanent visual identification mark, this would be completed by introducing the animal into the automated tattoo system where either an external or integrated chip reader would read the animal tag. The identification management software would recognize the tag number from the post-genotyping reconciliation step, and assign an alpha-numeric visual identification number to be tattooed onto the animal. The alpha-numeric tattoo identification might or might not be the same, or a subset of, the electronic tag number, suffice the visual and electronic numbers would ever-after be associated via the identification management software.

In a further embodiment, the media transfer assembly containing the tattoo ink used to mark the animal may also be tagged as part of its manufacturing process using a similar microelectronic chip or an implanted bar-code in order to provide traceability and validation of all substances that come into contact with, or that is applied to, the animal.

Animal Identification Device and System

Provided herein is a microelectronic animal identification device 3 comprising an inserter 5 configured to releasably hold a microelectronic chip at a distal end of the inserter tip 5*b*, and an actuator 8 configured to release the microelectronic chip 330 from the inserter tip 5*b* when the distal end of the inserter tip is inserted into a substrate of an animal body part, wherein optionally, the animal 9 is a mouse, a rat, or a rodent; optionally, the body part is a tail 14; and optionally, the substrate is dermis.

In some embodiments, the device further comprises a controller 4 configured to control position of the inserter 5 and to actuate the actuator 8 to push the plunger 230 to implant the microelectronic chip 300 into the substrate of the animal body part.

In some embodiments of the identification device, the actuator is manually operated.

As illustrated in FIG. 53, in some embodiments of the identification device the inserter tip 5*b* terminates into a sharp tip 220 capable of piercing into the substrate of the animal body part.

In some embodiments of the identification device, the inserter tip 5*b* is configured to retain the microelectronic chip 300 in proximity of the sharp tip 220.

In some embodiments of the identification device, the inserter comprises a tubular body defining a lumen 221 configured to securely retain the microelectronic chip at a distal end of the lumen.

In some embodiments of the identification device, the lumen 221 is dimensioned to limit the movement of microelectronic chip 300 at the distal end of the lumen.

In some embodiments of the identification device, the lumen 221 has a diameter that is slightly larger than a cross-sectional profile of the microelectronic chip 330.

In some embodiments of the identification device, the distal end of the lumen 221 is dimensioned to approximate the cross-sectional profile of the microelectronic chip 300.

In some embodiments of the identification device, the microelectronic chip 300 is secured to the end of the lumen 5*b* with a biosafe adhesive.

In some embodiments of the identification device, the tubular body terminates into a sharp tip 220 extending distally beyond the microelectronic chip 300.

In some embodiments of the identification device, the microelectronic chip 300 includes a sharp end extending beyond a distal end of the tubular body.

In some embodiments of the identification device, the actuator 8 comprises a plunger 230 slidably inserted into the lumen 221.

In some embodiments of the identification device, the microelectronic chip 300 is secured inside of the lumen 221 with a biosafe adhesive.

In some embodiments of the identification device, the plunger 230 is configured to engage and push the microelectronic chip 300 out of the lumen 221 when the distal end of the lumen 220 is inserted into the substrate of the animal body part.

In some embodiments of the identification device, the plunger 230 is configured to disengage the microelectronic chip 300 by a proximal movement of the plunger to limit rotation of the microelectronic chip in the substrate of the animal body part.

In some embodiments of the identification device, the plunger 230 is actuated by a controller 4.

In some embodiments of the identification device, the plunger 230 is manually actuated.

In some embodiments of the identification device the microelectronic chip 300 comprises a passive RFID chip.

In some embodiments of the identification device the microelectronic chip 300 comprises a photocell 310 energized by a laser that provides power to the microelectronic chip.

In some embodiments, the microelectronic chip implant device is configured to implant the microelectronic chip 300 beneath the epidermis of the animal body part at a depth that allows the photocell 310 to be activated, optionally by a laser that emits 5-60 mW of optical power at 660 nm.

In some embodiments, the identification device further comprises a chip reading device 128 for photo-activating the microelectronic chip and for receiving the RF signal generated by the RF antenna 360.

In some embodiments, the chip reading device comprises a laser diode driver for photo-activating the microelectronic chip.

In some embodiments, the chip reading device comprises an optical focusing module.

In some embodiments of the identification device the microelectronic chip comprises an RF antenna capable 360 of generating an RF signal that represents an identification number.

In some embodiments of the identification device the RF antenna comprises an antenna loop.

In some embodiments of the identification device the microelectronic chip further comprises an onboard logic circuitry 320, 340 capable of modulating current in the antenna loop to generate a different RF signal that represents a different identification number.

In some embodiments of the identification device the onboard logic circuitry is controlled by an electronic memory 330.

In some embodiments of the identification device the electronic memory 330 is a ROM.

In some embodiments of the identification device the microelectronic chip further comprises an animal location detector.

In some embodiments of the identification device the microelectronic chip further comprises a laminated thin-film movement detector.

In some embodiments of the identification device the microelectronic chip further comprises a laminated thin-film vital sign detector.

In some embodiments of the identification device the vital sign detector is selected from the group consisting of heart rate detector, ECG detector, EEG detector, EMG detector, temperature detector, blood pressure detector, and combinations thereof.

In some embodiments of the identification device the microelectronic chip implant device is configured to implant the microelectronic chip beneath the epidermis of the animal body part at a depth that allows the RF signal to be detected.

In some embodiments, the identification device further comprises a chip reading device 128 as illustrated in FIG. 50 for activating the microelectronic chip and for receiving the RF signal generated by the RF antenna.

In some embodiments, the chip reading device comprises an air coil pickup connected to an RF receiver for receiving the RF signal generated by the microelectronic chip.

In some embodiments, the chip reading device comprises a field-programmable gate array (FGPA).

In some embodiments, the chip ready device comprises a USB microcontroller and power regulators.

Provided herein is an animal marking system 1 comprising each of the features previously described and further comprising at least one restraining device 22 operatively associated with the identification device, wherein the restraining device is sized and configured for restraining an animal or animal body part thereof and oriented such that the identification device can deposit a microelectronic chip 330 into the substrate of the animal body part.

In some embodiments, the inserter 5 is coupled to an inserter cartridge 92.

In some embodiments, the inserter cartridge 92 comprises a reference feature configured to position the inserter cartridge 92 on the identification device with precision. In some embodiments, the reference feature comprises a locating cylinder 94 extending between two end plates 95, 96.

In some embodiments, the identification device comprises a docking member coupled to a scotch yoke, the docking member defining a receiving slot extending from a top surface to a bottom surface of the docking member. In some embodiments, the locating cylinder of the reference feature is configured to be inserted into the receiving slot of the docking member. In some embodiments, the two end plates of the reference feature respectively engage the top and bottom surfaces of the docking member when the locating cylinder of the reference feature is inserted into the receiving slot of the docking member.

In some embodiments, the locating cylinder comprises a center bore through which the inserter extends.

In some embodiments of the marking system 1, the inserter cartridge 92 comprises a locking feature 110 configured to lock the inserter cartridge onto the identification device. In some embodiments, the locking feature comprises a U-shaped flexible locking clip extending between two ends, each end of the locking clip 110 comprises at least one outwardly extending locking teeth. In some embodiments, the locking clip further comprises a plurality of gripping ribs on an exterior surface of the locking clip. In some embodiments, the locking teeth are configured to abut an end wall of a scotch yoke of the microelectronic chip implant device when the inserter cartridge is in a mounted position.

In some embodiments, the inserter is coupled to the inserter cartridge by means of an adhesive. In some embodiments, the inserter is coupled to the inserter cartridge by molding the inserter to the inserter cartridge. In some embodiments, the inserter is molded from a polymer material. In still other embodiments, the inserter cartridge is permanently affixed to the identification device.

In some embodiments, the inserter cartridge is removable to allow replacement of worn or damaged inserters.

In any one of the embodiments of the marking system, the microelectronic chip implant device comprises multiple inserter cartridges dimensioned to account for differences in animal substrate size or geometry.

In some embodiments, the multiple inserter cartridges are pre-mounted onto the microelectronic chip implant device.

In any one of the embodiments of the marking system, the marking system is configured to automatically mount and dismount the inserter.

In some embodiments, the restraining device comprises a spring-loaded tapered v-groove configured to compensate for differences in size of the marking substrate. In some embodiments, the spring-loaded tapered v-groove is modulated to compensate for differences in size of the substrate body part. In some embodiments, the spring-loaded tapered v-groove is assembled in a support mount, and is optionally enclosed within a protective compliant boot. In still further embodiments, the modulated spring-loaded tapered v-groove comprises a plurality of independent groove sections, each groove section being articulating and self-aligning.

In any one of the embodiments of the marking system, the marking system is configured to select the inserter and the configuration of the restraining device based on the size of the marking substrate. In some embodiments, the marking system further comprises a measuring gauge configured to measure the size of the substrate of the animal body part, the measuring gauge comprising a plurality of measuring slots with incrementally increasing widths. In still further embodiments, the marking system further comprises a measuring device configured to measure the size of the substrate of the animal body part by using a laser-generating device emitting a light curtain beam and a receiver that is incorporated into the measuring device.

In some embodiments of the marking system, the marking system further comprises a forked tool adapted to engage and compress the locking clip to facilitate removal of the inserter cartridge from the microelectronic chip implant device. In some embodiments, the forked tool is integrated with a measuring gauge comprising a plurality of measuring slots with incrementally increasing widths.

Figure 23:
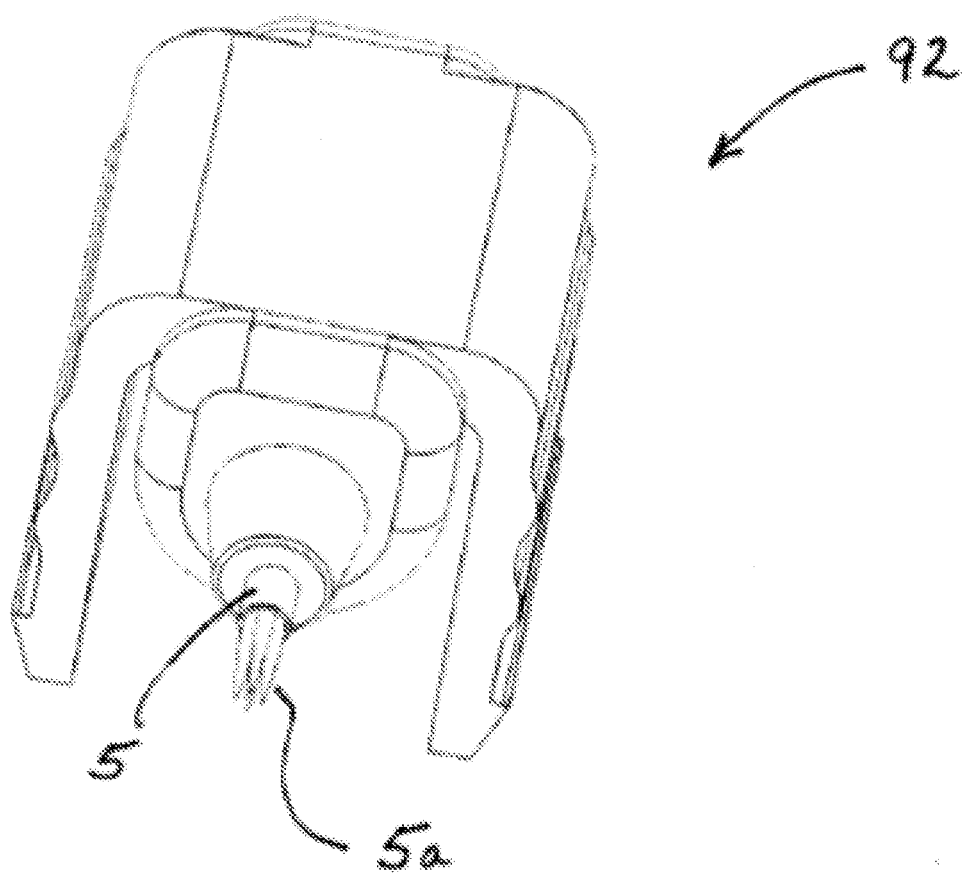
FIG. 23 depicts an exemplary multi-tip needle cartridge assembly used for marking the animal substrate (e.g.: with a tattoo) according to the present disclosure.

In some embodiments of the marking system, the marking system further comprises a marking device for depositing a pigment composition into the substrate of the animal body parts. In some embodiments, the marking device comprises a marking needle 5a of fixed length comprising one or a plurality of needle tips as illustrated in FIGS. 21b and 23. In some embodiments, the needle tips are configured to penetrate the epidermis of the marking substrate and transfer a pigment into the dermis of the marking substrate.

Figure 5:
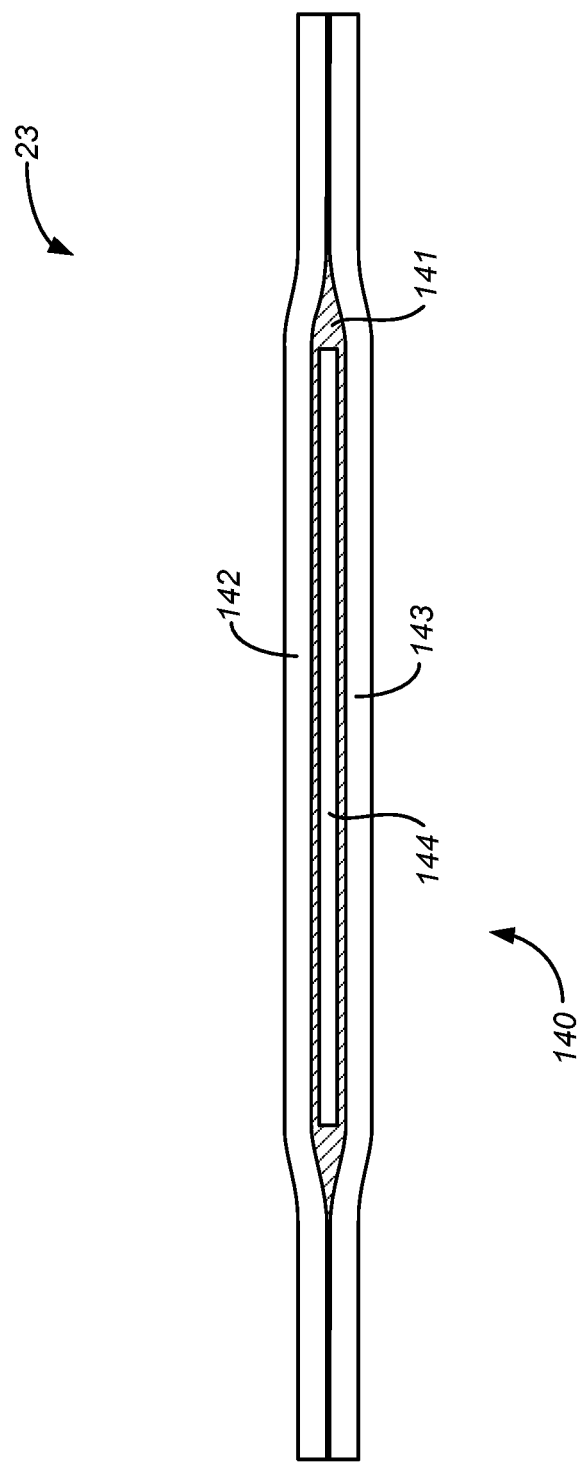
FIG. 5 depicts a media transfer assembly according to the present disclosure.
Figure 16:
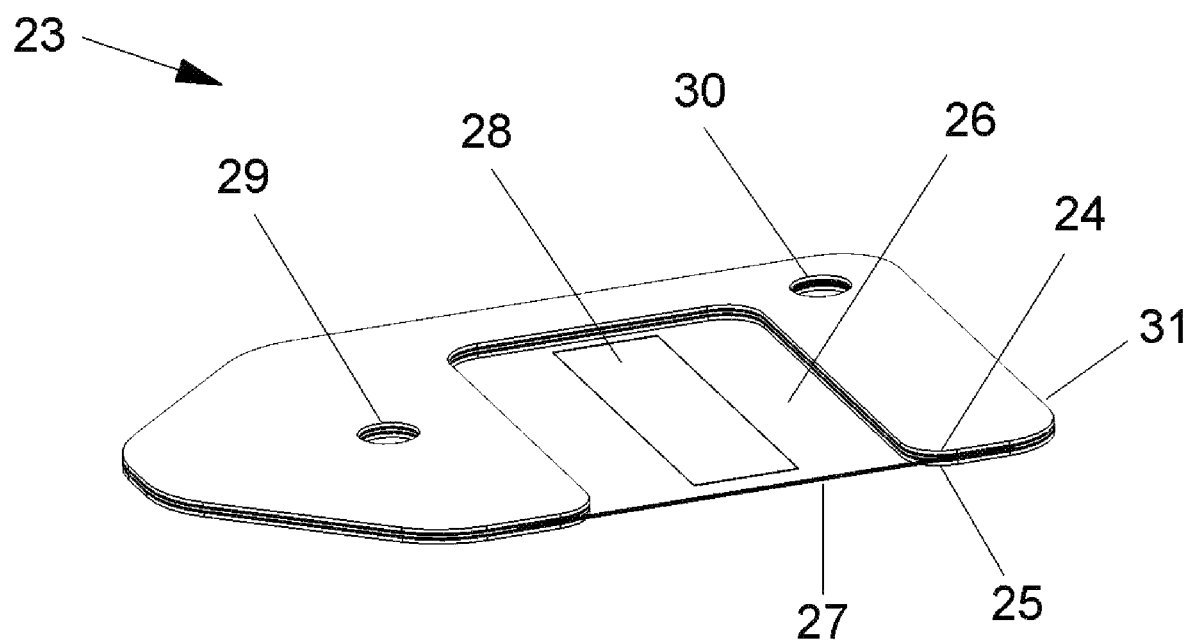
FIG. 16 depicts an exemplary media transfer assembly according to the present disclosure.
Figure 17:
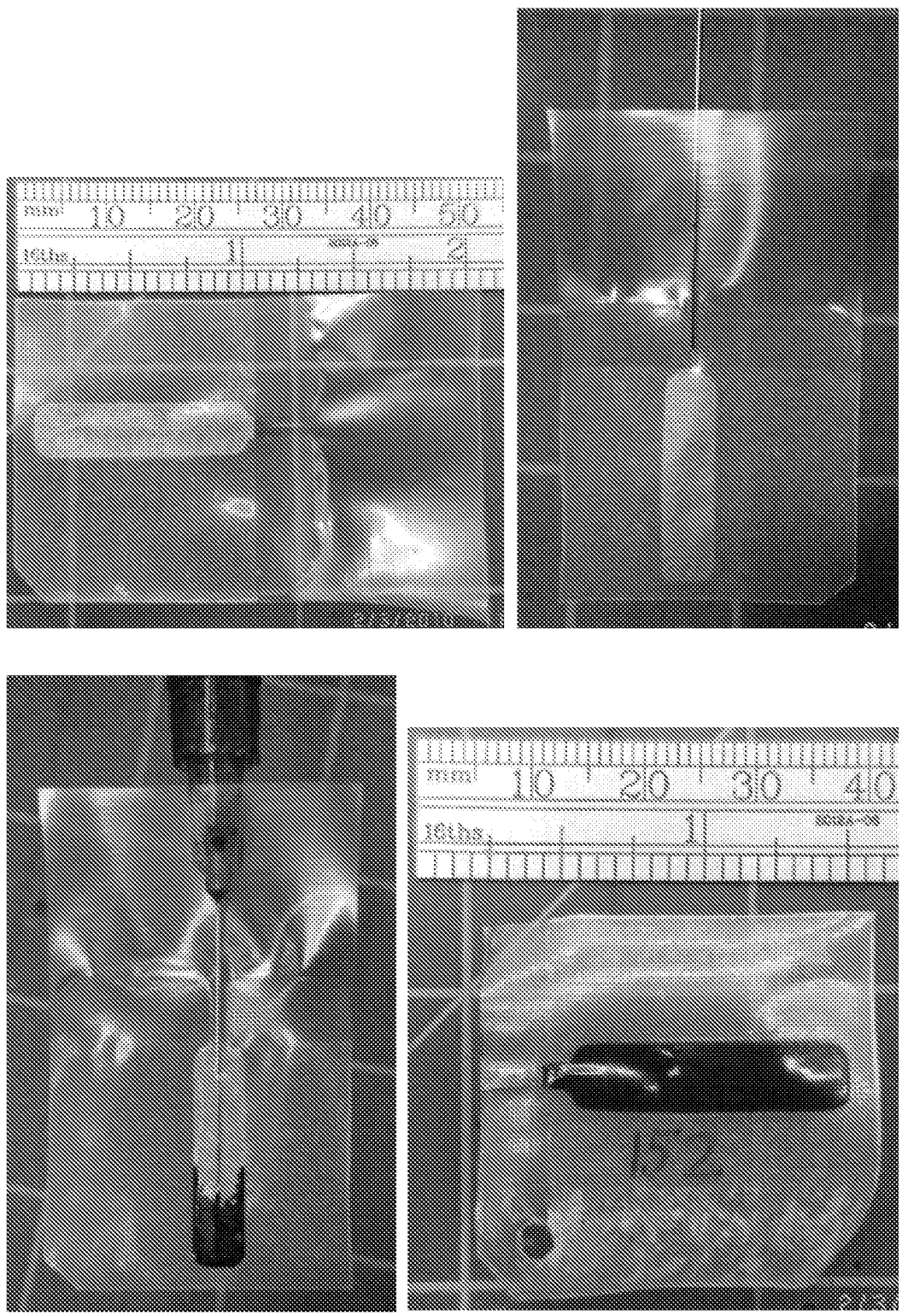
FIG. 17 depicts filling of a pigment compartment in an exemplary media transfer assembly according to the present disclosure.
Figure 18:
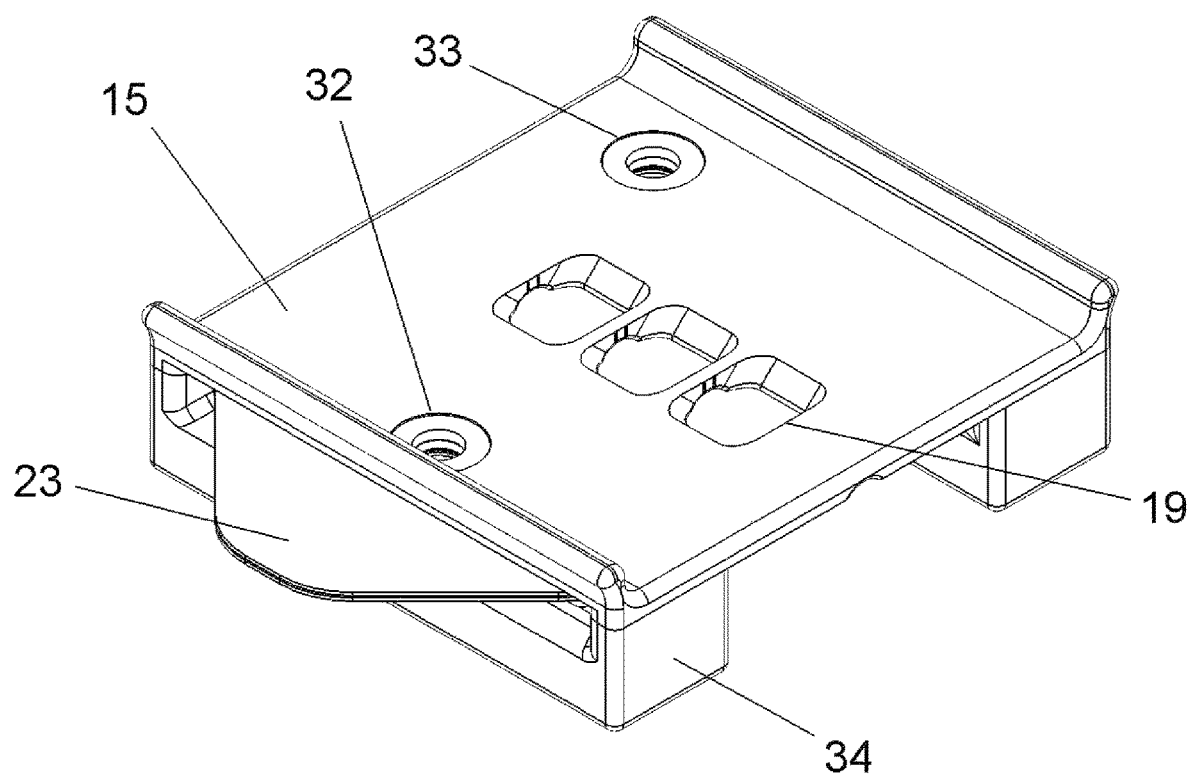
FIG. 18 depicts an exemplary media transfer assembly inserted into an exemplary body part restraint according to the present disclosure.

In any one of the embodiments of the marking system, the system further comprises a media transfer assembly as illustrated in FIGS. 5 and 16 containing the pigment, wherein the marking device is configured to make a mark by contacting the pigment prior to the marking substrate.

Provided herein is an identification device wherein the identification device is operated by a controller 4 to deposit the microelectronic chip 300 in a proximal to distal direction parallel to an animal tail 14.

In some embodiments of the identification device, the microelectronic chip implant device is operated by the controller 4 to implant the microelectronic chip 300 in a distal to proximal direction parallel to the animal tail 14.

In some embodiments, the microelectronic chip implant device is operated by the controller 4 to implant the microelectronic chip 300 vertical to the animal tail 14.

Provided herein is a microelectronic chip for identification of an animal, wherein the microelectronic chip 300 comprises a passive RFID chip.

Provided herein is a microelectronic chip for identification of an animal, wherein the microelectronic chip 300 comprises a photocell 310 that provides power to the microelectronic chip 300, an RF antenna 360 capable of generating an RF signal that represents an identification number, and a laminated thin-film detector.

In some embodiments of the chip, the laminated thin-film detector is a location detector. In some embodiments of the chip, the laminated thin-film detector is a movement detector. In some embodiments of the chip, the laminated thin-film detector is a vital sign detector.

In some embodiments of the identification device, the vital sign detector is selected from the group consisting of heart rate detector, ECG detector, EEG detector, EMG detector, temperature detector, blood pressure detector, and combinations thereof.

Provided herein is an animal identification system comprising: a microelectronic chip 300 implanted in a substrate of an animal, the microelectronic chip is photo-activated to generate an RF signal that represent a first identification number; and a pigment mark imprinted in the substrate of an animal, the pigment mark representing a second identification number.

In some embodiments of the system, the identification system further comprises a tissue storage container for containing a sample tissue of the animal, wherein the tissue storage container comprises a second microelectronic chip configured to an RF signal that represent the first identification number. In some embodiments, the sample tissue is taken when the microelectronic chip is implanted in the substrate of the animal.

In some embodiments of the system, the identification system further comprises a media transfer assembly that contains pigment used to mark the animal, wherein the media transfer comprises a third microelectronic chip configured to an RF signal that represent the first identification number. In some embodiments, the identification system further comprises a data management system for storing and cross-referencing the first, second and third identification numbers.

In some embodiments of the system, the identification system further comprises a secondary pigment identification bar-coding reference, for traceability to the manufacturer and manufacturing lot numbers included in the media transfer assembly wherein a sample of the pigment is contained, and wherein the media transfer assembly comprises a third microelectronic chip configured to an RF signal that represents the first identification number. In some embodiments, the identification system further comprises a data management system 550 for storing and cross-referencing the first, second and third identification numbers in addition to the bar-coding reference, for traceability to the manufacturer and manufacturing lot numbers.

Provided herein is an animal marking system 1 comprising: a microelectronic animal identification device 3, a pigment tattooing identification device 5, a restraining device 2, a measuring device 125, 126, a chip reader 128, a tissue sampling device, a media transfer assembly, and a data management system 550 for storing and cross-referencing identification numbers.

While only certain embodiments have been set forth, alternative embodiments and various modifications will be apparent from the above descriptions to those skilled in the art. These and other alternatives are considered equivalents and within the spirit and scope of this disclosure.

What is claimed is:

1. A microelectronic animal identification device for a rodent used as a laboratory test animal, the device comprising:
   an inserter configured to releasably hold a radio frequency identification (RFID) tag at a distal end of the inserter;
   a restraining device configured to restrain the rodent such that an upper part of a tail of the rodent presents a substrate to the distal end of the inserter;
   an actuator configured to release the RFID tag from the inserter when the distal end of the inserter is inserted into the substrate of the upper part of the tail;
   a marking device configured to deposit a pigment composition into the substrate of the upper part of the tail; and
   a controller configured to control a position of the inserter and to actuate the actuator to be configured to release the RFID chip from the inserter to implant the RFID tag in the upper part of the tail of the rodent wherein the RFID tag represents a first identification associated with the rodent, and to actuate the marking device to create a marking identification on the upper part of the tail of the rodent, wherein the marking identification represents a second identification associated with the rodent.

2. The identification device of claim 1, wherein the inserter is configured to implant the RFID tag beneath the epidermis of the upper part of the tail at a depth that allows an RF signal to be detected by the RFID tag and provide power to the RFID tag.

3. The identification device of claim 1, wherein the inserter, the marking device and the restraining device are configured to be positioned relative to one another based on a size of the marking identification to be created on the upper part of the tail of the rodent.

4. The identification device of claim 1, further comprising a media transfer assembly containing the pigment composition, wherein the marking device is configured to make a mark by contacting the pigment composition with at least one needle prior to marking the substrate with the at least one needle.

5. The identification device of claim 1, further comprising a data management system configured to interact with the identification device to store and cross-reference the first identification associated with the rodent and the second identification associated with the rodent.

6. The identification device of claim 1, further comprising a robotic assembly configured to interact with the controller to automatically control operation of the inserter along a Y-axis, a theta axis and an R axis.

7. The identification device of claim 6, wherein the robotic assembly is further configured to interact with the marking device to create the marking identification.

8. A microelectronic animal identification device for a rodent used as a laboratory test animal, the device comprising:
   an inserter cartridge configured to releasably hold a radio frequency identification (RFID) tag at a distal end of a needle;
   a restraining device configured to restrain the rodent such that an upper part of a tail of the rodent presents a substrate to the distal end of the needle; and
   an actuator operably coupled to the inserter cartridge and configured to release the RFID tag from the needle when the distal end of the needle is inserted into the substrate of the upper part of the tail protruding from the restraining device to implant the RFID tag in the upper part of the tail of the rodent,
   wherein the inserter cartridge includes a reference feature configured to position the inserter cartridge relative to the actuator in a predetermined orientation, and a locking feature configured to lock the inserter cartridge onto the actuator.

9. A microelectronic animal identification device for a rodent used as a laboratory test animal, the device comprising:
- an inserter cartridge configured to releasably hold a radio frequency identification (RFID) tag at a distal end of a needle;
- a restraining device configured to restrain the rodent such that an upper part of a tail of the rodent presents a substrate to the distal end of the needle; and
- an actuator operably coupled to the inserter cartridge and configured to release the RFID tag from the needle when the distal end of the needle is inserted into the substrate of the upper part of the tail protruding from the restraining device to implant the RFID tag in the upper part of the tail of the rodent,
- wherein the RFID tag further comprises a laminated thin-film vital sign detector.

10. The identification device of claim 9, wherein the thin-film vital sign detector is selected from the group consisting of heart rate detector, ECG detector, EEG detector, EMG detector, temperature detector, blood pressure detector, and combinations thereof.

11. A microelectronic animal identification device for a rodent used as a laboratory test animal, the device comprising:
- an inserter configured to releasably hold a radio frequency identification (RFID) tag at a distal end of the inserter; and
- a restraining device configured to restrain the rodent such that a tail of the rodent is presented in a generally fixed and stable position and orientation to permit implantation of the RFID tag below a substrate of an upper part of the tail of the rodent, the restraining device including:
  - a base plate having a pair of opposed members arranged as a tail cleat structure proximate to a distal portion of the base plate and defining a channel between the pair of opposed members having a width that is dimensioned to accommodate the tail of the rodent;
  - a biasing member configured to urge the pair of opposed members toward each other to decrease the width of the channel and assert a restraining force against the tail to restrict longitudinal movement of the tail; and
  - a body restraint defining a cavity configured to temporarily enclose a body of the rodent within the cavity when the body restraint is positioned on top of the base plate and allow the tail of the rodent to extend through the tail cleat structure and away from the body restraint; and
- an actuator configured to release the RFID tag from the inserter when the distal end of the inserter is inserted into the substrate of the upper part of the tail protruding from the restraining device to implant the RFID tag in the upper part of the tail of the rodent.

12. The identification device of claim 11, wherein the restraining device further comprising a reversible fixation mechanism configured to temporarily secure the body restraint to the base plate.

13. The identification device of claim 12, wherein the reversible fixation mechanism includes at least one magnet on at least one of the body restraint and the base plate.

14. The identification device of claim 11, wherein the tail cleat structure is operably attached to the base plate and the biasing member is operably carried by the body restraint and interfaces with the tail cleat structure when the body restraint is positioned on the base plate.

15. The identification device of claim 11, wherein the base plate includes a handle structure proximate to a proximal portion of the base plate and also includes a distal surface extending distally from the tail cleat structure, such that the body restraint is configured to be positioned between the handle and the tail cleat structure such that the tail of the rodent extends distally from the body restraint and a lower portion of the tail is supported by the distal surface of the base plate.

* * * * *